(12) United States Patent
Iandolino et al.

(10) Patent No.: US 10,988,764 B2
(45) Date of Patent: Apr. 27, 2021

(54) COMPOSITIONS AND METHODS FOR REGULATING GENE EXPRESSION VIA RNA INTERFERENCE

(71) Applicant: Monsanto Technology LLC, St. Louis, MO (US)

(72) Inventors: Alberto Iandolino, Davis, CA (US); Juan Pedro Sanchez, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/746,617

(22) Filed: Jun. 22, 2015

(65) Prior Publication Data
US 2016/0160212 A1 Jun. 9, 2016

Related U.S. Application Data

(60) Provisional application No. 62/015,950, filed on Jun. 23, 2014.

(51) Int. Cl.
 *C12N 15/113* (2010.01)
 *C12N 15/82* (2006.01)
 *C12N 15/11* (2006.01)

(52) U.S. Cl.
 CPC ......... *C12N 15/113* (2013.01); *C12N 15/111* (2013.01); *C12N 15/8218* (2013.01); *C12N 2310/14* (2013.01); *C12N 2320/51* (2013.01); *C12N 2320/52* (2013.01)

(58) Field of Classification Search
 None
 See application file for complete search history.

(56) References Cited

U.S. PATENT DOCUMENTS

| | | |
|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |

(Continued)

FOREIGN PATENT DOCUMENTS

| | | |
|---|---|---|
| AU | 2008258254 B2 | 7/2014 |
| AU | 2014262189 B2 | 11/2014 |

(Continued)

OTHER PUBLICATIONS

Jacque et al 2002 Nature 418:435-438.*
Fukunaga and Doudna 2009 The EMBO Journal 28:545-555 (Year: 2009).*
Agrios, *Plant Pathology* (Second Edition), 2:466-470 (1978).
Alarcón-Reverte et al., "Resistance to ACCase-inhibiting herbicides in the weed *Lolium multiflorum*," *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).

(Continued)

*Primary Examiner* — Brent T Page
(74) *Attorney, Agent, or Firm* — Arnold & Porter Kaye Scholer LLP; Amanda Carmany-Rampey; David R. Marsh

(57) ABSTRACT

The present disclosure provides compositions and methods for regulating gene expression via RNA-mediated silencing. The present disclosure also provides compositions and methods to optimize the processing of a dsRNA molecule into small RNA duplexes. The present disclosure further provides compositions and methods to improve the efficiency of a dsRNA molecule in producing desired small RNAs and promoting the silencing of a gene of interest.

17 Claims, 15 Drawing Sheets

Specification includes a Sequence Listing.

(56) References Cited

U.S. PATENT DOCUMENTS

| | | |
|---|---|---|
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |

(56) References Cited

U.S. PATENT DOCUMENTS

| | | |
|---|---|---|
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,169,483 B2* | 10/2015 | Davidson ............. C12N 15/113 |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 1/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1 | 11/2003 | Rottmann et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cal et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1* | 11/2007 | Rivory ............... A61K 31/7105 435/6.18 |
| 2007/0281900 A1 | 12/2007 | Cul et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0208564 A1* | 8/2009 | Li ..................... C12N 15/111 424/450 |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0203013 A1 | 8/2011 | Peterson et al. |
| 2011/0296555 A1 | 12/2011 | Ivashuta et al. |
| 2011/0296556 A1* | 12/2011 | Sammons ............... A01N 63/02 800/298 |
| 2012/0036594 A1 | 2/2012 | Cardoza et al. |
| 2012/0107355 A1 | 5/2012 | Harris et al. |

(56) References Cited

U.S. PATENT DOCUMENTS

| | | | |
|---|---|---|---|
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0174262 A1 | 7/2012 | Azhakanandam et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | | |
|---|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |
| JP | 2009137851 A | 6/2009 |
| RU | 2 291 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |

(56) References Cited

FOREIGN PATENT DOCUMENTS

| | | |
|---|---|---|
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A2 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/02690 A1 | 3/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/038788 A2 | 8/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/156342 A1 | 11/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |

(56) References Cited

FOREIGN PATENT DOCUMENTS

| WO | WO 2014/106837 A2 | 7/2014 |
|---|---|---|
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Ambrus et al., "The Diverse Roles of RNA Helicases in RNAi," *Cell Cycle*, 8(21):3500-3505 (2009).
An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).
Andersson et al., "A novel selection system for potato transformation using a mutated AHAS gene," *Plant Cell Reports*, 22(4):261-267 (2003).
Anonymous, "A handbook for high-level expression and purification of 6xHis-tagged proteins," *The QUIexpressionist*, (2003).
Anonymous, "Agronomy Facts 37: Adjuvants for enhancing herbicide performance," n.p., 1-8, (Jan. 26, 2000), Web, (Jan. 21, 2014).
Anonymous, "Devgen, The mini-Monsanto," KBC Securities (2006).
Anonymous, "Do Monsanto have the next big thing?," *Austalian Herbicide Resistance Initiative (AHRI)*, (Apr. 23, 2013) Web. (Jan. 19, 2015).
Aoki et al., "In Vivo Transfer Efficiency of Antisense Oligonucleotides into the Myocardium Using HVJ—Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmymovich, "Using RNA interference to increase crop yield and decrease pest damage," *MMG 445 Basic Biotech.*, 5(1):7-12 (2009).
Australian Patent Examination report No. 1 dated Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bai et al., "Naturally Occurring Broad-Spectrum Powdery Mildew Resistance in a Central American Tomato Accession Is Caused by Loss of *Mlo* Function," MPMI, 21(1):30-39 (2008).
Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).
Baulcombe, "RNA silencing and heritable epigenetic effects in tomato and *Arabidopsis*," Abstract 13*th* Annual Fall Symposium, Plant Genomes to Phenomes, Donald Danforth Plant Science Center, 28-30 (2011).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Bourgeois et al., "Field and producer survey of ACCase resistant wild oat in Manitoba," *Canadian Journal of Plant Science*, 709-715 (1997).
Breaker et al., "A DNA enzyme with $Mg^{2+}$-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Brugière et al., "Glutamine Synthetase in the Phloem Plays a Major Role in Controlling Proline Production," *The Plant Cell*, 11:1995-2011 (1999).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Campbell et al., "Gene-knockdown in the honey bee mite *Varroa destructor* by a non-invasive approach: studies on a glutathione 5-transferase," *Parasites & Vectors*, 3(1):73, pp. 1-10 (2010).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chang et al., "Cellular Internalization of Fluorescent Proteins via Arginine-rich Intracellular Delivery Peptide in Plant Cells," *Plant Cell Physiol.*, 46(3):482-488 (2005).
Chee et al., "Transformation of Soybean (*Glycine max*) by Infecting Germinating Seeds with *Agrobacterium tumefaciens*," *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 505 Ribosomal Subunits of *Arabidopsis* chloroplasts," *Plant Physiology*, 158:693-707 (2012).
Chinese Office Action dated Aug. 28, 2013 in Chinese Application No. 201180012795.2.
Chupp et al., "Chapter 8: White Rust," *Vegetable Diseases and Their Control*, The Ronald Press Company, New York, pp. 267-269 (1960).
Clough et al., "Floral dip: a simplified method for Agrobacterium-mediated transfoimation of *Arabidopsis thaliana*," *The Plant Journal*, 16(6):735-743 (1998).
CN101914540 Patent Diclosure, "Introduction of RNA into plant by interference," (2010).
Colbourne et al., "The Ecoresponsive Genome of Daphnia pulex," *Science*, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 916.3.
Cooney et al., "Site-Specific Oligonucleotide Binding Represses Transcription of the Human c-myc Gene in Vitro," *Science*,241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Dalmay et al., "An RNA-Depenedent RNA Polymerase Gene in *Arabidopsis* Is Required for Posttranscriptional Gene Silencing Mediated by a Transgene but Not by a Virus," *Cell*, 101:543-553 (2000).

(56) References Cited

OTHER PUBLICATIONS

Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
Della-Cioppa et al., "Import of a precursor protein into chloroplasts is inhibited by the herbicide glyphosate," *The EMBO Journal*, 7(5):1299-1305 (1988).
Desai et al., "Reduction in defoiiiied wing virus infection in larval and adult honey bees (*Apis mellifera* L.) by double-stranded RNA ingestion," *Insect Molecular Biology*, 21(4):446-455 (2012).
Diallo et al., "Long Endogenous dsRNAs Can Induce Complete Gene Silencing in Mammalian Cells and Primary Cultures," *Oligonucleotides*, 13:381-392 (2003).
Dietemann et al.,"*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Emery et al., "Radial Patterning of *Arabidopsis* Shoots by Class III HD-ZIP and KANADI Genes," *Current Biology*, 13:1768-1774 (2003).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Farooq et al., "Rice seed priming," *IPRN*, 30(2):45-48 (2005).
Final Office Action dated Nov. 7, 2013, in U.S. Appl. No. 13/042,856.
Fire et al., "Potent and specific genetic interference by double-stranded RNA in *Caenorhabditis elegans*," *Nature*, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated May 27, 2015, in Chinese Patent Application No. 201280054179.8.
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 dated May 16, 2014.
Gaines et al., "Gene amplification confers glyphosate resistance in *Amaranthus palmeri*," *Proc. Natl. Acad. Sci. USA*, 107(3):1029-1034 (2010).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"*Amaranthus hypochondriacus* acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank Accession No. GI:186478573, published Jan. 22, 2014.
GenEmbl FJ861243, published Feb. 3, 2010.
Gong et al., "Silencing of Rieske iron—sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on gell filiation of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus*?," *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).

(56) References Cited

OTHER PUBLICATIONS

Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus,*" *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL2013/050447.
International Search Report and the Written Opinion dated Feb. 25, 2013, in International Application No. PCT/US12/054883.
International Search Report and the Written Opinion dated Feb. 27, 2013, in International Application No. PCT/US12/054814.
International Search Report and the Written Opinion dated Feb. 27, 2013, in International Application No. PCT/US12/054842.
International Search Report and the Written Opinion dated Feb. 27, 2013, in International Application No. PCT/US12/054862.
International Search Report and the Written Opinion dated Feb. 27, 2013, in International Application No. PCT/US12/054894.
International Search Report and the Written Opinion dated Feb. 27, 2013, in International Application No. PCT/US12/054974.
International Search Report and the Written Opinion dated Feb. 27, 2013, in International Application No. PCT/US12/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US11/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jofre-Garfias et al., "*Agrobacterium*-mediated transformation of *Amaranthus hypochondriacus*: light- and tissue-specific expression of a pea chlorophyll a/b-binding protein promoter," *Plant Cell Reports*, 16:847-852 (1997).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana,*" *Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Khan et al., "Matriconditioning of Vegetable Seeds to Improve Stand Establishment in Early Field Plantings," *J. Amer. Soc. Hort. Sci.*, 117(1):41-47 (1992).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).
Kim et al., "Synthetic dsRNA Dicer substrates enhance RNAi potency and efficacy," *Nature Biotechnology*, 23(2):222-226 (2005).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA, PNAS*, 99(18):11981-11986 (2002).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kusaba et al., "*Low glutelin content1*: A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Leopold et al., "Chapter 4: Moisture as a Regulator of Physiological Reaction in Seeds," *Seed Moisture, CSSA Special Publication No. 14*, pp. 51-69 (1989).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli,*" *Nucleic Acids Research*, 29(17):3583-3594 (2001).
Li et al "Establishmept of a highly efficient transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of *Arabidopsis* and other plant species," *Plant Methods*, 5(6):1-15 (2009).

(56) References Cited

OTHER PUBLICATIONS

Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "OligoWalk: an online siRNA design tool utilizing hybridization thermodynamics," *Nucleic Acids Research*, 36:W104-W108 (2008).
Lu et al., "RNA silencing in plants by the expression of siRNA duplexes," *Nucleic Acids Res.*, 32(21):e171 (2004).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
MacKenzie et al., "Transgenic *Nicotiana debneyii* expressing viral coat protein are resistant to potato virus S infection," *Journal of General Virology*, 71:2167-2170 (1990).
Maher III et al., "inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Maori et al., "IAPV, a bee-affecting virus associated with Colony Collapse Disorder can be silenced by dsRNA ingestion," *Insect Molecular Biology*, 18(1):55-60 (2009).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).
Molina et al., "Inhibition of protoporphyrinogen oxidase expression in *Arabidopsis* causes a lesion-mimic phenotype that induces systemic acquired resistance," *The Plant Journal*, 17(6):667-678.

Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Apr. 11, 2013, in U.S. Appl. No. 13/042,856.
Non-Final Office Action dated Jul. 30, 2014, in U.S. Appl. No. 13/042,856.
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Ongvarrasopone et al., "A Simple and Cost Effective Method to Generate dsRNA for RNAi Studies in Invertebrates," *Science Asia*, 33:35-39 (2007).
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Ouellet et al., "Members of the Acetohydroxyacid Synthase Muligene Family of *Brassica napus* Have Divergent Patterns of Expression," *The Plant Journal*, Blackwell Scientific Publications, Oxford, GB, 2(3):321-330 (1992).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of Shrunken-2 Corn," *J. Amer. Soc. Hort. Sci.*, 119(3):629-635 (1994).
Partial Supplementary European Search Report dated Mar. 2, 2015, in European Patent Application No. 12 831 494.5.
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by *Arabidopsis* induces changes in the expression of CLE peptides which control root morphology," *Plant Signaling & Behavior*, 5(9):1112-1114 (2010).

(56) References Cited

OTHER PUBLICATIONS

Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Pratt et al., "Amaranthus rudis and *A. tuberculatus*, One Species or Two?," *Journal of the Torrey Botanical Society*, 128(3):282-296 (2001).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei, "Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix folination analyzed by a FRET assay," *BMC Biochemistry*, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 21, 2014, in U.S. Appl. No. 13/583,302.
Restriction Requirement dated Oct. 2, 2012, in U.S. Appl. No. 13/042,856.
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Ryabov et al., "Cell-to-Cell, but Not Long-Distance, Spread of RNA Silencing That Is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).

Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schweizer et al., "Double-stranded RNA interferes with gene function at the single-cell level in cereals," *The Plant Journal*, 24(6):895-903 (2000).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Senthil-Kumar et al., "A systematic study to determine the extent of gene silencing in Nicotiana benthamiana and other *Solanaceae* species when heterologous gene sequences are used for virus-induced gene silencing," *New Phytologist*, 176:782-791 (2007).
Sharma et al., "A simple and efficient *Agrobacterium*-mediated procedure for Transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Snead et al., "Molecular basis for improved gene silencing by Dicer substrate interfering RNA compared with other siRNA variants," *Nucleic Acids Research*, 41(12):6209-6221 (2013).
Steeves et al., "Transgenic soybeans expressing siRNAs specific to a major sperm protein gene suppress *Heterodera glycines* reproduction," *Funct. Plant Biol.*, 33:991-999 (2006).
Stevens et al., "New Formulation Technology—Silwet® Organosilicone Surfactants Have Physical and Physiological Properties Which Enhance the Performance of Sprays," *Proceedings of the $9^{th}$ Australian Weeds Conference*, pp. 327-331 (1990).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Street, "Why is DNA (and not RNA) a stable storage form for genetic information?," *Biochemistry Revisited*, pp. 1-4 (2008).
Sudarsan et al., "Metabolite-binding RNA domains are present in the genes of eukaryotes," *RNA*, 9:644-647 (2003).
Sun et al., "A Highly efficient Transfoiiiiation Protocol for Micro-Tom, a Model Cultivar for Tomato Functional Genomics," *Plant Cell Physiol.*, 47(3):426-431 (2006).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "Sweet delivery—sugar translocators as ports of entry for antisense oligodeoxynucleotides in plant cells," *The Plant Journal*, 52:1192-1198 (2007).
Sutton et al., "Activity of mesotrione on resistant weeds in maize," *Pest Manag. Sci.*, 58:981-984 (2002).
Takasaki et al., "An Effective Method for Selecting siRNA Target Sequences in Mammalian Cells," *Cell Cycle*, 3:790-795 (2004).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).

(56) References Cited

OTHER PUBLICATIONS

Temple et al., "Can glutamine synthetase activity levels be modulated in transgenic plants by the use of recombinant DNA technology?" *Transgenic Plants and Plant Biochemistry*, 22:915-920 (1994).
Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Tran et al., "Control of specific gene expression in mammalian cells by co-expression of long complementary RNAs," *FEBS Lett.*;573(1-3):127-134 (2004).
Tranel et al., "Resistance of weeds to ALS-inhibiting herbicides: what have we learned?," *Weed Science*, 50:700-712 (2002).
Tarina et al., "Tospoviruses in the Mediterranean Area," *Advances in Virus Research*, 84:403-437 (2012).
Tuschl, "Expanding small RNA interference," *Nature Biotechnol.*, 20: 446-448 (2002).
Tuschl, "RNA Interference and Small Interfering RNAs," *ChemBiochem.* 2(4):239-245 (2001).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).
Van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vermeulen et al., "The contributions of dsRNA structure to Dicer specificity and efficiency," *RNA*, 11(5):674-682 (2005).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants Is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Number of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al.,"*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.

(56) References Cited

OTHER PUBLICATIONS

Communication pursuant to Article 94(3) EPC dated Mar. 18, 2016, in European Patent Application No. 12 832 160.1.
Communication pursuant to Article 94(3) EPC dated Jan. 14, 2016, in European Patent Application No. 12 832 415.9.
Communication pursuant to Article 94(3) EPC dated Oct. 23, 2015, in European Patent Application No. 12 831 945.6.
Extended European Search Report dated Jan. 20, 2016, in European Patent Application No. 13 794 339.5.
Extended European Search Report dated Oct. 8, 2013, in European Patent Application No. 11753916.3.
Final Office Action dated Nov. 10, 2015, in U.S. Appl. No. 13/612,985.
Final Office Action dated Nov. 30, 2015, in U.S. Appl. No. 13/612,948.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated Sep. 9, 2015, in Chinese Patent Application No. 201280055409.2.
Fukunaga et al., "dsRNA with 5' overhangs contributes to endogenous and antiviral RNA silencing pathways in plants," *The EMBO Journal*, 28(5):545-555 (2009).
GenBank Accession No. GU120406, "Chrysomela tremulae ribosomal protein L7 (RpL7) mRNA, complete cds" (2009).
GenBank Accession No. Q4GXM3_BIPLU, "Ribosomal protein L7e" (2006).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. HD315444, "Sequence 192160 from Patent EP2213738" (2010).
GenBank Accession No. EW765249, "ST020010B10C12 Normalized and subtracted western corn rootworm female head cDNA library *Diabrotica virgifera virgifera* cDNA clone STO20010B10C12 5-, mRNA sequence," (2007).
GenBank Accession No. EW771198, "ST020010B10C12 Normalized and subtracted western corn rootworm female head cDNA library *Diabrotica virgifera virgifera* cDNA clone STO20010B10C12 5-, mRNA sequence," (2007).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. Y08611.1, "P.sativum mRNA for dihydropterin pyrophosphokinase/dihydropteroate synthase." (2006).
Guclkov, "Minireview: The L7/L12 ribosomal domain of the ribosome: structural and functional studies," *FEBS Letters*, 407:253-256 (1997).
Heffer et al., "Rapid isolation of gene homologs across taxa: Efficient identification and isolation of gene orthologs from non-model organism genomes, a technical report," *EvoDevo Journal*, 2(7):1-5 (2011).
International Search Report and Written Opinion dated Nov. 24, 2015, in International Application No. PCT/US2015/037522.
International Search Report and Written Opinion daed Nov. 27, 2015, in International Application No. PCT/US2015/037015.
International Search Report and Written Opinion dated May 26, 2016, in International Application No. PCT/US2016/014344.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Knudsen, "Promoter2.0: for the recognition of Poll promoter sequences," *Bioinformatics*, 15(5):356-361 (1999).
Lein et al., "Target based discovery of novel herbicides," *Current Opinion in Plant Biology*, 7:219-225 (2004).
Migge et al., "Greenhouse-grown conditionally lethal tobacco plants obtained by expression of plastidic glutamine synthetase antisense RNA may contribute to biological safety," *Plant Science* 153:107-112 (2000).
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Office Action dated Aug. 2, 2013, in Colombian Patent Application No. 12152898.
Office Action dated Aug. 28, 2013, in Chinese Patent Application No. 201180012795.2.
Office Action dated Feb. 21, 2014, in Colombian Patent Application No. 12152898.
Office Action dated Feb. 24, 2014, in Eurasian Patent Application No. 201201264.
Office Action dated Jul. 23, 2015, in Ukrainian Patent Application No. 201211548.
Office Action dated Apr. 13, 2016, in Chinese Patent Application No. 201280053985.3.
Office Action dated Oct. 5, 2015, in Eurasian Patent Application No. 201201264/28.
Patent Examination Report No. 1 dated Feb. 8, 2016, in Australian Patent Application No. 2014262189.
Patent Examination Report No. 1 dated Nov. 11, 2013, in Australian Patent Application No. 2011224570.
Promoter Prediction for SEQ ID No. 1702 from 13/612929/MK/, Promoter 2.0 Prediction Results, pp. 1-4 (2016).
Salanenka et al., "Seedcoat Permeability: Uptake and Post-germination Transport of Applied Model Tracer Compounds," *HortScience*, 46(4):622-626 (2011).
Scott et al., Botanical Insecticides for Controlling Agricultural Pests: Piperamides and the Colorado Potato Beetle *Leptinotarsa decemlineata* Say (Coleoptera: Chrysomelidae), *Archives of Insect Biocheinisny and Physiology*, 54:212-225 (2003).
Second Office Action dated Mar. 4, 2016, in Chinese Patent Application No. 201280054820.8.
Second Office Action dated Feb. 25, 2016, in Chinese Patent Application No. 201280054179.8.
Shintani et al., "Antisense Expression and Overexpression of Biotin Carboxylase in Tobacco Leaves," *Plant Physiol.*, 114:881-886 (1997).
Tsugawa et al., "Efficient transformation of rice protoplasts mediated by a synthetic polycationic amino polymer," *Theor Appl Genet*, 97:1019-1026 (1998).
Wang et al., "Foliar uptake of pesticides—Present status and future challenge," ScienceDirect, 87:1-8 (2007).
Written Opinion dated Apr. 7, 2016, in Singapore Patent Application No. 201206152-9.
Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus—elicited suppression of a 35S promoter-regulated transgene," Nature Biotechnology, 18:995-999 (2000).
Andersen et al., "Delivery of siRNA from lyophilized polymeric surfaces," Biomaterials, 29:506-512 (2008).
Anonymous, "A handbook for high-level expression and purification of 6xHis-tagged proteins," The QiaExpressionist, (2003).
Artymovich, "Using RNA interference to increase crop yield and decrease pest damage," MMG 445 Basic Biotech., 5(1):7-12 (2009).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Balibrea et al., "Extracellular Invertase is an Essential Component of Cytokinin-Mediated Delay of Senescence," The Plant Cell, 16(5):1276-1287 (2004).
Bart et al., "A novel system for gene silencing using siRNAs in rice leaf and stem-derived protoplasts," Plant Methods, 2(13):1-9 (2006).
Basu et al., "Weed genomics: new tools to understand weed biology," TRENDS in Plant Science, 9(8):391-398 (2004).

(56) References Cited

OTHER PUBLICATIONS

Busch et al., "RNAi for discovery of novel crop protection products," Pflanzenschutz-Nachrichten Bayer, 58(1):34-50 (2005).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jun. 26, 2015, in European Patent Application No. 11 753 916.3.
Concise Descriptions of Relevance filed by a third party on Nov. 29, 2012, in U.S. Appl. No. 13/042,856.
Dalakouras et al., "Induction of Silencing in Plants by High-Pressure Spraying of In vitro-Synthesized Small RNAs," Frontiers in Plant Science, 7(1327):1-5 (2016).
Dawson et al., "cDNA cloning of the complete genome of tobacco mosaic virus and production of infectious transcripts," Proc. Natl. Acad. Sci, USA, 83:1832-1836 (1986).
Extended European Search Report dated Sep. 29, 2016, in European Patent Application No. 14778840.0.
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2016, in U.S. Appl. No. 13/583,302.
Final Office Action dated Nov. 19, 2015, in U.S. Appl. No. 13/612,941.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Fukunaga et al., "dsRNA with 5' overhangs v contributes to endogenous and antiviral RNA silencing pathways in plants," The EMBO Journal, 28(5):545-555 (2009).
Further Examination Report dated May 16, 2014, in New Zealand Patent Application No. 601784.
Gan et al., "Inhibition of Leaf Senescence by Autoregulated Production of Cytokinin," Science, 270:1986-1988.
Gao et al., "Nonviral Methods for siRNA Delivery," Molecular Pharmaceutics, 6(3):651-658 (2008).
GenBank Accession No. AY545657.1 (2004).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. U87257.1, "Daucus carota 4-hydroxyphenylpyruvate dioxygenase mRNA, complete cds" (1997).
GenBank Accession No. XM_014456745.1, PREDICTED: Myotis lucifugus ribonucleoprotein, PTB-binding 2 (RAVER2), transcript variant X3, mRNA,: (2015).
GenEmbl Accession No. FJ861243 (2010).
Gossamer Threads, Compendium of Herbicide Adjuvants: Organo-Silicone Surfactant, p. 1-4 (1998).
Hajirezaei et al., "Impact of elevated cytosolic and apoplastic invertase activity on carbon metabolism during potato tuber development," Journal of Experimental Botany, 51:439-445 (2000).
Holtra et al., "Assessment of the Physiological Condition of Salvinia Natans L. Exposed to Copper(II) Ions," Environ. Protect. Eng., 41:147-158 (2015).
International Preliminary Report on Patentability dated Sep. 11, 2012, in International Application No. PCT/US2011/027528.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International. Search Report and the Written Opinion dated Feb. 27, 2013, in International Application No. PCT/US2012/054980.
International Search Report and the Written Opinion dated May 10, 2011, in International Application. No. PCT/US2011/027528.
International Search Report dated Mar. 12, 2013, in International Application No. PCT/US2012/054789.
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Kaloumenos et al., "Identification of a Johnsongrass (Sorghum halepense) Biotype Resistant to ACCase-Inhibiting Herbicides in Northern Greece," Weed Technol, 23:470-476 (2009).
Kambiranda et al., "Relationship Between Acid Invertase Activity and Sugar Content in Grape Species," Journal of Food Biochemistry, 35:1646-1652 (2011).
Kim et al., "Optimization of Conditions for Transient Agrobacterium-Mediated Gene Expression Assays in Arabidopsis," Plant Cell Reports, 28:1159-1167 (2009).
Kirkwood, "Herbicides and Plants," Botanical Journal of Scotland, 46(3):447-462 (1993).
Liu et al., "Identification and Application of a Rice Senescence-Associated Promoter," Plant Physiology, 153:1239-1249 (2010).
Liu, "Influence of Sugars on the Foliar Uptake of Bentazone and Glyphosate," New Zealand Plant Protection, 55:159-162 (2002).
Luque et al., "Water Permeability of Isolated Cuticular Membranes: A Structural Analysis," Archives of Biochemistry and Biophysics, 317(2):417-422 (1995).
Mora et al., "How Many Species Are There on Earth and in the Ocean?," PLOS Biol., 9(8):e100127, p. 1-8 (2011).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.

(56) References Cited

OTHER PUBLICATIONS

Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Mar. 1, 2016, in U.S. Appl. No. 13/612,954.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Aug. 25, 2016, in Eurasian Patent Application No. 201201264.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Jul. 18, 2016, in Indonesian Patent Application No. W00201203610.
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Nov. 15, 2016, in Mexican Patent Application. No. MX/a/2014/003068.
Office Action dated Sep. 5, 2016, in Ukrainian Patent Application No. a 2014 03846.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Promoter Prediction for SEQ ID No. 4 from U.S. Appl. No. 13/612,995/MK/, Promoter 2.0 Prediction Results, pp. 1-3 (2016).
Promoter Prediction for SEQ ID No. 7 from U.S. Appl. No. 13/612,936/MK/, Promoter 2.0 Prediction Results, pp. 1-2 (2016).
Promoter Prediction for SEQ ID No. 8 from U.S. Appl. No. 13/612,925/MK/, Promoter 2.0 Prediction Results, pp. 1-6 (2016).
Regalado, "The Next Great GMO Debate," MIT Technology Review,pp. 1-19 (2015) <https://www.technologyreview.com/s/540136/the-next-great-gmo-debate/>.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Ruan et al., "Suppression of Sucrose Synthase Gene Expression Represses Cotton Fiber Cell Initiation, Elongation, and Seed Development," The Plant Cell, 15:952-964 (2003).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Second Chinese Office Action dated Jun. 10, 2014, in Chinese Patent Application No. 201180012795.2.
Shaoquan, "The action target of herbicide and the innovation of a new variety," Chemical Industry Press, pp. 23-24 (2001).
Showalter, "Structure and Function of Plant Cell Wall Proteins," The Plant Cell, 5:9-23 (1993).
Song et al., "Herbicide," New Heterocyclic Pesticide, Chemical Industry Press, 354-356 (2011).
Stevens, "Organosilicone Surfactants as Adjuvants for Agrochemicals," Journal of Pesticide Science, 38:103-122 (1993).
Tang et al., "Efficient delivery of small interfering RNA to plant cells by a nanosecond pulsed laser-induced stress wave for post-transcriptional gene silencing," Plant Science, 171:375-381 (2006).
Temple et al., "Can glutamine synthetase activity levels be modulated in transgenic plants by the use of recombinant DNA technology?" Transgenic Plants and Plant Biochemistry, 22(4):915-920 (1994).
Tenllado et al., "Double-Stranded RNA-Mediated Interference with Plant Virus Infection," Journal of Virology, 75(24):12288-12297 (2001).
Thomas et al., "Size constraints for targeting post-transcriptional gene silencing and for RNA-directed methylation in Nicotiana benthamiana using a potato virus X vector," The Plant Journal, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany.
Unniraman et al., "Conserved Economics of Transcription Termination in Eubacteria," Nucleic Acids Research, 30(3):675-684 (2002).
Voinnet et al., "Systemic Spread of Sequence-Specific Transgene RNA Degradation in Plants Is Initiated by Localized Introduction of Ectopic Promoterless DNA," Cell, 95:177-187 (1998).
Widholm et al., "Glyphosate selection of gene amplification in suspension cultures of 3 plant species," Phyisologia Plantarum, 112:540-545 (2001).

(56) References Cited

OTHER PUBLICATIONS

Wiesman et al., "Novel cationic vesicle platform derived from vernonia oil for efficient delivery of DNA through plant cuticle membranes," Journal of Biotechnology, 130:85-94 (2007).
Wild Carrot, Noxious Weed Control Board (NWCB) of Washington State (2010) <www.nwcb.wa.gov/detail.asp?weed=46>.
Written Opinion dated Mar. 6, 2017, in Singaporean Patent Application No. 2012061529.
Zhang et al., "Chapter 10: New Characteristics of Pesticide Research & Development," New Progress of the world agriculture chemicals, p. 209 (2010).
Anonymous, "Resistant Weeds Spur Research into New Technologies," Grains Research & Development Corporation, 2013.
Ascencio-Ibanez et al., "DNA abrasion onto plants is an effective method for geminivirus infection and virus-induced gene silencing," Journal of Virological Methods, 142:198-203 (2007).
Bauer et al., "The major protein import receptor of plastids is essential for chloroplast biogenesis," Nature, 403:203-207 (2000).
Baum et al., "Progress Towards RNAi-Mediated Insect Pest Management" Advances in Insect Physiology, 47:249-295 (2014).
Bedell et al., "Sorghum Genome Sequencing by Methylation Filtration," PLOS Biology, 3(1):E13/104-115 (2005).
Burgos et al., "Review: Confirmation of Resistance to Herbicides and Evaluation of Resistance Levels," Weed Science, 61 (1):4-20 (2013).
Chang et al., "Dual-target gene silencing by using long, synthetic siRNA duplexes without triggering antiviral responses," Molecules and Cells, 27(6) 689-695 (2009).
Chen et al., "Exploring MicroRNA-Like Small RNAs in the Filamentous Fungus Fusarium oxysporum," PLOS One, 9(8):e104956:1-10 (2014).
Christiaens et al., "The challenge of RNAi-mediated control of hemipterans," Current Opinion in Insect Science, 6:15-21 (2014).
Constan et al., "An outer envelope membrane component of the plastid protein import apparatus plays an essential role in *Arabidopsis*," The Plant Journal, 38:93-106 (2004).
Communication Pursuant to Article 94(3) EPC dated Sep. 5, 2018, in European Patent Application No. 17152830.0.
Database EMBL XP-002781749(BG442539) dated Mar. 20, 2001.
Di Stilio et al., "Virus-Induced Gene Silencing as a Tool for Comparative Functional Studies in Thalictrum," PLoS One, 5(8):e12064 (2010).
European Partial Search Report dated Jun. 29, 2018, in European Patent Application No. 18157745.3.
European Search Report dated Sep. 7, 2017, in European Patent Application No. 17152830.0.
Examination Report dated Mar. 1, 2018, in Australian Patent Application No. 2013264742.
Extended European Search Report dated Nov. 7, 2017, in European Patent Application No. 15811092.4.
Extended European Search Report dated Nov. 8, 2017, in European Patent Application No. 15737282.2.
Extended European Search Report dated Sep. 28, 2018, in European Patent Application No. 16740770.9.
Extended European Search Report dated Apr. 13, 2018, in European Patent Application No. 15812530.0.
Extended European Search Report dated Mar. 15, 2018, in European Patent Application No. 17181861.0.
Fassler, BLAST Glossary, National Center for Biotechnology Information (2011).
GenBank Accession No. EF143582 (2007).
Eamens et al., "RNA Silencing in Plants: Yesterday, Today, and Tomorrow," Plant Physiology, 147(2):456-468 (2008).
Eudes et al., "Cell-penetrating peptides," Plant Signaling & Behavior, 3(8):549-5550 (2008).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Friedberg, "Automated protein function prediction—the genomic challenge," Briefings in Bioinformatics, 7(3):225-242 (2006).

Funke et al., "Molecular basis for herbicide resistance in Roundup Ready crops," PNAS, 103:13010-13015 (2006).
Gaskin et al., "Novel organosillicone adjuvants to reduce agrochemical spray volumes on row crops," New Zealand Plant Protection, 53:350-354 (2000).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Hess, "Surfactants and Additives," 1999 Proceedings of the California Weed Science Society, 51:156-172 (1999).
Hoermann et al., "Tic32, as Essential Component in Chloroplast Biogenesis," The Journal of Biological Chemistry, 279(33):34756-34762 (2004).
Hu et al., "High efficiency transport of quantum dots into plant roots with the aid of silwet L-77," Plant Physiology and Biochemistry, 48:703-709 (2010).
Huang et al., "In Vivo Analyses of the Roles of Essential Omp85-Related Proteins in the Chloroplast Outer Envelope Membrane," Plant Physiol., 157:147-159 (2011).
Inaba et al., "*Arabidopsis* Tic110 Is Essential for the Assembly and Function of the Protein Import Machinery of Plastids," The Plant Cell, 17:1482-1496 (2005).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Kikkert et al., "Stable Transformation of Plant Cells by Particle Bombardment/Biolistics," Methods in Molecular Biology, 286:61-78 (2005).
Kovacheva et al., "Further in vivo studies on the role of the molecular chaperone, Hsp93, in plastid protein import," The Plant Journal, 50:364-379 (2007).
Kovacheva et al., "In vivo studies on the roles of Tic100, Tic40 and Hsp93 during chloroplast protein import," The Plant Journal, 41:412-428 (2005).
Li et al., "A Simplified Seed Transformation Method for Obtaining Transgenic *Brassica napus* Plants," Agricultural Sciences in China, 8(6):658-663 (2009).
Li et al., "Long dsRNA but not siRNA initiates RNAi in western corn rootworm larvae and adults," Journal of Applied Entomology, 139(6):432-445 (2015).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
Liu, "Calmodulin and Cell Cycle," Foreign Medical Sciences Section of Pathophysiology and Clinical Medicine, 18(4):322-324 (1998).
Liu, "The Transformation of Nucleic Acid Degradants in Plants," China Organic Fertilizers, Agriculture Press, ISBN: 7-1091634 (with English translation) (1991).
Lodish et al., Molecular Cell Biology, Fourth Edition, p. 210 (2000).
McGinnis, "RNAi for functional genomics in plants," Brief Funct Genomics, 9(2):111-7 (2010).
Non-Final Office Action dated Mar. 21, 2018, in U.S. Appl. No. 13/619,980.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.

(56) References Cited

OTHER PUBLICATIONS

Office Action dated Dec. 5, 2017, in Japanese Patent Application No. 2016-502033.
Office Action dated Feb. 21, 2018, in Mexican Patent Application No. MX/a/2015/012632 (with English translation).
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated Mar. 8, 2018 (with English translation), in Chilean Patent Application No. 201403192.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 6, 2017, in Chinese Patent Application No. 2014800154012 (with English translation).
Partial European Search Report dated Dec. 6, 2017, in European Patent Application No. 17181861.0.
Partial Supplementary European Search Report dated Jan. 11, 2018, in European Patent Application No. 15812530.0.
Patent Examination Report No. 1 dated Jun. 8, 2017, in Australian Patent Application No. 2012308686.
Powles et al., "Evolution in Action: Plants Resistant to Herbicides," Annual Review of Plant Biology, 61(1):317-347.
Qichuan et al., Seed Science, China Agriculture Press, pp. 101-103, Tables 2-37 (2001).
Ralcoczy-Trojanowska, "Alternative Methods of Plant Transformation—a short review," Cellular & Molecular Biology Letters, 7:849-858 (2002).
Richardson et al., "Targeting and assembly of components of the TOC protein import complex at the chloroplast outer envelope membrane," Frontiers in Plant Science, 5:1-14 (2014).
Small, "RNAi for revealing and engineering plant gene functions," Current Opinion in Biotechnology, 18:148-153 (2007).
Search Report dated Jul. 24, 2017, in Chinese Patent Application No. 201480014392.5 (with English translation).
Search Report dated Oct. 20, 2017, in Chinese Patent Application No. 201380039346.6.
Statement of Grounds and Particulars dated Sep. 1, 2017, in Australian Patent No. 2014262189.
Summons to Attend Oral Proceedings Pursuant to Rule 115(1) EPC, dated Aug. 7, 2017, in European Patent Application No. 12832160.1.
Stevens, "Formulation of Sprays to Improve the Efficacy of Foliar Fertilisers," New Zealand Journal of Forestry Science, 24(1):27-34 (1994).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Teng et al., "Tic21 Is an Essential Translocon Component for Protein Translocation across the Chloroplast Inner Envelope Membrane," The Plant Cell, 18:2247-2257 (2006).
Trucco et al., "*Amaranthus hybridus* can be pollinated frequently by *A. tuberculatus* under filed conditions," Heredity, 94:64-70 (2005).
Ulrich et al., "Large scale RNAi screen in Tribolium reveals novel target genes for pest control and the proteasome as prime target," BMC genomics, 16(1):671 (2015).
Voinnet, "Origin, Biogenesis, and Activity of Plant MicroRNAs," Cell, 136:669-687 (2009).
Wool et al., "Structure and evolution of mammalian ribosomal proteins," Biochem. Cell Biol., 73:933-947 (1995).
Xu et al., "Characterization and Functional Analysis of the Calmodulin-Binding Domain of Rac1 GTPase," PLoS One, 7(8):e42975 (2012).
Zaimin et al., Chapter III Seeds and Seedlings, Botany, Northwest A&F University Press, pp. 87-92 (2009).
Zhao et al., "Vegetable Standardized Production Technology," Hangzhou: Zhejiang Science and Technology Press, p. 19 (2008).
Zhang, "Artificial trans-acting small interfering RNA: a tool for plant biology study and crop improvements," Planta, 239:1139-1146 (2014).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zotti et al., "RNAi technology for insect management and protection of beneficial insects from diseases: lessons, challenges and risk assessments," Neotropical Entomology, 44(3):197-213.
Asad et al., "Silicon Carbide Whisker-mediated Plant Transformation," Properties and Applications of Silicon Carbide, pp. 345-358 (2011).
Baker, "Chlorophyll Fluorescence: A Probe of Photosynthesis In Vivo," Annu. Rev. Plant Biol., 59:89-113 (2008).
Baulcombe, "RNA silencing in plants," Nature, 431:356-363 (2004).
Belhadj et al., "Methyl Jasmonate Induces Defense Responses in Grapevine and Triggers Protection against Erysiphe necator," J. Agric Food Chem., 54:9119-9125 (2006).
Burleigh, "Relative quantitative RT-PCR to study the expression of plant nutrient transporters in arbuscular mycorrhizas," Plant Science, 160:899-904 (2001).
Chang et al., "Dual-target gene silencing by using long, sythetic siRNA duplexes without triggering antiviral responses," Molecules and Cells, 27(6)689-695 (2009).
Cheng et al., "Transient Expression of Minimum Linear Gene Cassettes in Onion Epidermal Cells via Direct Transformation," Appl Biochem Biotechnol, 159:739-749 (2009).
Cong et al., "Multiplex Genome Engineering Using CRISPR/Cas Systems," Science, 339:819-823 (2013).
Danka et al., "Field Test of Resistance to Acarapis woodi (Acari: Tarsonemidae) and of Colony Production by Four Stocks of Honey Bees (*Hymenoptera*: Apidae)" Journal of Economic Entomology, 88(3):584-591 (1995).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Delye et al., "PCR-based detection of resistance to acetyl-CoA carboxylase-inhibiting herbicides in black-grass (*Alopecurus myosuroides* Huds) and ryegrass (*Lolium rigidum* Gaud)," Pest Management Science, 58:474-478 (2002).
Delye et al., "Variation in the gene encoding acetolactate-synthase in *Lolium* species and proactive detection of mutant, herbicide-resistant alleles," Weed Research, 49:326-336 (2009).
Desveaux et al., "PBF-2 Is a Novel Single-Stranded DNA Binding Factor Implicated in PR-10a Gene Activation in Potato," The Plant Cell, 12:1477-1489 (2000).
Dietzgen et al., "Transgenic gene silencing strategies for virus control," Australasian Plant Pathology, 35:605-618 (2006).
Dilpreet et al., "Glyphosate Rsistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).

(56) References Cited

OTHER PUBLICATIONS

Drobyazko R.V. "Reliable and environmentally friendly insecticide," Protection and quarantine of plants, 2012 (pp. 52, 53) (in Russian).
Duhoux et al., "Reference Genes to Study Herbicide Stress Response in Lolium sp.: Up-Regulation of P3450 Genes in Plants Resistant to Acetolactate-Synthase Inhibitors," PLOS One, 8(5):e63576 (2013).
Egli et al., "A Maize Acetyl-Coenzyme A Carboxylase cDNA Sequence," Plant Physiol., 108: 1299-1300 (1995).
Extended European Search Report dated Dec. 19, 2018, in European Patent Application No. 16804395.8.
Extended European Search Report dated Nov. 16, 2018, in European Patent Application No. 18182238.8.
Extended European Search Report dated Nov. 21, 2018, in European Patent Application No. 18175809.5.
Gallie et al., "Identification of the motifs within the tobacco mosaic virus 5'-leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gao et al., "DNA-guided genome editing using the Natronobacterium gregoryi Argonaute," Nature Biotechnology, 34(7):768-773 (2016).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
Gilmer et al., "Latent Viruses of Apple I. Detection with Woody Indicators," Plant Pathology, 1(10):1-9 (1971).
Guttieri et al., "DNA Sequence Variation in Domain A of the Acetolactate Synthase Genes of Herbicide-Resistant and -Susceptible Weed Biotypes," Weed Science, 40:670-679 (1992).
Hagio, "Chapter 25: Direct Gene Transfer into Plant Mature Seeds via Electroporation After Vacuum Treatment," Electroporation and Sonoporation in Developmental Biology, p. 285-293 (2009).
Hörmann et al., "Tic32, as Essential Component in Chloroplast Biogenesis," The Journal of Biological Chemistry, 279(33):34756-34762 (2004).
Horsch et al., "Inheritance of Functional Foreign Genes in Plants ," Science, 223:496-498 (1984).
Hsu et al., "DNA targeting specificity of RNA-guided Cas9 nucleases," Nature Biotechnology, 31:827-832 (2013).
Huggett et al., "Real-time RT-PCR normalisation; strategies and considerations," Genes and Immunity, 6:279-284 (2005).
International Search Report dated Oct. 13, 2016, in International Patent Application No. PCT/US2016/35500.
Jarvis et al, "An *Arabidopsis* mutant defective in the plastid general protein import apparatus," Science, 282:100-103 (1998).
Jiang et al., Chapter III Seeds and Seedlings, Botany, Northwest A&F University Press, pp. 87-92 (2009).
Khanbekova et al., "The defeat of the honey bee *Apis melifera* caucasica Gorb. by viruses and parasites, and condition of bee colonies in different ecogeographical conditions of Greater Caucasus, Agricultural Biology. 2013 (p. 43) (in Russian).
Kim et al., "Synthesis and characterization of mannosylated pegylated polyethylenimine as a carrier for siRNA," International Journal of Pharmaceutics, 427:123-133 (2012).
Kirkwood, "Recent developments in our understanding of the plant cuticle as a barrier to the foliar uptake of pesticides," Pestic Sci, 55:69-77 (1999).
Kumar et al., "Sequencing, De Novo Assembly and Annotation of the Colorado Potato Beetle, *Leptinotarsa decemlineata*, Transcriptome," PLoS One, 9(1):e86012 (2014).
Li et at., "Long dsRNA but not siRNA initiates RNAi in western corn rootworm larvae and adults," Journal of Applied Entomology, 139(6):432-445 (2015).
Liu, "Confocal laser scanning microscopy—an attractive tool for studying the uptake of xenobiotics into plant foliage," Journal of Microscopy, 213(Pt 2):87-93 (2004).
Liu, "The Transformation of Nucleic Acid Degradants in Plants," China Organic Fertilizers, Agriculture Press, ISBN: 7-1091634 (1991) (with English translation).
Lucas et al., "Plasmodesmata—bridging the gap between neighboring plant cells," Trends in Cell Biology, 19:495-503 (2009).
Masoud, "Constitutive expression of an inducible β-1,3-glucanase in alfalfa reduces disease severity caused by the oomycete pathogen *Phytophthora megasperma* f. sp *medicaginis* . . . ," Trans Res, 5:313-323 (1996).
Misawa, "Expression of an Erwinia phytoene desaturase gene not only confers multiple resistance to herbicides interfering with carotenoid biosynthesis but also alters xanthophyll metabolism . . . ," The Plant Jrnl, 6(4):481-489 (1994).
Misawa, "Functional expression of the Erwinia uredovora carotenoid biosynthesis gene crtI in transgenic plants showing an increase of β-carotene biosynthesis activity and resistance . . . ," The Plant Jrnl, 4(5):833-840 (1993).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Nemeth, "Virus, mycoplasma and rickettsia diseases of fruit trees," Martinus Nijhoff Publishers, 197-204 (1986).
N-TER Nanoparticle siRNA, Sigma Aldrich TM website, Web. Nov. 20, 2018 <https://www.sigmaaldrich.com/life-science/custom-oligos/sirna-oligos/n-ter-nanoparticle.html>.
Office Action dated Sep. 20, 2018, in Chilean Patent Application No. 201601440 (with English translation).
Paddison et al., "Stable suppression of gene expression by RNAi in mammalian cells," Proc. Natl Acad. Sci. USA, 99(3):1443-1448 (2002).
Partial European Search Report dated Jun. 29, 2018, in European Patent Application No. 18157745.3.
Partial Supplementary European Search Report dated Jan. 11, 2018, in European Patent Application No. 15812530.2.
Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Qi et al., "RNA processing enables predictable programming of gene expression," Nature Biotechnology, 30:1002-1007 (2012).
Reverdatto et al., "A Multisubunit Acetyl Coenzyme A Carboxylase from Soybean," Plant Physiol., 119: 961-978 (1999).
Riar et al., "Glyphosate Resistance in a Johnsongrass (*Sorghum halepense*) Biotype from Arkansas," Weed Science, 59:299-304 (2011).
Sammataro et al., "Some Volatile Plant Oils as Potential Control Agents for *Varroa* Mites (Acari: Varroidae) in Honey Bee Colonies (Hymenoptera: Apidae)," American Bee Journal, 138(9):681-685 (1998).
Schönherr et al., "Size selectivity of aqueous pores in astomatous cuticular membranes isolated from Populus canescens (Aiton) Sm. Leaves," Planta, 219:405-411 (2004).
Simeoni et al., "Insight into the mechanism of the peptide-based gene delivery system MPG: implications for delivery of siRNA into mammalian cells," Nucleic Acids Research, 31(11):2717-2724 (2003).
Swarts et al., "Argonaute of the archaeon Pyrococcus furiosus is a DNA-guided nuclease that targets cognate DNA," Nucleic Acid Res., 43(10):5120-5129 (2015).
Swarts et al., "DNA-guided DNA interference by a prokaryotic Argonaute," Nature, 507(7491):258-61 (2014).
Tenllado et al., "Crude extracts of bacterially expressed dsRNA can be used to protect plants against virus infections," BMC Biotechnology, 3:1-11 (2003).
Tice, "Selecting the right compounds for screening: does Lipinski's Rule of 5 for pharmaceuticals apply to agrochemicals?" Pest Management Science, 57(1):3-16 (2001).
Tomlinson, "Evidence that the hexose-to-sucrose ratio does not control the switch to storage product accumulation in oilseeds: analysis of tobacco seed development and effects . . . ," Jrnl of Exper Bot, 55(406):2291-2303 (2004).
Toriyama et al., "Transgenic Rice Plants After Direct Gene Transfer Into Protoplasts," Bio/Technology, 6:1072-1074 (1988).
Townsend et al., "High frequency modification of plant genes using engineered zinc finger nucleases," Nature, 459:442-445 (2009).

(56) References Cited

OTHER PUBLICATIONS

TransIT-TKO® Transfection Reagent, Frequently Asked Questions, Web. 2019 <https://www.mirusbio.com/tech-resources/faqs/transit-tko-faqs>.

Van der Meer et al., "Promoted analysis of the chalcone synthase (chs A) gene of Petunia hybrid: a 67 bp promoter region directs flower-specific expression," Plant Mol. Biol., 15:95-109 (1990).

Vila-Aiub et al., "Glyphosate resistance in perennial *Sorghum halepense* (Johnsongrass), endowed by reduced glyphosate translocation and leaf uptake," Pest Manag Sci, 68:430-436 (2012).

Wang et al., "Principle and technology of genetic engineering in plants," in Plant genetic engineering principles and techniques, Beijing: Science Press, pp. 313-315 (1998).

Watson et al., "RNA silencing platforms in plants," FEBS Letters, 579:5982-5987 (2005).

Yan et al., Seed Science, China Agriculture Press, pp. 101-103, Tables 2-37 (2001).

Yu et al., "Diversity of Acetyl-Coenzyme A Carboxylase Mutations in Resistant Lolium Populations: Evaluation Using Clethodim," Plant Physiology, 145:547-558 (2007).

Yu et al., "Glyphosate, paraquat and ACCase multiple herbicide resistance evolved in a Lolium rigidum biotype," Planta, 225:499-513 (2007).

Zabkiewicz, "Adjuvants and herbicidal efficacy—present status and future prospects," Weed Research, 40:139-149 (2000).

Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).

Zhang et al., "Progress in research of honey bee mite *Varro destructor*," Journal of Environmental Entomology, 34(3):345-353 (2012).

Zhang, Chapter 10: New Characteristics of Pesticide Research & Development, p. 209 (2010).

Zhao et al., "Ps0r1, a potential target for RNA interference based pest management," Insect Molecular Biology, 20(1):97-104 (2011).

Zhao et al., "Vegetable Statdardized Production Technology," Hangzhou: Zhejiang Science and Technology Press, p. 19 (2008).

Zidack et al., "Promotion of Bacterial Infection of Leaves by an Organosilicone Surfactant: Implications for Biological Weed Control," Biological Control, 2:111-117 (1992).

Zipperian et al., "Silicon Carbide Abrasive Grinding," Quality Matters Newsletter, PACE Technologies 1(2):1-3 (2002).

Zotti et al., "RNAi technology for insect management and protection of beneficial insects from diseases: lessons, challenges and risk assessments," Neotropical Entomology, 44(3):197-213 (2015).

\* cited by examiner

FIG. 1C  *Nicotiana benthamiana* protoplast Taqman data

3' initiator overhang      5' blocker overhang

Directional dsRNA Trigger Molecule

Non-directional dsRNA trigger

* Used at 50pmol, rather than 200 pmol for all other triggers shown

Note: PDS expression is low in these protoplasts

| Probe | GOI | Trigger ID | % KD |
|---|---|---|---|
| 5' | SlEPSPS | SEQ11/SEQ62 | -37.1 |
| 5' | SlPDS | SEQ11/SEQ62 | -14.4 |
| 3' | SlEPSPS | SEQ11/SEQ62 | ND |
| 3' | SlPDS | SEQ11/SEQ62 | ND |
| 5' | SlEPSPS | SEQ12/SEQ63 | -46.3 |
| 5' | SlPDS | SEQ12/SEQ63 | -17.4 |
| 3' | SlEPSPS | SEQ12/SEQ63 | -29.7 |
| 3' | SlPDS | SEQ12/SEQ63 | -29.3 |

A= templated nucleotide
A= non-templated nucleotide

SEQUENCE LISTING

<160> NUMBER OF SEQ ID NOS: 92

<210> SEQ ID NO 1
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ccauugacgu gaacaugaac aaaaugccag auguggccau gacuc                          45

<210> SEQ ID NO 2
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugccauugac gugaacauga acaaaaugcc agauguggcc augac                          45

<210> SEQ ID NO 3
<211> LENGTH: 45

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cgugccauug acgugaacau gaacaaaaug ccagaugugg ccaug            45

<210> SEQ ID NO 4
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugcgugcca uugacgugaa caugaacaaa augccagaug uggcc            45

<210> SEQ ID NO 5
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aacauuugcg ugccauugac gugaacauga acaaaaugcc agaug            45

<210> SEQ ID NO 6
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
aaugaaacau uugcgugcca uugacgugaa caugaacaaa augcc            45

<210> SEQ ID NO 7
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggaaggaac auucaaugaa agcaugaaca aaaugccaga ggccac           46

<210> SEQ ID NO 8
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
guaagggugg gcaaaaauaa aaagugauua cuccgccgaa aaggccac         48

<210> SEQ ID NO 9
<211> LENGTH: 48
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 9
gucaagaaaa ccggucuuaa aaaguaucuu cgaggccaug gaggccac                48

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 10
gcgggcuauu gaugucaaca ugaacaaaau gccugaugua gcaaugac                48

<210> SEQ ID NO 11
<211> LENGTH: 46
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
gggaaggaac auucaaugaa agcaugaaca aaaugccaga ggccac                  46

<210> SEQ ID NO 12
<211> LENGTH: 46
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12
gcaugaacaa aaugccagaa agggaaggaa cauucaauga ggccac                  46

<210> SEQ ID NO 13
<211> LENGTH: 50
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13
gguguuuauu gccaugucaa aaacugguuu guuggcuaaa gcuaagccac              50

<210> SEQ ID NO 14
<211> LENGTH: 52
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
cugguuuguu ggcuaaagcu aaaaaggugu uuauugccau gucaaaggcc ac           52

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcgtgctatc gacgtcaaca tgaacaaaat gccagatgtt gctatgac                48

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgctatcgac gtcaacatga a                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgtgctatcg acgtcaacat g                                             21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctatcgacgt caacatgaa                                                19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgctatcgac gtcaacatg                                                19

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caacatgaac aaaatgccag atgttgctat gac                                33

<210> SEQ ID NO 21
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 21
aacaaaatgc cagatgttgc tatg                                            24

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatgccagat gttgctatga c                                               21

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgtgctatc gacgtcaaca tgaaca                                          26

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtgctatcga cgtcaacatg aaca                                            24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgtgctatc gacgtcaaca tgaa                                            24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgctatcgac gtcaacatga aca                                             23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 27
cgtgctatcg acgtcaacat gaa                                          23

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctatcgacg tcaaca                                                  16

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtgctatcga cgtcaacatg aa                                           22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctatcgacgt caacatgaac a                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgctatcgac gtcaacatga a                                            21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aaatgccaga tgttgctatg ac                                           22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caaaatgcca gatgttgcta tg                                              22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgacgtcaac atgaacaaaa tgcc                                            24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atcgacgtca acatgaacaa aatg                                            24

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcaacatgaa caaaatgcca gatgttgcta tg                                   32

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgtcaacatg aacaaaatgc caga                                            24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctatcgacgt caacatgaac aaaa                                            24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 39
tgctatcgac gtcaacatga acaa                                          24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtgctatcga cgtcaacatg aa                                            22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcgtgctatc gacgtcaaca tg                                            22

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcgacgtcaa catgaaca                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tatcgacgtc aacatgaa                                                 18

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgctatcgac gtcaacatga acaa                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```

```
cgtgctatcg acgtcaacat gaac                                          24

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
caaaatgcca gatgttgcta tga                                           23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aacaaaatgc cagatgttgc tat                                           23

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gctatcgacg tcaacatgaa                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtgctatcga cgtcaacatg                                               20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caaaatgcca gatgttgcta tg                                            22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
```
aacaaaatgc cagatgttgc ta                                         22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctatcgacgt caacatgaac                                            20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgctatcgac gtcaacatga                                            20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgccagatgt tgctatgac                                             19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atgccagatg ttgctatga                                             19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaatgccaga tgttgctatg                                            20

<210> SEQ ID NO 57
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gucauggcca caucuggcau uuuguucaug uucacgucaa uggca                45

<210> SEQ ID NO 58
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gcgcgguggc cucuggcauu uuguucaugc uuucauugaa uguccuucc caa            53

<210> SEQ ID NO 59
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
gcgcgguggc cuuuucggcg gaguaaucac uuuuuauuuu gcccacccuu acaa          54

<210> SEQ ID NO 60
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gcgcgguggc cuccauggcc ucgaagauac uuuuuaagac cgguuucuu gacua          55

<210> SEQ ID NO 61
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gucauugcua caucaggcau uuuguucaug uugacaucaa uagcccgc                 48

<210> SEQ ID NO 62
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gcgcgguggc cucuggcauu uuguucaugc uuucauugaa uguccuucc caa            53

<210> SEQ ID NO 63
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gcgcgguggc cucauugaau guccuuccc uuucggcau uuuguucaug caa             53

<210> SEQ ID NO 64
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gcgcgguggc uuagcuuuag ccaacaaacc aguuuuugac auggcaauaa acaccuc        57

<210> SEQ ID NO 65
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ggccgaattc agtaaaggag aagaactttt cactggagtt gtcccaattc ttgttgaatt     60
agatggtgat gttaatgggt acaaattttc tgtcagtgga gagggtgaag gtgatgcaac    120
atac                                                                 124

<210> SEQ ID NO 66
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gagccugguc uucuugcuaa aaaggugaug uuaaugggua caaaggccac                50

<210> SEQ ID NO 67
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcgcgguggc cuuuguaccc auuaacauca ccuuuuuagc aagaagacca ggcucgc        57

<210> SEQ ID NO 68
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggugguuuau ugccauguca aaaugcaac gauuuggaau gaaaaggcca c               51

<210> SEQ ID NO 69
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gcgcgguggc cuuucauuc caaaucguug cauuuugac auggcaauaa acaccuc    57

<210> SEQ ID NO 70
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 70
gguguuauac ccaugucaaa aaugcaacga uaaggaauga aaaggccacg cgcgguggcc    60
uuuucauucc uuaucguugc auuuugaca uggguauaaa caccuc    106

<210> SEQ ID NO 71
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 71
gagguguuua uacccauguc aaaaaugcaa cgauaaggaa ugaaaaggcc accgcgcgug    60
gccuuuucau uccuuaucgu ugcauuuuug acaugggguau aacacc    106

<210> SEQ ID NO 72
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gagguguuua uugccauguc aaaaaugcaa cgauuuggaa ugaaaaggcc accgcgc    57

<210> SEQ ID NO 73
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcgcgguggc cuuucauuc caaaucguug cauuuugac auggcaauaa acaccuc    57

<210> SEQ ID NO 74
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gcguuacguc uaagcguccg gcgguccgua gcguauaccg cggacguaac    50

<210> SEQ ID NO 75
<211> LENGTH: 50
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
guuacguccg cgguauacgc uacggaccgc cggacgcuua gacguaacgc                50

<210> SEQ ID NO 76
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ggagauuaca caaacagaa guacuuagcu uccauggaag gcgcuguccu u                51

<210> SEQ ID NO 77
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ggacagcgcc uuccauggaa gcuaaguacu ucguuuugu guaaucucca g                51

<210> SEQ ID NO 78
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
guuguuaaga uggcaaaggc acugcaacga uuuggaauga aaagagcac                 49

<210> SEQ ID NO 79
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gugcucuuuu cauuccaaau cguugcagug ccuuugccau cuuaacaac                 49

<210> SEQ ID NO 80
<211> LENGTH: 5
<212> TYPE: RNA
<213> ORGANISM: Artificial Sequence
<220> FEATURE:
<223> OTHER INFORMATION: Description of Artificial Sequence: Synthetic
      oligonucleotide linker

<400> SEQUENCE: 80 aaaag                                                                 5

<210> SEQ ID NO 81
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gcgcgguggc cuuugacaug gcaauaaaca ccuuuuuagc uuuagccaac aaaccaggc        59

<210> SEQ ID NO 82
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccactgacag aaaatttgta cccattaaca tcaccatcta attcaacaag aattgggaca       60
actccagtga aaagttcttc tcctttactg aattcggcc                             99

<210> SEQ ID NO 83
<211> LENGTH: 46
<212> TYPE: RNA
<213> ORGANISM: Artificial Sequence
<220> FEATURE:
<221> NAME/KEY: misc_RNA
<222> LOCATION: 2..17, 23..38, 43..46
<223> OTHER INFORMATION: Description of Artificial Sequence: Synthetic
      oligonucleotide, n can be a, u, g, or c

<400> SEQUENCE: 83
gnnnnnnnnn nnnnnnnaau agnnnnnnnn nnnnnnnnaa ggnnnn                     46

<210> SEQ ID NO 84
<211> LENGTH: 51
<212> TYPE: RNA
<213> ORGANISM: Artificial Sequence
<220> FEATURE:
<221> NAME/KEY: misc_RNA
<222> LOCATION: 4..7, 12..27, 33..48
<223> OTHER INFORMATION: Description of Artificial Sequence: Synthetic
      oligonucleotide, n can be a, u, g, or c

<400> SEQUENCE: 84
gggnnnnccu unnnnnnnnn nnnnnnnncua uunnnnnnnn nnnnnnnncu a              51

<210> SEQ ID NO 85
<211> LENGTH: 21
<212> TYPE: RNA
<213> ORGANISM: Artificial Sequence
<220> FEATURE:
<221> NAME/KEY: misc_RNA
<222> LOCATION: 2..17
<223> OTHER INFORMATION: Description of Artificial Sequence: Synthetic
      oligonucleotide, n can be a, u, g, or c

<400> SEQUENCE: 85
gnnnnnnnnn nnnnnnnaau a                                                21

<210> SEQ ID NO 86
<211> LENGTH: 21
<212> TYPE: RNA
<213> ORGANISM: Artificial Sequence
<220> FEATURE:
<221> NAME/KEY: misc_RNA
<222> LOCATION: 3..18
<223> OTHER INFORMATION: Description of Artificial Sequence: Synthetic
      oligonucleotide, n can be a, u, g, or c

<400> SEQUENCE: 86
uunnnnnnnn nnnnnnnncu a                                                21

<210> SEQ ID NO 87
<211> LENGTH: 21
<212> TYPE: RNA
<213> ORGANISM: Artificial Sequence
<220> FEATURE:
<221> NAME/KEY: misc_RNA
<222> LOCATION: 2..17
<223> OTHER INFORMATION: Description of Artificial Sequence: Synthetic
      oligonucleotide, n can be a, u, g, or c

<400> SEQUENCE: 87
gnnnnnnnnn nnnnnnnaag g                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
aucaguucuu uuggccagaa u                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ucaguucuuu uggccagaau u                                              21

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aucaguucuu uuggccagaa uu                                             22

<210> SEQ ID NO 91
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
aucaguucuu uuggccagaa uuu                                            23

```
<210> SEQ ID NO 92
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aucaguucuu uuggccagaa uuuu                                            24
```

COMPOSITIONS AND METHODS FOR REGULATING GENE EXPRESSION VIA RNA INTERFERENCE

INCORPORATION OF SEQUENCE LISTING

This application contains an electronic equivalent paper copy of the sequence listing submitted herewith electronically via EFS web and a computer-readable form of the sequence listing submitted herewith electronically via EFS web and contains the file named "P34087US01_SuppSEQ2016-02-16.txt" (22,327 bytes, created on Feb. 16, 2016), which is hereby incorporated by reference in its entirety.

FIELD

The present disclosure provides compositions and methods for regulating gene expression via RNA-mediated silencing. The present disclosure also provides compositions and methods to optimize the directional processing of a dsRNA molecule into small RNA (sRNA) duplexes.

BACKGROUND

Non-transgenically produced, exogenous nucleic acid molecules, for example, double-stranded RNA (dsRNA) molecules, have been shown to trigger the silencing of a plant endogenous gene after being applied topically to a plant leaf or by soaking a seed with a solution containing the nucleic acid molecules. See U.S. Patent Publication Nos. 2011/0296556, and 2013/0318657 (both incorporated by reference in their entireties). Therefore, plant traits can be modified by introducing into a plant or seed dsRNA molecules that specifically regulate the expression of genes responsible for those traits.

RNA-mediated sequence-specific gene regulation, also called RNA interference (RNAi), starts with a dsRNA that comprises a RNA strand that complements the sequence of a gene of interest. The dsRNA molecule is then processed into shorter fragments of approximately 21-24 nucleotides by an RNase III-related enzyme (Dicer). These fragments, called small interfering RNAs (siRNAs), get incorporated into the RNA-induced silencing complex (RISC). After additional processing, the siRNAs are transformed into single-stranded RNAs that act as guide sequences to recognize and direct the cleavage of target gene transcripts.

Plant cells can produce dsRNAs. A tomato RNA-Dependent RNA Polymerase (RDR) has been reported to produce dsRNAs with 1-nt or 2-nt 3'-overhangs at both termini. See Schiebel et al., J. Biol. Chem. 263:11858-67 (1993); Rajeswaran et al., Nucleic Acid Res., 40(13):6241-54 (2012). It is desired to have a dsRNA processed into siRNAs, and eventually single-stranded RNAs, following a predictable and pre-programmed pattern. The instant application provides and discloses, among others, sequence and structural features that are incorporated into a dsRNA molecule to improve the predictability of the processing of a dsRNA into siRNAs functional in guiding the silencing of intended target genes. Therefore, the instant application provides nucleic acid molecules with higher efficacy in promoting gene regulation and trait modification.

SUMMARY

The instant disclosure provides compositions and methods for regulating gene expression. In one aspect, the instant disclosure provides exogenous trigger molecules for RNAi-mediated silencing in plants.

In one aspect, the instant disclosure provides a double-stranded RNA (dsRNA) molecule comprising a). a first strand comprising a nucleotide sequence that is essentially identical to at least 18 consecutive nucleotides of a target nucleotide sequence; and b).a second strand comprising in the 5' to 3' direction, a 5'-overhang, a nucleotide sequence that is essentially complementary to the first strand, and a 2 nucleotide 3'-overhang, wherein the 5'-overhang is at least 5 nucleotides in length.

In another aspect, the instant disclosure provides a dsRNA molecule comprising: a). a first strand comprising in the 5' to 3' direction, i). a first nucleotide sequence that is identical to at least 18 consecutive nucleotides of a first target nucleotide sequence; ii). a second nucleotide sequence comprising 2 or more As; and iii). a third nucleotide sequence that is identical to at least 18 consecutive nucleotides of a second targeted nucleotide sequence or at least 18 consecutive nucleotides of the first target nucleotide sequence; and b). a second strand comprising in the 5' to 3' direction, a 5 nucleotide 5'-overhang, a nucleotide sequence that is complementary to the first strand, and a 2 nucleotide 3'-overhang. In some embodiments, the first and second target nucleotide sequences are identical.

In a further aspect, the instant disclosure also provides a composition comprising a dsRNA molecule disclosed herein. In another aspect, the instant disclosure provides a plant, plant part, or seed comprising a dsRNA molecule disclosed herein, wherein the dsRNA molecule is exogenous to the plant, plant part, or seed.

In one aspect, the instant disclosure provides a method of regulating expression of at least one target gene, comprising applying onto the surface of a plant or plant part a composition comprising a dsRNA molecule disclosed herein, wherein the dsRNA molecule comprises a first strand comprising a nucleotide sequence that is essentially identical to at least 18 consecutive nucleotides of the target gene.

In another aspect, the instant disclosure also provides a method of improving the efficiency of a dsRNA molecule in producing desired small RNAs in a plant, plant part or seed, comprising providing to the plant, plant part or seed a dsRNA molecule disclosed herein, wherein the production of the 21-24 nucleotide small RNAs is directionally biased towards the 3' end of the second strand of the dsRNA molecule.

In one aspect, the instant disclosure provides a dsRNA molecule, wherein the processing of a population of the dsRNA molecules into one or more 21-24 mer small RNAs (sRNAs) preferentially starts from an end having a 3' overhang, and wherein at least 50%, 60%, 65%, 70%, 75%, 80%, 85%, 90%, or 95% of detectable 21-24 mer sRNAs processed therefrom comprise a sequence identical to a sequence of a first double-stranded portion of at least 15, 16, 17, 18, 19, 20, 21, 22, or 23 nucleotides immediately adjacent to the 3' overhang.

In one aspect, the instant disclosure provides a dsRNA molecule, wherein the first cleavage of the dsRNA molecule by a Dicer-like protein is at a position of about 21 to 24 nucleotides from the 3' terminus of a 3' overhang, and wherein at least 50%, 60%, 65%, 70%, 75%, 80%, 85%, 90%, or 95% of detectable 21-24 mer sRNAs processed from the population of the dsRNA molecules comprise a sequence identical to a sequence of a first double-stranded portion of at least 15, 16, 17, 18, 19, 20, 21, 22, or 23 nucleotides immediately adjacent to the 3' overhang.

In one aspect, the instant disclosure provides a dsRNA molecule, wherein the processing of a population of the dsRNA molecule into one or more 21-24 mer sRNAs preferentially starts from one end of the dsRNA molecule, and wherein the most abundant detectable 21-24 mer sRNAs processed from the population of the dsRNA molecules comprise a sequence identical to a sequence of a first double-stranded portion of at least 15, 16, 17, 18, 19, 20, 21, 22, or 23 nucleotides immediately adjacent to the 3' overhang. In another aspect, the second most abundant detectable 21-24 mer sRNAs processed from a population of dsRNA molecules as disclosed herein comprise a sequence identical to a sequence immediately adjacent to the first double-stranded portion.

In one aspect, the instant disclosure provides a dsRNA molecule comprising a 5' overhang at a first end of the dsRNA molecule, wherein the processing of the dsRNA molecule into one or more sRNAs preferentially starts from a second end of the dsRNA molecule, and wherein the first and second ends are opposite ends of the dsRNA molecule.

In one aspect, a dsRNA molecule or directional trigger of the instant disclosure comprises a first end portion comprising a 3' overhang, a second end portion comprising a 5' overhang, and two or more target-specific sequences that are adjoined by one or more linker sequences.

In one aspect, the instant disclosure provides a directional trigger comprising an exogenous dsRNA molecule having a preferential directionality when processed into sRNAs by a Dicer-like protein. In one aspect, a directional trigger of the instant disclosure comprises a 3' overhang. In some embodiments, the 3' overhang is at least 2 nucleotides in length. In some embodiments, the 3' overhang has the sequence UA, UU, AA, AU, UG or UC. In another aspect, a directional trigger of the instant disclosure comprises a 5' overhang. In some embodiments, the 5' overhang has a high GC content. In some embodiments, the 5' overhang is 2, 3, 4, 5, 6, 7, 8, 9, 10, 11, 12, 13, 14, 15, 16, 17, 18, 19, 20 or more nucleotides in length. In some embodiments, the 5' overhang is at least 5 nucleotides in length. In a further aspect, a directional trigger has a 3' overhang and a 5' overhang on the same strand. In a further aspect, a directional trigger has a 3' overhang and a 5' overhang on the antisense strand. In a further aspect, a directional trigger has a 5'G on the sense strand.

In a further aspect, the instant disclosure provides a plant, plant part or seed comprising a dsRNA molecule disclosed herein, wherein the dsRNA molecule is exogenous to the plant, plant part or seed.

In one aspect, a dsRNA molecule or directional trigger as disclosed herein has a pre-programmed processing pattern for generating sRNAs where sRNA processing starts from an end comprising a 3' overhang and continues in a phased manner with about a 21-nucleotide phase. In a further aspect, a directional trigger is capable of producing one or more sRNA duplexes that have strand-selectivity by preferentially having their antisense strands as guide strands. In some aspect, at least one sRNA duplex produced by a directional trigger as disclosed herein comprises a Uracil or a Uracil-Uracil di-nucleotide at the 5' end of its antisense strand.

In one aspect, the dsRNA molecule or directional trigger disclosed herein is a chimera comprising two or more target-specific sequences that, when the directional trigger is cleaved by a Dicer-like protein, yield the same number of sRNAs, each of which has one target-specific sequence. In one aspect, two or more target-specific sequences are immediately adjacent to each other in a directional trigger. In one aspect, two or more target-specific sequences are not adjacent in a directional trigger. In one aspect, two or more target-specific sequences are not contiguous in a directional trigger. In one aspect, two or more target-specific sequences of a directional trigger are from two or more different genes. In another aspect, two or more target-specific sequences in a directional trigger are derived from a same gene but non-contiguous in that gene. In a further aspect, two or more target-specific sequences of a directional trigger has essentially identical sequences. In another aspect, a directional trigger further comprises one or more AU-rich linker sequences adjoining two or more target-specific sequences.

In one aspect, at least 50% of sRNAs processed from a directional trigger as disclosed herein are from the 3' end of the antisense strand of the directional trigger. In another aspect, at least 50% of sRNAs processed from a directional trigger as disclosed herein comprise a sequence from the 3' end of the antisense strand of the directional trigger.

In one aspect, a directional trigger as disclosed herein is not from a viral vector. In another aspect, a directional trigger as disclosed herein is not produced from a natural viral infection.

In one aspect, a directional trigger as disclosed herein is chemically synthesized or enzymatically produced. In another aspect, a directional trigger as disclosed herein is chemically modified. In one aspect, chemical modification of a directional trigger is capable of enhancing delivery of the molecule into a plant cell or stability of the molecule in a plant cell. In another aspect, chemical modification of a directional trigger is selected from the group consisting of a cholesterol moiety and a modified nucleotide.

In one aspect, a directional trigger as disclosed herein is capable of regulating gene expression via a mechanism selected from the group consisting of RNA cleavage, translation or transcription attenuation, and DNA modification.

In one aspect, a directional trigger as disclosed herein comprises one or more target-specific sequences from one or more target genes selected from the group consisting of an endogenous plant gene, a transgene, an essential gene of a plant pest or pathogen, a plant gene providing resistance to a herbicide, and a plant gene involved in abiotic or biotic stress tolerance.

In one aspect, the instant disclosure provides a double-stranded RNA (dsRNA) molecule comprising a) two or more sRNA trigger sequences that encode the same number of sRNAs, wherein the two or more sRNA trigger sequences are not found in a single naturally occurring molecule or not contiguous in a single naturally occurring molecule, b) a length between about 45 and about 75 nucleotides, c) one or more Adenine- or Uracil-rich linker sequences adjoining the two or more sRNA trigger sequences, d) a 3' overhang in the antisense strand of the dsRNA molecule, e) a Uracil at positions 20, 21 in the antisense strand, the positions 20 and 21 are the 20th and 21st nucleotides relative to terminus of the 3' overhang, respectively, and f) a 5' overhang of 3 to 5 nucleotides.

In one aspect, the instant disclosure provides a composition comprising a directional trigger as disclosed herein, and a transferring agent which facilitates transfer of the directional trigger from the surface of a plant into a cell of a plant. In one aspect, a composition as disclosed herein comprises a transferring agent selected from the group consisting of a surfactant and a salt. In one aspect, a transferring agent of the instant disclosure comprises a humectant or a chelating agent.

In one aspect, a composition as disclosed herein comprises a directional trigger and an organosilicone surfactant. In another aspect, a composition as disclosed herein comprises a directional trigger and a silicone polyether copolymer. In one aspect, a composition as disclosed herein comprises a directional trigger and an organic or an inorganic salt.

In a further aspect, the instant disclosure provides a plant or seed treated with a composition comprising a directional trigger as disclosed herein, and a transferring agent. In another aspect, the instant disclosure provides a plant, a plant part, or seed comprising a directional trigger as disclosed herein.

In a further aspect, the instant disclosure provides a method of applying a directional trigger, or a composition made thereof, to a plant, plant part or seed to confer a beneficial trait.

BRIEF DESCRIPTION OF THE DRAWINGS

FIGS. 1A-1C: Without being limited by any particular theory, overhangs on dsRNA molecules influence both the processing of the molecule and the molecule's ability to promote gene silencing. FIG. 1A illustrates six dsRNA triggers each of which comprises two strands of ~50 nucleotides with overhangs of various lengths. These dsRNA triggers target a tomato (Solanum lycopersicum, Sl) 5-enolpyruvylshikimate-3-phosphate synthase (EPSPS) gene. Trigger 1 has blunt ends. Trigger 2 has 2-base 3' overhangs on both ends. Triggers 3 to 6 have on each end 2-base, 5-base, 10-base and 15-base 5' overhangs, respectively. All triggers are 5'-end-labeled with P32. FIG. 1B illustrates a denaturing polyacrylamide gel analysis of the processing of triggers 1 to 6 after a 2-hr incubation in wheat germ extract (WGE). The presence of 5' overhangs delays or prevents the processing of a dsRNA trigger molecule. The arrowhead denotes the presence of siRNAs, while the arrow indicates full-length trigger molecules. A size ladder is marked to the left of the image. FIG. 1C shows Taqman quantitative PCR data illustrating various extents of down-regulation of a EPSPS gene in Nicotiana benthamiana protoplasts by dsRNA triggers 1 to 6. The degree of target silencing by trigger molecules having 5' overhangs on both ends decreases as the length of the 5' overhangs increases.

In FIG. 5A, the sense strand of a directional trigger comprises target-specific sequences from genes of interest (GOIs). Target-specific sequences 1 and 2 as shown in the figure can be from a same GOI or different GOIs. The antisense strand of a directional trigger comprises both a 3' overhang (2-nt exemplified) and a 5' overhang. A Dicer-like protein cleaves a first 21-24 mer (siRNA1) from a directional trigger preferentially starting from the end with a 3' overhang, and also produces a second 21-24 mer (siRNA2) which is immediately next to the first 21-24 mer (e.g., in phase with the first 21-24 mer). Accordingly, a Directional dsRNA trigger produces a group of 21-24 mers (two 21-24 mers are shown in the figure) in a phased manner with siRNA1 and siRNA2 being the predominant species. Both siRNA1 and siRNA2 comprise a UU di-nucleotide at the 5' end of the antisense strand and a G at the 5' end of the sense strand. Antisense strands of siRNA1 and siRNA2 starting with a UU di-nucleotide are preferentially loaded into Argonaute proteins (AGO), and are also called guide strands that guide the recognition of target gene mRNA sequences and lead to target gene silencing.

A non-directional dsRNA trigger can be chimeric or non-chimeric, blunt-ended, having 3' overhangs on both ends, or a combination of these features. Shown in FIG. 5B, a chimeric trigger has two 3' overhangs. A non-directional dsRNA trigger has no directionality bias towards either end of the trigger when processed by a dicer-like protein. Accordingly, 21-24 mers produced from a non-directional dsRNA trigger are more heterogeneous. In-phase 21-24 mers (e.g., siRNA1' and siRNA2') represent only a fraction of the total pool of 21-24 mers which also comprise substantial out-of-phase 21-24 mers (e.g., siRNA3' and siRNA4'). As such, a non-directional dsRNA trigger produces more diluted in-phase 21-24 mers compared to a directional trigger.

Further, 21-24 mers produced from a non-directional dsRNA trigger lack a UU di-nucleotide at the 5' end of their antisense strand and a G at the 5' end of their sense strand. Accordingly, neither the antisense strand, nor the sense strand is preferentially loaded into a AGO protein. Instead, each strand of every 21-24 mer can potentially be loaded into an AGO protein as a guide strand. Guide strands 1' and 2' are complementary to target sequences and capable of recognizing target molecules to cause silencing. Therefore, a non-directional dsRNA trigger produces more diluted guide strands that are effective in causing silencing compared to guide strands produced from a directional trigger.

Figure 5A:
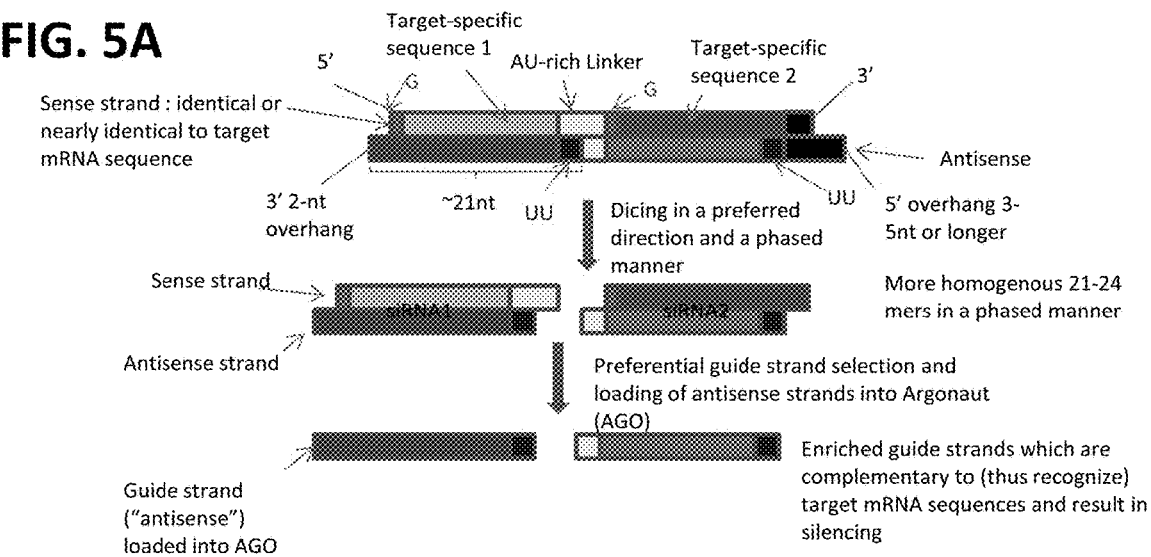
FIGS. 5A-5B: A schematic comparison between one embodiment of a directional dsRNA trigger and a non-directional dsRNA trigger. The schematic drawings and the following explanation are provided for illustration purposes only, and are not bound to any scientific theory or mechanism.
Figure 6A:
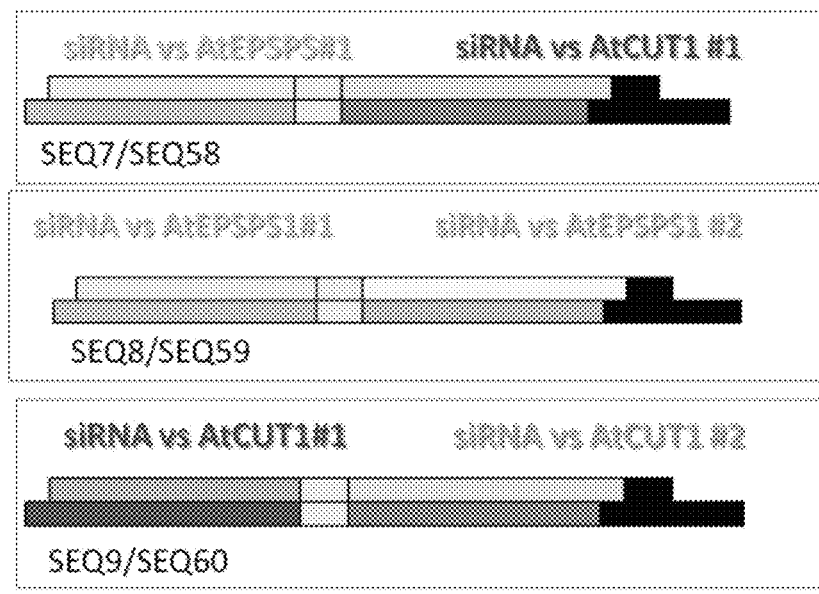
Figure 6B:
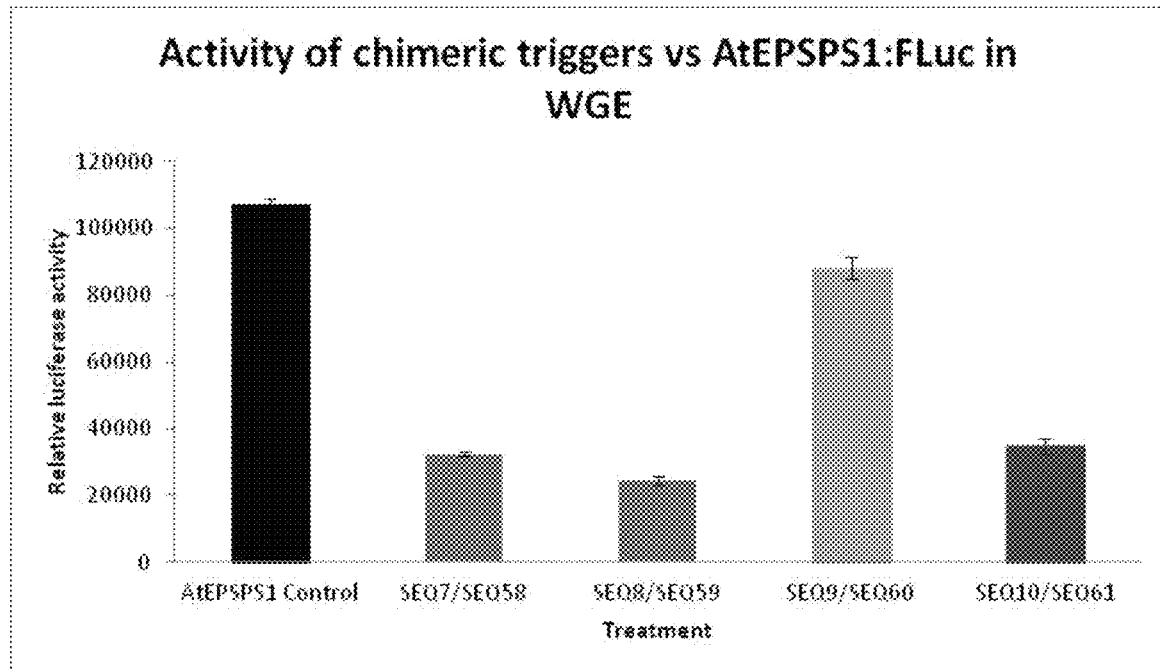
Figure 6C:
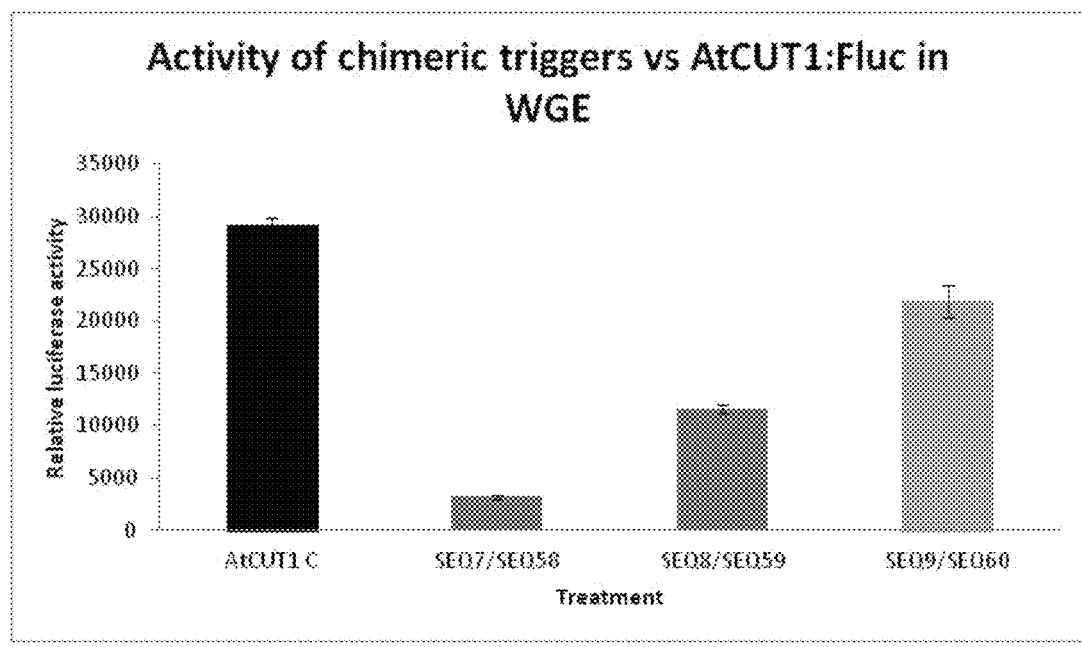
Figure 6D:
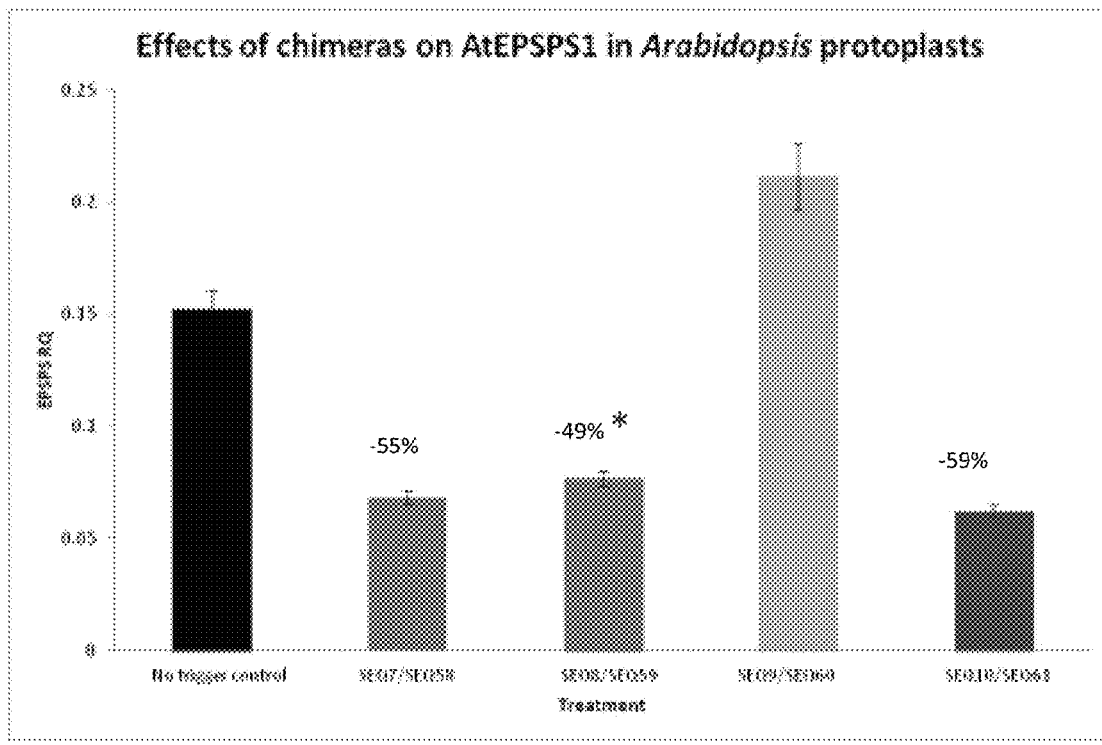

FIGS. 6A-6D: Directional triggers against two *Arabidopsis* target genes generate two functional siRNAs against their intended targets in *Arabidopsis* protoplasts. FIG. 6A illustrates schematic representations of three directional chimeric dsRNA triggers tested. These directional dsRNA triggers each comprise two target sequences, each of which is from AtEPSPS or AtCUT1 (SEQ ID NO:7/SEQ ID NO:58), or both of which are from either AtEPSPS (SEQ ID NO:8/SEQ ID NO:59) or AtCUT1 (SEQ ID NO:9/SEQ ID NO:60). FIG. 6B shows activity of chimeric triggers in wheat germ extract (WGE) silencing a fusion target mRNA AtEPSPS1:Fluc. AtEPSPS1:Fluc is an mRNA fusion between a full-length luciferase coding sequence and an AtEPSPS1coding sequence which is targeted by triggers SEQ ID NO:7/SEQ ID NO:58, SEQ ID NO:8/SEQ ID NO:59, and SEQ ID NO:10/SEQ ID NO:61. SEQ ID NO:10/SEQ ID NO:61 is a non-directional dsRNA trigger. FIG. 6C shows activity of chimeric triggers in wheat germ extract (WGE) silencing a target mRNA. AtCUT1:Fluc is an mRNA fusion between a full-length luciferase coding sequence and an AtCUT1 coding sequence that is targeted by triggers SEQ ID NO:7/SEQ ID NO:58 and SEQ ID NO:9/SEQ ID NO:60, but not SEQ ID NO:8/SEQ ID NO:59. The y-axis reflects relative luciferase activity normalized to Renilla luciferase. Error bars represent standard deviations. For WGE incubation, fusion target mRNA were used at 3 pmol/µl while triggers were used at 60 pmol/µl. FIG. 6D shows q-PCR results for AtEPSPS1 expression levels ("EPSPS RQ") in *Arabidopsis* protoplasts after treatment with directional dsRNA triggers from FIG. 5A. Directional triggers containing at least one siRNA sequence against AtEPSPS1 (SEQ ID NO:7/SEQ ID NO:58 and SEQ ID NO:8/SEQ ID NO:59) are capable of specifically downregulating AtEPSPS1 expression, while directional trigger against AtCUT1 (SEQ ID NO:9/SEQ ID NO:60) cannot silence AtEPSPS1. The percentages of AtEPSPS1 down-regulation in each treatment compared to the no-trigger control are shown in the figure. All triggers were tested at a 200 pmol dosage except trigger SEQ ID NO:8/SEQ ID NO:59 which contains two distinct siRNAs both targeting AtEPSPS1 and was evaluated at a 50 pmol dosage. This lower dosage of SEQ ID NO:8/SEQ ID NO:59 achieving target down-regulation close to that by a higher concentration of SEQ ID NO:7/SEQ ID NO:58 shows that SEQ ID NO:8/SEQ ID NO:59 having two target-specific sequences from AtEPSPS1 has a higher efficacy compared to SEQ ID NO:7/SEQ ID NO:58.

Figure 7A:
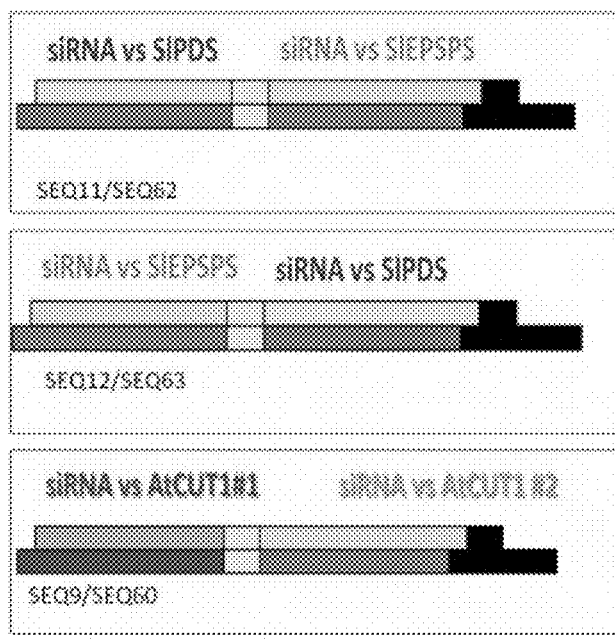
Figure 7B:
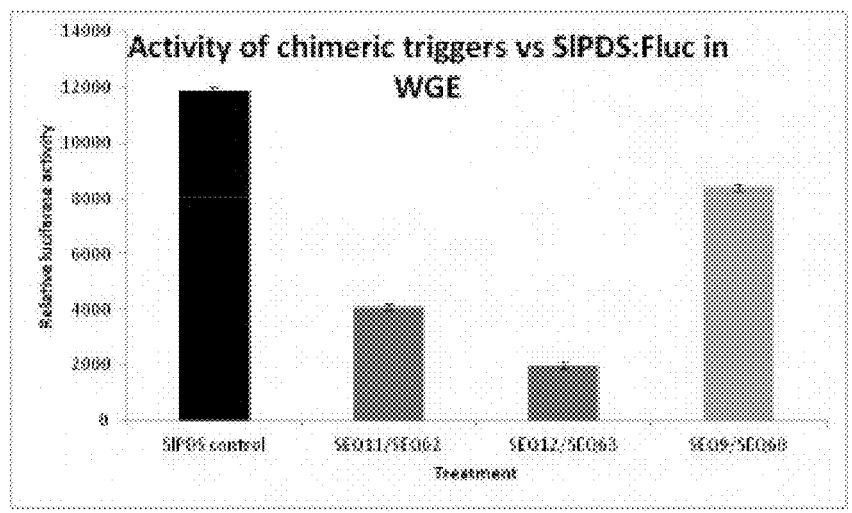
Figure 7C:
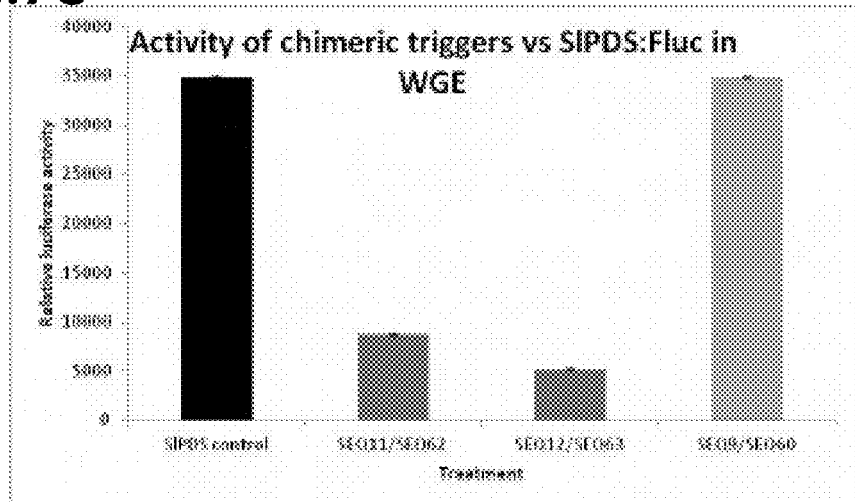
Figures 7D, 7E:
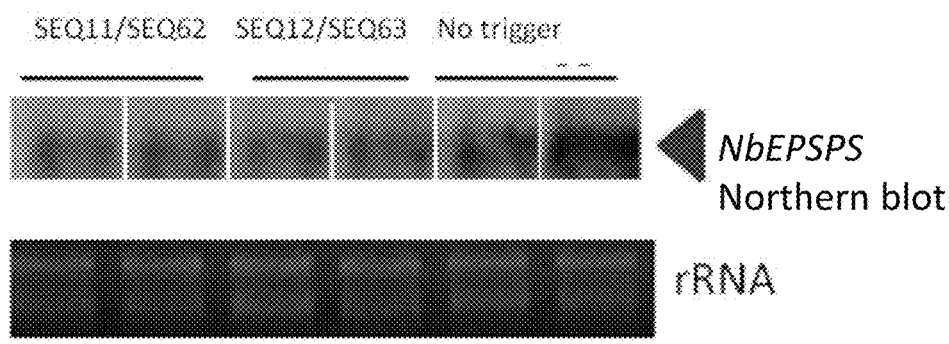

FIGS. 7A-7E: Directional chimeric dsRNA triggers targeting tomato (*Solanum lycopersicum*, Sl) phytoene desaturase (PDS) and EPSPS genes are effective in triggering silencing in *Nicotiana benthamiana* (Nb) protoplasts. FIG. 7A illustrates schematic representations of three directional triggers tested. SEQ ID NO:11/SEQ ID NO:62 and SEQ ID NO:12/SEQ ID NO:63 each comprise two target sequences, one from SlPDS and the other from SlEPSPS. Arrangements of the two target sequences are reversed between SEQ ID NO:11/SEQ ID NO:62 and SEQ ID NO:12/SEQ ID NO:63. FIG. 7B shows activity of chimeric triggers in wheat germ extract (WGE) silencing a target mRNA SlPDS:Fluc. SlPDS:Fluc is an mRNA fusion between a full-length luciferase coding sequence and a SlPDS coding sequence which is targeted by triggers SEQ ID NO:11/SEQ ID NO:62 and SEQ ID NO:12/SEQ ID NO:63, but not SEQ ID NO:9/SEQ ID NO:60. FIG. 7C shows activity of chimeric triggers in WGE silencing a target mRNA SlEPSPS:Fluc. SlEPSPS:Fluc is an mRNA fusion between a full-length luciferase coding sequence and a SlEPSPS coding sequence which is targeted by triggers SEQ ID NO:11/SEQ ID NO:62 and SEQ ID NO:12/SEQ ID NO:63, but not SEQ ID NO:9/SEQ ID NO:60. The y-axis reflects relative luciferase activity normalized to an internal Renilla luciferase control reporter. Error bars represent standard deviations. For WGE incubation, target mRNAs were used at 3 pmol/µl, while each trigger was used at 60 pmol/µl. FIG. 7D shows Northern blot results demonstrating down-regulation of a NbEPSPS gene by triggers SEQ ID NO:11/SEQ ID NO:62 and SEQ ID NO:12/SEQ ID NO:63 in *Nicotiana benthamiana* protoplasts and a rRNA control below. FIG. 7E lists quantification results of target gene (Gene of Interest, GOI) downregulation by triggers SEQ ID NO:11/SEQ ID NO:62 and SEQ ID NO:12/SEQ ID NO:63 in *Nicotiana benthamiana* protoplasts via either a 5' probe or a 3' probe. % KD refers to the percentage of gene knockdown by each trigger compared to a no-trigger control.

Figure 8:
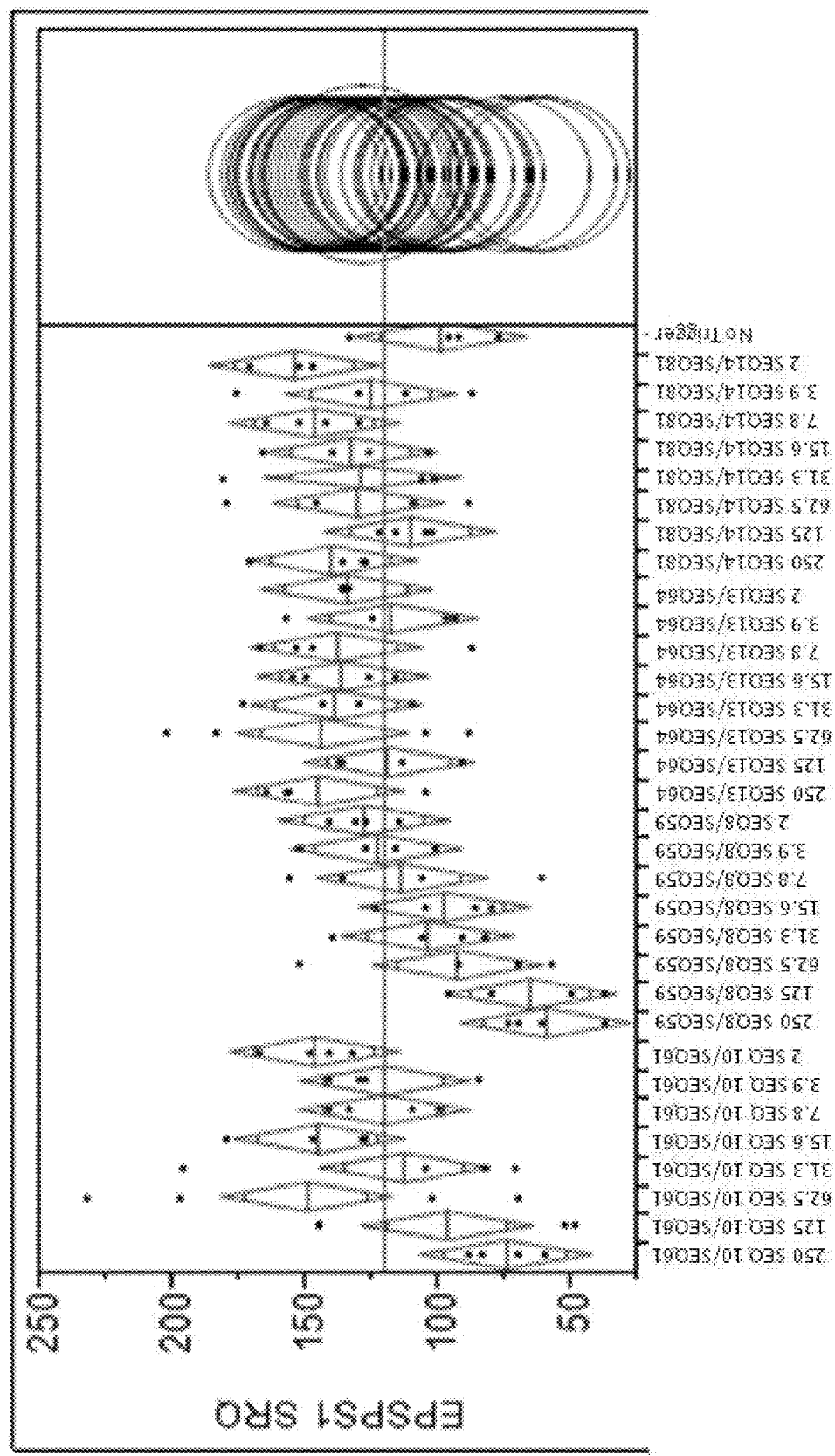

FIG. 8: A comparison of target down-regulation in *Arabidopsis* protoplasts between a directional dsRNA trigger (SEQ ID NO:8/SEQ ID NO:59 targeting AtEPSPS1, see FIG. 5A) and a non-directional trigger SEQ ID NO:10/SEQ ID NO:61 shows that a directional dsRNA trigger has a higher silencing efficacy compared to a non-directional trigger. Eight different trigger concentrations (250, 125, 62.5, 31.3, 15.6, 7.8, 3.9, and 2.0 pmol) were tested. SEQ ID NO:14/SEQ ID NO:64 and SEQ ID NO:14/SEQ ID NO:81 represent negative control directional dsRNA triggers that do not target AtEPSPS1. Triggers are listed on the x-axis according to their concentration. For example, the first data point on the x-axis "01 250 SEQ ID NO:10/SEQ ID NO:61" refers to treatment No. 01 which uses 250 pmol of trigger SEQ ID NO:10/SEQ ID NO:61. Similarly, the data point on the x-axis "32 2.0 SEQ ID NO:14/SEQ ID NO:81" refers to treatment No. 32 which uses 2.0 pmol of trigger SEQ ID NO:14/SEQ ID NO:81. Relative q-PCR quantification of AtEPSPS1 expression is shown on the y-axis. Student's t-test was performed to show statistic significance. Same quantification results are also shown in Table 2. The directional dsRNA trigger SEQ ID NO:8/SEQ ID NO:59 reduced AtEPSPS1 expression by 34% and 39% when used at 125 and 250 pmol, respectively. The non-directional dsRNA trigger SEQ ID NO:10/SEQ ID NO:61 was capable of reducing AtEPSPS1 expression by 24% at the highest dose (250 pmol), and showed no silencing activity when used at a concentration of 125 pmol or lower. When used at a same concentration (e.g., 250 pmol), directional dsRNA trigger SEQ ID NO:8/SEQ ID NO:59 is more effective in reducing AtEPSPS1 expression compared to non-directional dsRNA trigger SEQ ID NO:10/SEQ ID NO:61 (39% versus 24%).

Figure 9A:
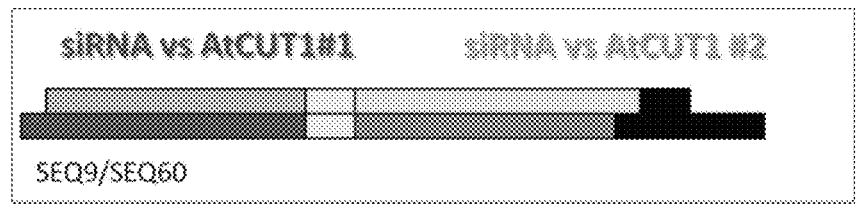
Figure 9B:
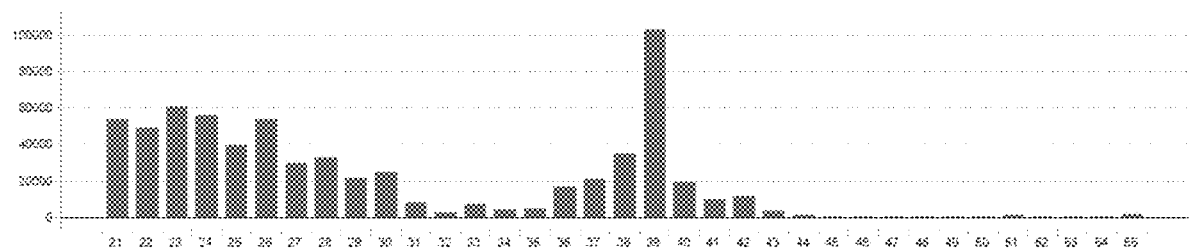
Figure 9C:
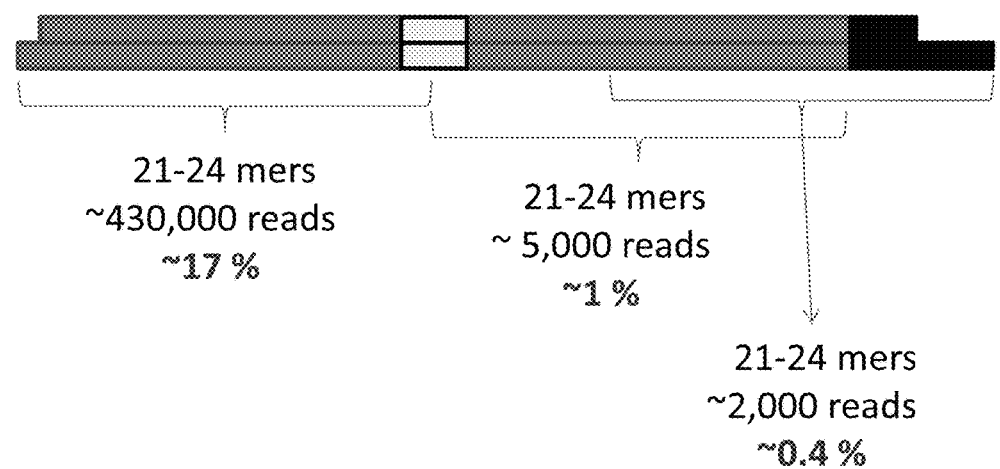

FIGS. 9A-9C: A survey of siRNAs that are processed from a directional chimeric dsRNA trigger via deep sequencing demonstrates directionality. Trigger SEQ ID NO:9/SEQ ID NO:60 (FIG. 9A) was processed in WGE, and the collection of products were subject to deep sequencing thereafter. FIG. 9B shows size distribution for RNA products of the SEQ ID NO:9/SEQ ID NO:60 after processing in WGE on the x-axis and the number of reads of each RNA size on the y-axis. In total, 2,456,774 sequencing reads are mapped to trigger SEQ ID NO:9/SEQ ID NO:60, of which 2,107,001 reads (~85%) are from the antisense strand of trigger SEQ ID NO:9/SEQ ID NO:60 while 349,774 sequencing reads (~15%) are from the sense strand of trigger SEQ ID NO:9/SEQ ID NO:60. FIG. 9C shows that the size range of 21-24 (i.e., 21-24 mer) contains 473,000 sequencing reads (~19%), of which ~90% are mapped to the 3' end of the antisense strand of trigger SEQ ID NO:9/SEQ ID NO:60 with only ~0.4% from the 5' end of the sense strand. Analysis of the 21-24 mers shows an overrepresentation of the 3' end of the antisense strand compared to the antisense 5' end (~17% versus ~0.4%), which supports a preferential, directional processing of the chimeric trigger starting from the end comprising a 2-nt 3' overhang. The processing patterns of two additional triggers, SEQ ID NO:7/SEQ ID NO:58 and SEQ ID NO:8/SEQ ID NO:59, into 21-24 mers are shown in Table 1.

Figure 10:
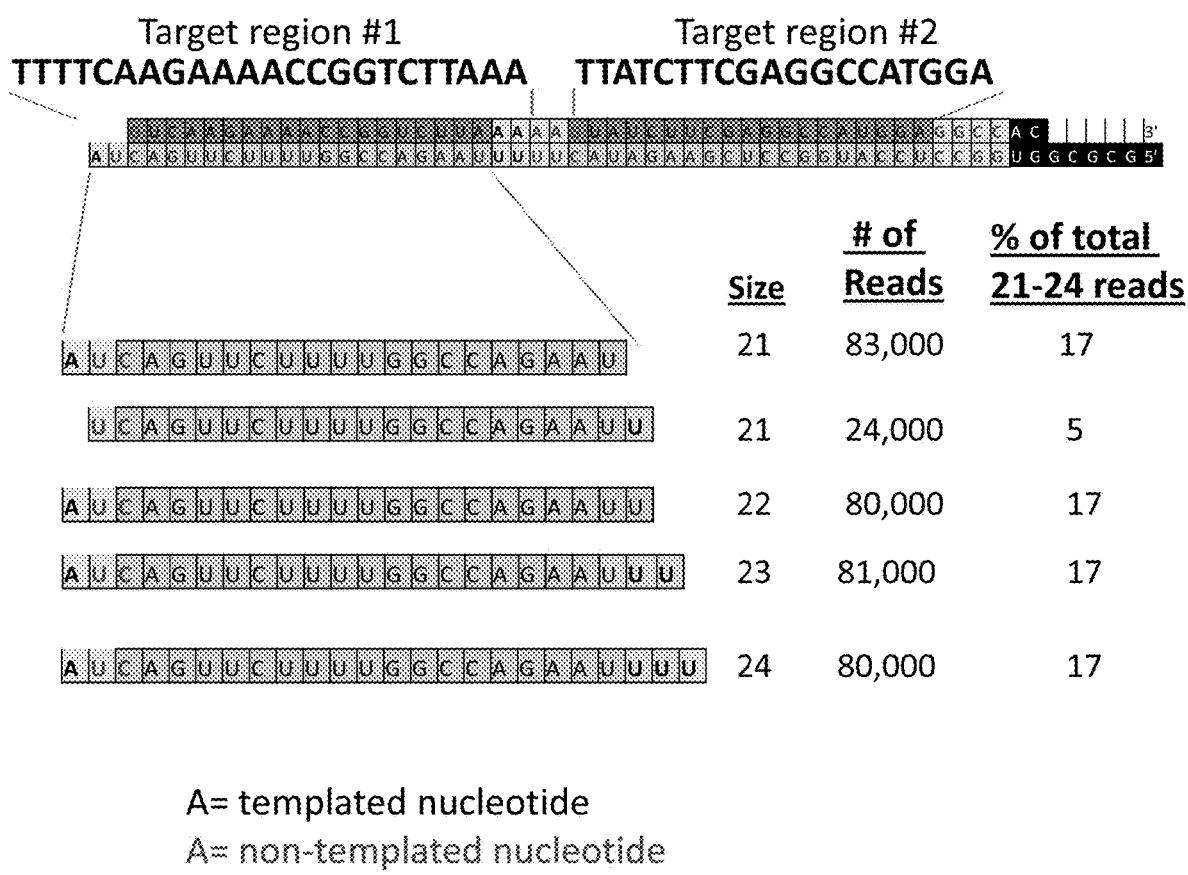

FIG. 10: A detailed analysis of the 21-24 mers from the 3' end of the antisense strand processed from Trigger SEQ ID NO:9/SEQ ID NO:60 in WGE as in FIG. 7. For each size and sequence listed (SEQ ID NOs:88-92), both the number (#) of sequencing reads and its percentage of the total number of 21-24 mers are shown.

Figure 11:
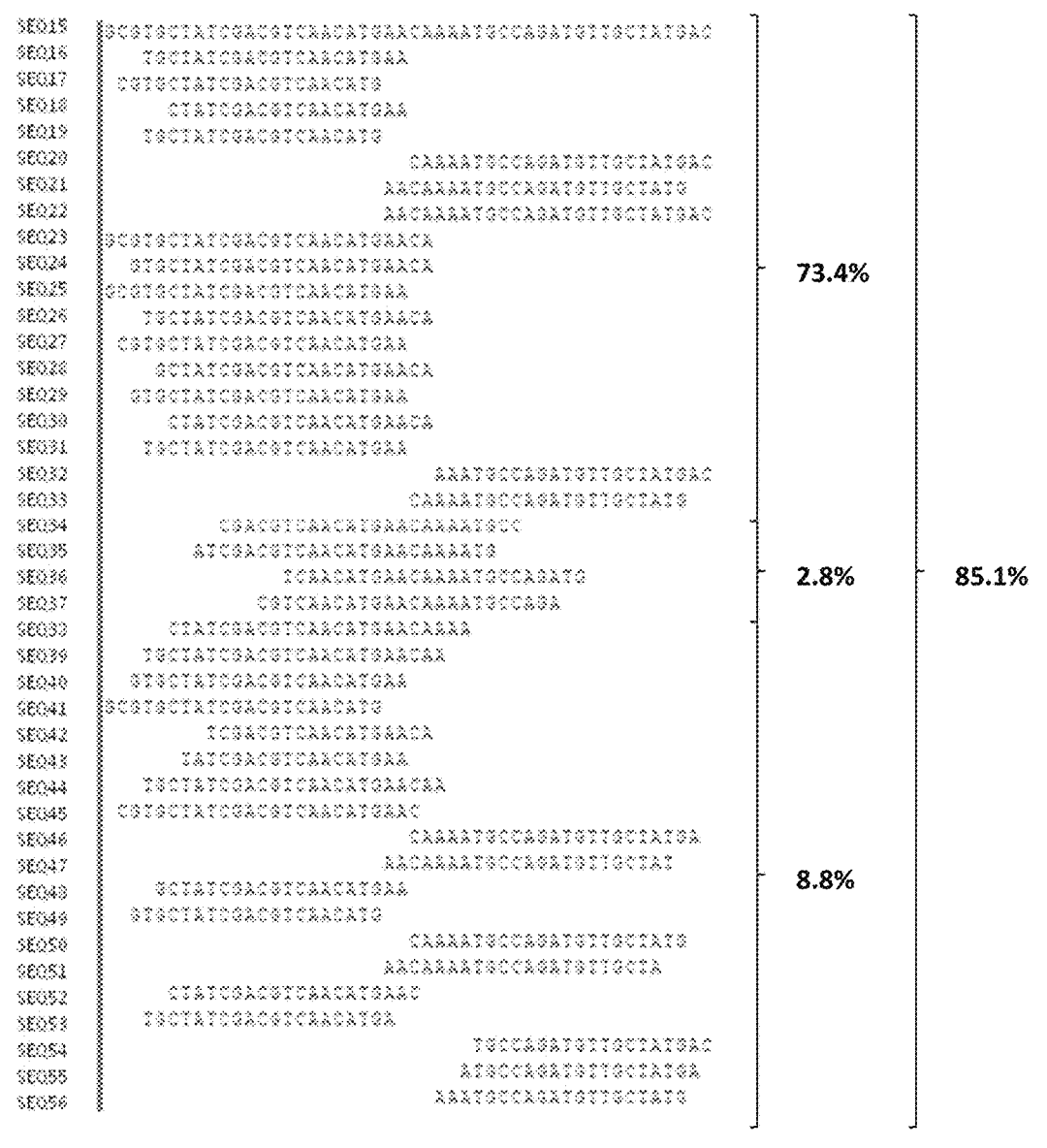

FIG. 11: An alignment of the most abundant putative primary siRNA duplexes (e.g., perfect-match double-stranded 21-24 mers) from a 48-nt trigger sequence (SEQ ID NO:15, top row). Putative siRNA duplexes were assembled in silico from 21-24 mer sequencing reads which are generated by sequencing small RNAs processed from trigger BOL5.2 in WGE. These putative siRNA duplexes are ranked based on their relative abundance estimated by the sum of their absolute frequencies. Top ranked putative duplexes (only perfect-match 21-24 mers) were aligned against the BOL5.2 48-nt trigger sequence. The top 10 putative siRNA duplexes amount to ~75% of all perfect match reads. Among these 10 duplexes, only 3 preferentially match to the 3' side of the trigger (the dsRNA end with a 5' overhang). Four top-ranked duplexes (two 21-nt and two 24-nt siRNAs) showed opposite strand biases. The two top-ranked 21-nt siRNAs are biased towards the antisense strand, while the two top-ranked 24-nt siRNAs have a bias to the sense strand.

Figure 12:
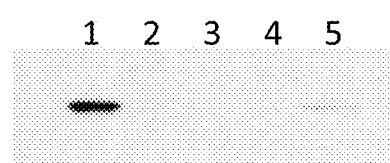
Figure 12:
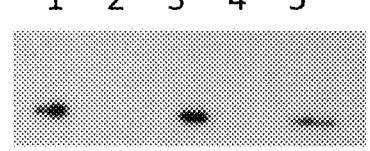

FIG. 12: Results of the Western Blot analysis using anti-GFP (panel A) or anti-MgChl (panel B) polyclonal antibodies. The lanes are as follows: lane 1 is unsilenced green tissue (under UV light) from plants treated with GFP only trigger; lane 2 is empty; lane 3 is tissue prepared from GFP silenced treatment (red spots under UV light); lane 4 is empty; lane 5 is from tissue prepared from plants treated with chimeric trigger targeting GFP/MgChl.

Figure 13:
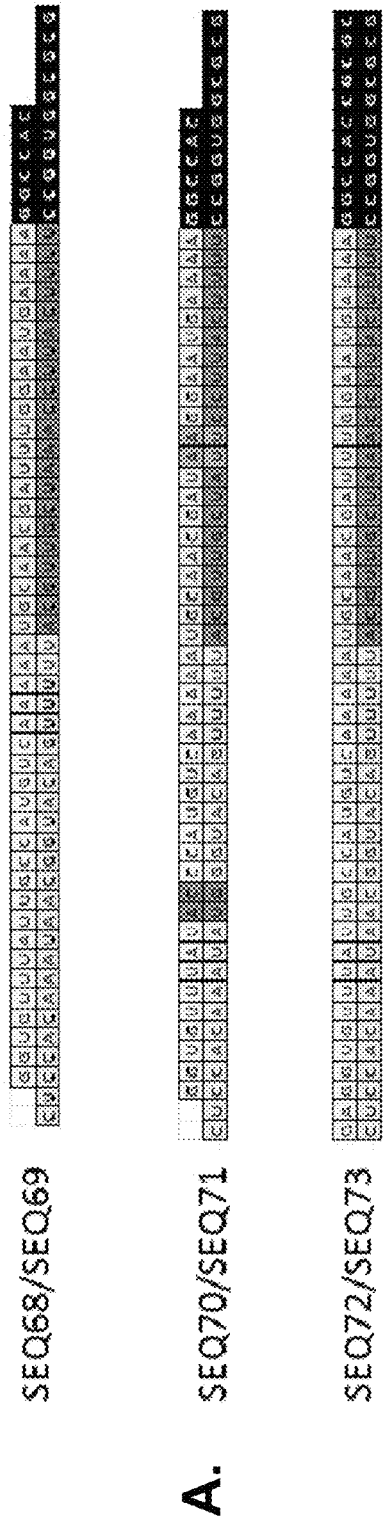
Figure 13:
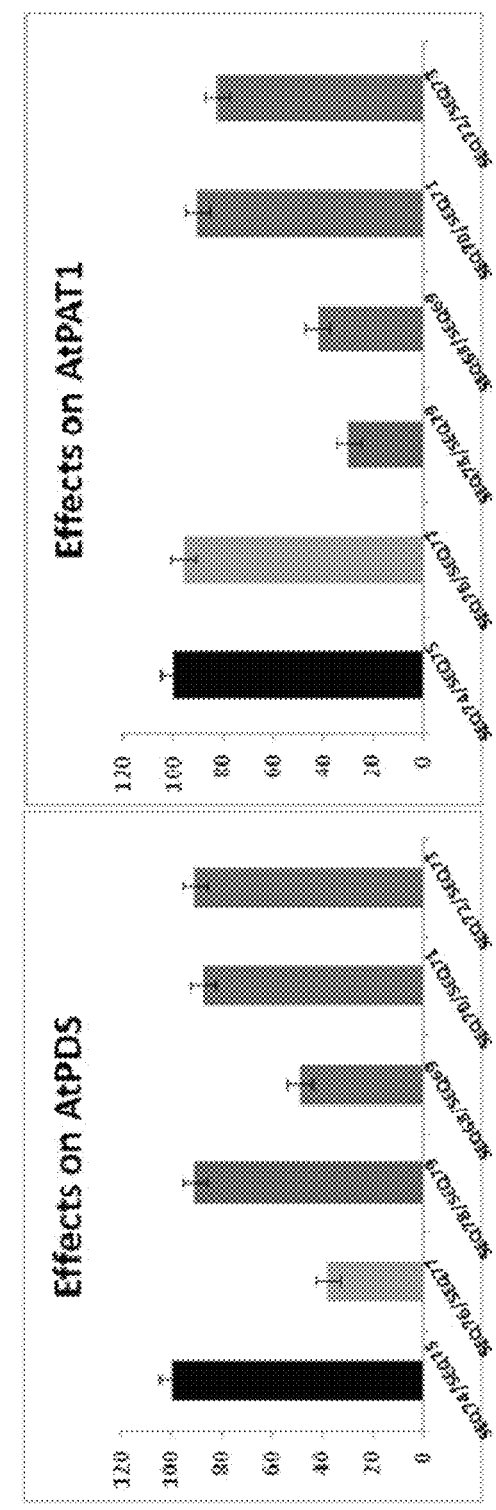

FIG. 13: A diagram and Taqman data of the dsRNA polynucleotides tested in protoplast cells. Panel A shows the three dsRNAs being test: the directional trigger that targets both PDS and PAT1 (SEQ ID NO:68/SEQ ID NO:69) with the 5'-overhang and desired composition, the dsRNA trigger with mutations within the sequence complementary to PDS or PAT1 (SEQ ID NO:70/SEQ ID NO:71), and the blunt ended dsRNA trigger (SEQ ID NO:72/SEQ ID NO:73). Panel B shows the Taqman results obtained after RNA extraction and quantitation.

DETAILED DESCRIPTION

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Moreover, the present disclosure is not intended to be limited by any particular scientific theory. For purposes of the present disclosure, the following terms are defined below.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof.

As used herein, the term "about" indicates that a value includes the inherent variation of error for the method being employed to determine a value, or the variation that exists among experiments.

As used herein, a "dsRNA" molecule refers to a molecule comprising two antiparallel ribonucleotide strands bound together by hydrogen bonds, each strand of which comprises ribonucleotides linked by phosphodiester bonds running in the 5'-3' direction in one and in the 3'-5' direction in the other. Two antiparallel strands of a dsRNA can be perfectly complementary to each other or comprise one or more mismatches up to a degree where any one additional mismatch causes the disassociation of the two antiparallel strands. A dsRNA molecule can have perfect complementarity over the entire dsRNA molecule, or comprises only a portion of the entire molecule in a dsRNA configuration. Two antiparallel strands of a dsRNA can also be from a continuous chain of ribonucleotides linked by phosphodiester bonds, e.g., a hairpin-like structure (often also called a stem-loop structure). In some embodiments, a dsRNA molecule is identified by two SEQ ID NOs, where the first SEQ ID NO represents the sense strand of the dsRNA and the second SEQ ID NO represents the antisense strand of the dsRNA. In other embodiments, a dsRNA molecule is identified by one SEQ ID NO that represents the sense strand of the dsRNA.

As used herein, in the context of RNA-mediated gene silencing, the sense strand of a dsRNA molecule refers to a strand comprising a sequence that is identical or essentially identical to a target RNA sequence. The antisense strand of a dsRNA molecule refers to a strand having a sequence complementary to a target RNA sequence. In a DNA context, the term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene, mRNA molecule or single stranded genomic DNA through Watson-Crick base pairing) or that is complementary to a target DNA molecule such as, for example, genomic DNA present in the host cell.

As used herein, the term "overhang" refers to one or more single-stranded nucleotides at one end of a nucleic acid molecule which comprises a double stranded portion. A "3' overhang" refers to one or more single-stranded nucleotides ending in a 3' hydroxyl or modification thereof. A "3' initiator overhang" refers to a dsRNA molecule's 3' overhang of variable length, e.g., 2-nt, which favors the initiation of dsRNA processing by a Dicer-like protein from the terminus having the 3' overhang. Similarly, a "5' overhang" refers to one or more single-stranded nucleotides ending in a 5' phosphate or modifications thereof. A "5' blocker overhang" refers to a 5' overhang of a dsRNA molecule which disfavors the initiation of dsRNA processing by a Dicer-like protein from the terminus having the 5' overhang. A terminal nucleotide (or terminus) of a 3' or 5' overhang refers to the overhang's nucleotide that is furthest away from a double-stranded portion.

A frayed end refers to a double-stranded nucleic acid molecule end with a significant proportion of non-complementary sequences (e.g., nucleotides on parallel strands do not form Watson-Crick pairing).

As used herein, "small RNA (sRNA)" refers to any RNA molecule that is about 15-30 nucleotides long, preferably 21-24 nucleotides long. A "21-24 mer small RNA" or "21-24 mer sRNA" refers to a small RNA of 21-24 nucleotides which may be double- or single-stranded. A double-stranded 21-24 mer sRNA can comprise at one or both ends one or more structures selected from the group consisting of blunt, 3' overhang, and 5' overhang. A double-stranded 21-24 mer sRNA processed by a Dicer-like protein from a dsRNA precursor molecule typically comprise a 2-nt overhang at both ends.

Small RNA includes, without limitation, siRNA (small interfering RNA), miRNA (microRNA), ta-siRNA(trans activating siRNA), activating RNA (RNAa), nat-siRNA (natural anti-sense siRNA), hc-siRNA (heterochromatic siRNA), cis-acting siRNA, lmiRNA (long miRNA), lsiRNA (long siRNA) and easiRNA (epigenetically activated siRNA). Preferred sRNA molecules of the disclosure are siRNA molecules. A sRNA, in its mature form, can be either double-stranded or single-stranded, although the biogenesis of a sRNA often involves a sRNA duplex which is a double-stranded form of sRNA. While not limited by a particular theory, a sRNA duplex is often processed from a dsRNA precursor (e.g., a directional trigger as disclosed herein) by proteins, such as Dicer-like proteins.

As used herein, the term "siRNA" (also referred to herein interchangeably as "small interfering RNA"), is a class of double-stranded RNA molecules having about 18-25 nucleotides in length (e.g., 18-mers, 19-mers, 20-mers, 21-mers, 22-mers, 23-mers, 24-mers, or 25-mers). A double-stranded siRNA generally has perfect or near perfect complementarity. Without being limited by any theory, a role of siRNA is its involvement in the RNA interference (RNAi) pathway, where it interferes with the expression of a specific target gene.

One strand of a siRNA, called "guide strand," is loaded into a RNA-induced silencing complex (RISC) and guide the recognition of a complementary mRNA molecule (target mRNA molecule) and to trigger subsequent silencing. The other strand of a siRNA, called "passenger strand," is degraded.

As used herein, the term "functional siRNA" refers to a siRNA which is effective in silencing an intended target gene.

As used herein, the phrase "RNA silencing" refers to a group of regulatory mechanisms (e.g., RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding target gene.

As used herein, the phrase "immediately adjacent" refers to a position directly connected, without a gap or spacing, to a reference position or structure. Two nucleic acid sequences are immediately adjacent or contiguous when they are found in a sequence of a single molecule and lie right next to each other without any gap or spacing.

As used herein, a "synthetic sequence" refers to a nucleic acid sequence which lacks a corresponding sequence that naturally occurs.

As used herein, a "target-specific sequence" refers to a nucleic acid sequence that is essentially identical, identical, essentially complementary, or complement of any, to nucleotide sequence that occurs in a gene or gene product against which a trigger polynucleotide is directed. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome or the genome of a pathogen. As used herein, the term "pathogen" refers to virus, viroid, bacteria, fungus, oomycetes, protozoa, phytoplasma, and parasitic plants. Depending upon the circumstances, the term target sequence or target gene can refer to the full-length nucleotide sequence of the gene or gene product targeted for suppression or the nucleotide sequence of a portion of the gene or gene product targeted for suppression. In some embodiments, a target-specific sequence can be derived from a sequence of a messenger RNA (mRNA) which, when hybridizes with a small RNA molecule and leads to the attenuation of target gene expression. In some embodiments, a target-specific sequence can be derived from a sequence of microRNAs, small interfering RNAs, and other small RNAs associated with a silencing complex (RISC) or an Argonaute protein; RNA components of ribosomes or ribozymes; small nucleolar RNAs; and other non-coding RNAs. In some embodiments, a target-specific sequence can be derived from non-translatable (non-coding) sequence, such as, but not limited to, 5' untranslated regions, promoters, enhancers, or other non-coding transcriptional regions, 3' untranslated regions, terminators, and introns. In some embodiments, a target-specific sequence can be derived from a gene encoding transcription factors, enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). Conversely, a "non-target-specific sequence" refers to any nucleic acid sequence that is not a target-specific sequence.

As used herein, the terms "trigger," "trigger polynucleotide," or "polynucleotide trigger" refers to a bioactive polynucleotide molecule that comprises a polynucleotide that substantially homologous or complementary to a polynucleotide sequence of a target gene or an RNA expressed from the target gene or a fragment thereof and functions to suppress the expression of the target gene or produce a knock-down phenotype. Trigger polynucleotides are capable of inhibiting or "silencing" the expression of a target gene. Trigger polynucleotides are generally described in relation to their "target sequence." Trigger polynucleotides may be single-stranded DNA (ssDNA), single-stranded RNA (ssRNA), double-stranded RNA (dsRNA), double-stranded DNA (dsDNA), or double-stranded DNA/RNA hybrids. Trigger polynucleotides may comprise naturally-occurring nucleotides, modified nucleotides, nucleotide analogues or any combination thereof. In some embodiments, a trigger polynucleotide may be incorporated within a larger polynucleotide. In some embodiments, a trigger polynucleotide may be processed into a small interfering RNA (siRNA). A trigger as disclosed herein includes, without limitation, a directional trigger, a directional chimeric trigger, and a strand-selective directional chimeric trigger.

As used herein, a directional trigger is an exogenous dsRNA molecule which can cause the silencing of at least one target gene, and has a preferential directionality when processed into small RNAs by a Dicer-like protein. One embodiment of a directional trigger has a 3' overhang and a 5' overhang on the same strand which, without being bound to any scientific theory or mechanism, favors the initiation of dicer processing from the 3' end and disfavors the initiation of dicer processing from the 5' end. In some embodiments, a directional trigger is a chimeric trigger, which comprises two or more target-specific sequences that, when the directional trigger is cleaved by a Dicer-like protein, yield predictable siRNAs, each of which has one target-specific sequence.

As used herein, a strand-selective directional chimeric trigger is a directional chimeric trigger capable of producing two or more sRNA duplexes, a majority of which sRNA duplexes preferentially have their antisense strands as guide strands.

A non-directional dsRNA trigger molecule ("non-directional trigger") is a dsRNA molecule which has no preferential directionality when processed into sRNAs by a dicer-like protein. Embodiments of a non-directional trigger include, but are not limited to, a dsRNA trigger molecule lacking a 3' initiator overhang, a 5' blocker overhang, or both.

As used herein, the terms "essentially identical" or "essentially complementary" means that the trigger (or at least one strand of a double-stranded polynucleotide or portion thereof, or a portion of a single strand polynucleotide) hybridizes under physiological conditions to the target gene, an RNA transcribed there from, or a fragment thereof, to effect regulation or suppression of the target gene. For example, in some embodiments, a trigger (or at least one strand of a double-stranded trigger) has 100 percent sequence identity or at least about 80, 81, 82, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a trigger (or at least one strand of a double-stranded trigger) has 100 percent sequence complementarity or at least about 80, 81, 82, 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a trigger (or at least one strand of a double-stranded trigger) has 100 percent sequence identity with or complementarity to one allele or one family member of a given target gene (coding or non-coding sequence of a gene). In some embodiments, a trigger (or at least one strand of a double-stranded trigger) has at least about 80, 81, 82, 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a trigger (or at least one strand of a double-stranded trigger) has 100 percent sequence identity with or complementarity to multiple alleles or family members of a given target gene.

As used herein, with respect to a nucleic acid sequence, nucleic acid molecule, or a gene, the term "natural," "naturally existing," or "native" means that the respective sequence or molecule is present in a wild-type cell which has not been genetically modified or manipulated by man. A small RNA molecule naturally targeting a gene means a small RNA molecule present in a wild-type cell, and targeting a gene naturally occurring in the wild-type cell.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, the term "high GC content" refers to at least 50% of guanine or cytosine in the nucleotide composition of a given nucleotide sequence.

As used herein, the terms "exogenous polynucleotide" and "exogenous nucleic acid molecule" relative to an organism refer to a heterologous nucleic acid molecule which does not naturally occur within that organism. An exogenous nucleic acid molecule may be introduced into an organism in a stable or transient manner. An exogenous nucleic acid molecule may comprise a nucleic acid sequence which is identical or partially homologous to an endogenous nucleic acid sequence of the organism.

As used herein, the terms "improving," "improved," "increasing," and "increased" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450% or greater increase in a property or attribute caused by a specific treatment or design feature.

As used herein, "a reduction" of the level of an agent such as a protein or mRNA means that the level is reduced relative to a cell or organism lacking a dsRNA molecule capable of reducing the agent.

As used herein, the term "at least a partial reduction" of the level of an agent such as a protein or mRNA means that the level is reduced at least 25% relative to a cell or organism lacking a dsRNA molecule capable of reducing the agent.

As used herein, "a substantial reduction" of the level of an agent such as a protein or mRNA means that the level is reduced relative to a cell or organism lacking a dsRNA molecule capable of reducing the agent, where the reduction of the level of the agent is at least 75%.

As used herein, "an effective elimination" of an agent such as a protein or mRNA is relative to a cell or organism lacking a dsRNA molecule capable of reducing the agent, where the reduction of the level of the agent is greater than 95%. An agent, preferably a dsRNA molecule, is preferably capable of providing at least a partial reduction, more preferably a substantial reduction, or most preferably effective elimination of another agent such as a protein or mRNA, wherein the agent leaves the level of a second agent essentially unaffected, substantially unaffected, or partially unaffected.

As used herein, the terms "suppress," "repress," "downregulate," and "silence," when referring to the expression or activity of a nucleic acid molecule in a cell, are used equivalently herein and mean that the level of expression or activity of the nucleic acid molecule in an organism or a cell after applying a method of the present disclosure is lower than its expression or activity in the organism or cell before applying the method, or compared to a control organism or cell lacking a nucleic acid molecule as disclosed herein.

As used herein, a "suppression," "repression," or "downregulation" of the level or activity of an agent such as a protein, mRNA, or RNA means that the level or activity is reduced relative to a substantially identical plant, part of a plant, or plant cell grown under substantially identical conditions, lacking a nucleic acid molecule as disclosed herein. As used herein, "suppression," "repression," or "downregulation" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell or organism lacking a nucleic acid molecule as disclosed herein.

The term "plant" as used herein encompasses whole plants, ancestors and progeny of the plants and plant parts, including seeds, shoots, stems, roots (including tubers), and isolated plant cells, tissues and organs. The plant may be in any form including, but not limited to, suspension cultures, endosperm, embryos, meristematic regions, callus tissue, leaves, gametophytes, sporophytes, pollen, and microspores. It will be appreciated, that the plant or seed thereof may be transgenic plants.

As used herein, the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this embodiment of the present disclosure may comprise a particular type of a plant cell or a plurality of different types of plant cells. It should be noted that optionally plant cultures featuring a particular type of plant cell may be originally derived from a plurality of different types of such plant cells. In certain embodiments according to the present disclosure, the plant cell is a non-sexually reproducing plant cell. In other aspects, a plant cell of the present disclosure is a non-photosynthetic plant cell.

The processing of a dsRNA molecule as disclosed herein can be monitored using any methods or systems known in the art. In one aspect, the processing of a dsRNA molecule as disclosed herein is monitored in wheat germ extract (e.g., Promega Catalog #L4380). In another aspect, the processing of a dsRNA molecule as disclosed herein is monitored in plant protoplasts. In a further aspect, the processing of a dsRNA molecule as disclosed herein is monitored in a plant or parts thereof selected from the group consisting of suspension cultures, embryos, meristematic regions, calli, leaves, roots, shoots, flowers, fruits, seeds, gametophytes, sporophytes, pollen, and microspores.

In one aspect, the instant disclosure provides a double-stranded RNA (dsRNA) molecule comprising a). a first strand comprising a nucleotide sequence that is essentially identical to at least 18 consecutive nucleotides of a target nucleotide sequence; and b). a second strand comprising in the 5' to 3' direction, a 5'-overhang, a nucleotide sequence that is essentially complementary to the first strand, and a 2 nucleotide 3'-overhang, wherein the 5'-overhang is at least 5 nucleotides in length.

In some embodiments, the 5'-overhang of the second strand has a high GC content. In some embodiments, the 5'-overhang of the second strand is 5 nucleotides in length. In one embodiment, the 5'-overhang has the sequence GCGCG. In one embodiment, the 2 nucleotide 3'-overhang of the second strand has the sequence UA.

In some embodiments, the first strand further comprises the nucleotides GCCAC located 3' to the nucleotide sequence that is essentially identical to at least 18 consecutive nucleotides of the target nucleotide sequence. In some embodiments, the first strand further comprises a 5' G. In a further embodiment, the 5' G is not identical to the target nucleotide sequence.

In one embodiment, the dsRNA molecule of of the present disclosure comprises sequences selected from: a. the 5'-overhang of the second strand having a high GC content; b. the 5'-overhang of the second strand that is 5 nucleotides in length; c. the 5 nucleotide 5'-overhang of the second strand having the sequence GCGCG; d. the 2 nucleotide 3'-overhang of the second strand having the sequence UA; e. the first strand further comprising the nucleotides GCCAC located 3' to the nucleotide sequence that is essentially identical to at least 18 consecutive nucleotides of the target nucleotide sequence; f. the 3' end of the first strand having a high GC content; g. the 3' end of the first strand that is not identical to the target nucleotide sequence; and h. any combination thereof.

In some embodiments, the 2 nucleotide 3'-overhang in the second strand comprises at least one modification that improves stability of the dsRNA molecule. In some embodiments, the 2 nucleotide 3'-overhang comprises at least one modification selected from the group consisting of methylation, phosphorothioate addition, locked nucleic acids (LNAs), and any combination thereof.

In some embodiments, the target nucleotide sequence is a coding region of a mRNA, a 5' untranslated region, a 3' untranslated region, an intron, a promoter, an enhancer, a terminator, an rRNA, a tRNA, a small nuclear RNA (snRNA), a small nucleolar RNA (snoRNA), a non-coding RNA involved in RNA interference, and any combination thereof.

In some embodiments, the first strand of the dsRNA molecule further comprising in the 5' to 3' direction: a). a first sequence that is essentially identical to at least 18 consecutive nucleotides of a first target nucleotide sequence; and b). a second sequence that is essentially identical to at least 18 consecutive nucleotides of a second target nucleotide sequence. In some embodiments, the first target nucleotide sequence and second target nucleotide sequence are from different genes. In other embodiments, the first target nucleotide sequence and second target nucleotide sequence are from the same gene. In some embodiments, the first and second target nucleotide sequences are identical. In some embodiments, the first target nucleotide sequence and second target nucleotide sequence are non-contiguous sequences of the same gene. In some embodiments, the first strand comprises one or more As between the first and second sequence. In one embodiment, the second sequence comprises a 5' G. In a further embodiment, the second sequence comprises a 5' GUA. In another embodiment, the second sequence comprises a 5' GAA. In one embodiment, the second sequence comprises a 3' AA. In some embodiments, the the second sequence of the dsRNA molecule comprises a. a 5' G; b. a 5' GUA; c. a 5' GAA; d. a 3' AA; or e. any combination thereof.

In some embodiments, the 3' end of the first strand has a high GC content. In some embodiments, the 3' end of the first strand is not identical to the target nucleotide sequence.

In one aspect, the dsRNA molecule is processed to produce 21, 22, 23, and/or 24 nucleotide siRNAs. In some embodiments, the first and the second sequences in the first strand are 21 nucleotides in length.

In some embodiments, the first strand of the dsRNA further comprises a third sequence that is essentially identical to at least 18 consecutive nucleotides of a third target nucleotide sequence. In some embodiments, the first strand of the dsRNA further comprises a fourth sequence that is essentially identical to at least 18 consecutive nucleotides of a fourth target nucleotide sequence. In some embodiments, the first strand of the dsRNA further comprises a fifth sequence that is essentially identical to at least 18 consecutive nucleotides of a fifth target nucleotide sequence. In some embodiments, the first strand of the dsRNA further comprises a sixth sequence that is essentially identical to at least 18 consecutive nucleotides of a sixth target nucleotide sequence. In some embodiments, the first strand of the dsRNA further comprises a seventh sequence that is essentially identical to at least 18 consecutive nucleotides of a seventh target nucleotide sequence. In some embodiments, the first strand of the dsRNA further comprises a eighth sequence that is essentially identical to at least 18 consecutive nucleotides of a eighth target nucleotide sequence.

In some embodiments, the first strand of the dsRNA comprises multiple target-specific sequences that are essentially identical to at least 18 consecutive nucleotides of multiple target nucleotide sequences. In some embodiments, at least two, at least three, at least four, at least five, or at least six of the multiple target nucleotide sequences are from different genes. In some embodiments, at least two, at least three, at least four, at least five, or at least six of the multiple target nucleotide sequences are from the same gene.

In another aspect, the instant disclosure provides a dsRNA molecule comprising: a). a first strand comprising in the 5' to 3' direction, i). a first nucleotide sequence that is identical to at least 18 consecutive nucleotides of a first target-nucleotide sequence; ii). a second nucleotide sequence comprising 2 or more As; and iii). a third nucleotide sequence that is identical to at least 18 consecutive nucleotides of a second targeted nucleotide sequence or at least 18 consecutive nucleotides of the first target nucleotide sequence; and b). a second strand comprising in the 5' to 3' direction, a 5 nucleotide 5'-overhang, a nucleotide sequence that is complementary to the first strand, and a 2 nucleotide 3'-overhang. In some embodiments, the 5 nucleotide 5'-overhang has a high GC content. In one embodiment, the 5 nucleotide 5'-overhang has the sequence GCGCG. In one embodiment, the 2 nucleotide 3'-overhang has the sequence UC. In one embodiment, the first strand further comprises the nucleotides GCCAC located 3' to the third nucleotide sequence. In some embodiments, the first and the second target nucleotide sequences are selected from a coding region of a mRNA, a 5' untranslated region, a 3' untranslated region, an intron, a promoter, an enhancer, a terminator, an rRNA, a tRNA, a small nuclear RNA (snRNA), a small nucleolar RNA (snoRNA), a non-coding RNA involved in RNA interference, and any combination thereof. In some embodiments, the first target nucleotide sequence and the second target nucleotide sequence are from different genes.

In some embodiments, the first target nucleotide sequence and the second target nucleotide sequence are from the same gene. In some embodiments, the first and second target nucleotide sequences are identical. In some embodiments, the 2 nucleotide 3'-overhang in the second strand comprises at least one modification that improves stability of the dsRNA molecule. In some embodiments, the 2 nucleotide 3'-overhang comprises at least one modification selected from the group consisting of methylation, phosphorothioate addition, locked nucleic acids (LNAs), and any combination thereof. Modifications can be introduced to the most 5' nucleotide for both strands and to all nucleotides being part of the overhangs. In one embodiment, all five nucleotides representing the 5' end of the antisense strand (5'-GCGCG-3') can be modified to enhance stability.

In some embodiments, the dsRNA molecule in the instant disclosure comprises a concatemer of identical trigger sequences. In some embodiments, the dsRNA molecule comprises at least two, at least three, at least four, at least five, at least six, at least seven, or at least eight of identical trigger sequences.

In one aspect, the dsRNA molecule is processed to produce 21, 22, 23, and/or 24 nucleotide siRNAs. In some embodiments, the first and the third sequences in the first strand are 21 nucleotides in length.

In a further aspect, the instant disclosure also provides a composition comprising a dsRNA molecule disclosed herein.

In one aspect, the instant disclosure provides a method of regulating expression of at least one target gene, comprising applying onto the surface of a plant or plant part a composition comprising a dsRNA molecule disclosed herein, wherein the dsRNA molecule comprises a first strand comprising a nucleotide sequence that is essentially identical to at least 18 consecutive nucleotides of the target gene. In one aspect, the dsRNA molecule transfers from the surface of the plant or plant part into a cell of the plant or plant part.

In some embodiments, the first strand of the dsRNA molecule comprises a first nucleotide sequence that is essentially identical to at least 18 consecutive nucleotides of a first target gene and a second nucleotide sequence that is essentially identical to at least 18 consecutive nucleotides of a second target gene. In another embodiment, the first strand of the dsRNA molecule further comprises a third nucleotide sequence that is essentially identical to at least 18 consecutive nucleotides of a third target gene. In a further embodiment, the first strand of the dsRNA molecule further comprises a fourth nucleotide sequence that is essentially identical to at least 18 consecutive nucleotides of a fourth target gene.

In some embodiments, the first strand of the dsRNA molecule comprises multiple target-specific sequences that are essentially identical to at least 18 consecutive nucleotides of multiple target nucleotide sequences. In some embodiments, at least two, at least three, at least four, at least five, or at least six of the multiple target nucleotide sequences are from different genes. In some embodiments, at least two, at least three, at least four, at least five, or at least six of the multiple target nucleotide sequences are from the same gene.

In some embodiments, the dsRNA molecule suppresses the expression of at least one, at least two, at least three, at least four, at least five, or at least six target genes.

In another aspect, the instant disclosure also provides a method of improving the efficiency of a dsRNA molecule in producing desired small RNAs in a plant or plant part, comprising providing to the plant or plant part a dsRNA molecule disclosed herein, wherein the production of the 21-24 nucleotide small RNAs is directionally biased towards the 3' end of the second strand of the dsRNA molecule. In one embodiment, the instant disclosure provides a method of improving the efficiency of a dsRNA molecule in producing desired small RNAs in a plant or plant part, comprising providing to the plant or plant part a dsRNA molecule comprising: a. a first strand comprising a nucleotide sequence that is essentially identical to at least 18 consecutive nucleotides of a target nucleotide sequence; and b. a second strand comprising in the 5' to 3' direction, a 5'-overhang, a nucleotide sequence that is essentially complementary to the first strand, and a 2 nucleotide 3'-overhang, wherein the 5'-overhang is at least 5 nucleotides in length, wherein the dsRNA molecule is processed to produce 21, 22, 23, and/or 24 nucleotide siRNAs, and wherein the production of the 21-24 nucleotide small RNAs is directionally biased towards the 3' end of the second strand of the dsRNA molecule.

In another aspect, the instant disclosure provides a plant, plant part, or seed comprising a dsRNA molecule disclosed herein, wherein the dsRNA molecule is exogenous to the plant, plant part, or seed. In one aspect, the dsRNA molecule suppresses the expression of at least one, at least two, at least three, or at least four target genes in the plant, plant part, or seed.

The instant disclosure provides a directional trigger comprising an exogenous dsRNA molecule having a preferential directionality when processed into sRNAs by a Dicer-like protein. In one aspect, a directional trigger of the instant disclosure comprises a 3' overhang. In another aspect, a directional trigger of the instant disclosure comprises a 5' overhang. In a further aspect, a directional trigger has a 3' overhang and a 5' overhang on the sense strand. In another aspect, a directional trigger has a 3' overhang and a 5' overhang on the antisense strand.

In one aspect, a directional trigger as disclosed herein has a pre-programmed processing pattern for generating sRNAs where sRNA processing starts from an end comprising a 3' overhang and continues in a phased manner with a about 21-nucleotide phase. In a further aspect, a directional trigger is capable of producing one or more sRNA duplexes that have strand-selectivity by preferentially having their antisense strands as guide strands. A guide strand of a sRNA duplex is the strand which is loaded into an RNA-induced silencing complex (RISC) and guides the recognition of a complementary mRNA molecule (e.g., target mRNA molecule) to trigger subsequent silencing.

In one aspect, a directional trigger as disclosed herein comprises two or more target-specific sequences that, when the directional trigger is cleaved by a Dicer-like protein, yield the same number of sRNAs, each of which has one target-specific sequence. In one aspect, two or more target-specific sequences are immediately adjacent to each other in a directional trigger. In one aspect, two or more target-specific sequences are not adjacent in a directional trigger. In one aspect, two or more target-specific sequences are not contiguous in a directional trigger. In one aspect, two or more target-specific sequences of a directional trigger are from two or more different genes. In another aspect, two or more target-specific sequences in a directional trigger are derived from a same gene but non-contiguous in that gene. In a further aspect, two or more target-specific sequences of a directional trigger have essentially identical sequences. In another aspect, a directional trigger further comprises one or more AU-rich linker sequences adjoining two or more target-specific sequences.

In one aspect, a dsRNA molecule or directional trigger as disclosed herein can adopt a stem-loop configuration, which comprises a 3' initiator overhang but lacks a 5' blocker overhang. In another aspect, a dsRNA molecule or directional trigger as disclosed herein is not from a viral vector. In a further aspect, a dsRNA molecule or directional trigger as disclosed herein is not produced from a natural viral infection.

In one aspect, a dsRNA molecule or directional trigger as disclosed herein produces at least one, two, three, four, or five siRNAs (small interfering RNA). In one aspect, a dsRNA molecule or directional trigger as disclosed herein produces at least one, two, three, four, or five miRNAs (microRNAs). In one aspect, a dsRNA molecule or directional trigger as disclosed herein produces at least one, two, three, four, or five ta-siRNAs (trans activating siRNA). In one aspect, a dsRNA molecule or directional trigger as disclosed herein produces at least one, two, three, four, or five activating RNAs (RNAas). In one aspect, a dsRNA molecule or directional trigger as disclosed herein produces at least one, two, three, four, or five anti-sense siRNAs. In one aspect, a dsRNA molecule or directional trigger as disclosed herein produces at least one, two, three, four, or five hc-siRNAs (heterochromatic siRNAs). In one aspect, a dsRNA molecule or directional trigger as disclosed herein produces at least one, two, three, four, or five cis-acting siRNAs. In one aspect, a dsRNA molecule or directional trigger as disclosed herein produces at least one, two, three, four, or five lmiRNAs (long miRNAs). In one aspect, a dsRNA molecule or directional trigger as disclosed herein produces at least one, two, three, four, or five lsiRNAs (long siRNAs). In one aspect, a dsRNA molecule or directional trigger as disclosed herein produces at least one, two, three, four, or five easiRNAs (epigenetically activated siRNAs). In another aspect, a dsRNA molecule or directional trigger as disclosed herein produces at least one, two, three, four, or five sRNAs selected from the group consisting of siRNA, miRNA, ta-siRNA, RNAa, anti-sense siRNA, hc-siRNA, cis-acting siRNA, lmiRNA, lsiRNA, easiRNA and any combinations thereof.

A dsRNA molecule or directional trigger of the instant disclosure can be of variable length. In one aspect, each strand of a dsRNA molecule or directional trigger as disclosed herein has a length from about 20 to about 1000 nucleotides. In one aspect, each strand of a dsRNA molecule or directional trigger as disclosed herein has a length from about 25 to about 1000, from about 30 to about 1000, from about 35 to about 1000, from about 40 to about 1000, from about 45 to about 1000, from about 55 to about 1000, from about 60 to about 100, from about 65 to about 1000, from about 70 to about 1000, from about 75 to about 1000, from about 80 to about 1000, from about 85 to about 1000, from about 90 to about 1000, from about 95 to about 1000, from about 100 to about 1000, from about 150 to about 1000, from about 200 to about 1000, from about 250 to about 1000, from about 300 to about 1000, from about 350 to about 1000, from about 400 to about 1000, from about 500 to about 1000, from about 600 to about 1000, from about 700 to about 1000, from about 800 to about 1000, or from about 900 to about 1000 nucleotides.

In one embodiment, one strand of a dsRNA molecule or directional trigger has a length from about 20 to about 200, from about 25 to about 200, from about 30 to about 200, from about 35 to about 200, from about 40 to about 200, from about 45 to about 200, from about 50 to about 200, from about 55 to about 200, from about 60 to about 200, from about 65 to about 200, from about 70 to about 200, from about 75 to about 200, from about 80 to about 200, from about 85 to about 200, from about 90 to about 200, from about 95 to about 200, from about 100 to about 200, from about 105 to about 200, from about 110 to about 200, from about 120 to about 200, from about 130 to about 200, from about 140 to about 200, or from about 150 to about 200 nucleotides.

In another embodiment, one strand of a dsRNA molecule or directional trigger as disclosed herein has a length from about 20 to about 190, from about 25 to about 180, from about 30 to about 170, from about 35 to about 160, from about 40 to about 150, from about 45 to about 140, from about 50 to about 130, from about 55 to about 120, from about 60 to about 110, from about 65 to about 100, from about 70 to about 90, or from about 75 to about 80 nucleotides.

In one embodiment, one strand of a dsRNA molecule or directional trigger as disclosed herein has a length from about 40 to about 100, from about 45 to about 100, from about 50 to about 100, from about 55 to about 100, from about 60 to about 100, from about 65 to about 100, from about 70 to about 100, from about 75 to about 100, from about 80 to about 100, from about 85 to about 100, or from about 90 to about 100 nucleotides.

In another embodiment, one strand of a dsRNA molecule or directional trigger as disclosed herein has a length from about 40 to about 95, from about 40 to about 90, from about 40 to about 85, from about 40 to about 80, from about 40 to about 75, from about 40 to about 70, from about 40 to about 65, from about 40 to about 60, from about 40 to about 55, or from about 40 to about 50 nucleotides.

In a further embodiment, one strand of a dsRNA molecule or directional trigger as disclosed herein has a length from about 45 to about 95, from about 50 to about 90, from about 55 to about 85, from about 60 to about 80, or from about 65 to about 75.

In one embodiment, one strand of a dsRNA molecule or directional trigger as disclosed herein has a length from about 45 to about 75 nucleotides.

In another embodiment, one strand of a dsRNA molecule or directional trigger as disclosed herein has a length of about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 350, 400, 450, 500, 550, 600, 650, 700, 750, 800, 850, 900, 950, or 1000 nucleotides.

In one embodiment, a dsRNA molecule or directional trigger as disclosed herein comprises 2, 3, 4, 5, or 6 sRNA trigger sequences each encoding one sRNA duplex.

In one aspect, a dsRNA molecule or directional trigger as disclosed herein can comprises 1, 2, 3, 4, 5, 6, 7, 8, 9, 10 or more mismatch regions. A mismatch region can have 1, 2, 3, 4, 5, 6, 7, 8, 9, 10, 11, 12, 13, 14, 15, 16, 17, 18, 19, 20 or more sets of mismatched nucleotides. In another aspect, a dsRNA molecule or directional trigger as disclosed herein molecule can comprises one or more bulges of 1, 2, 3, 4 or more nucleotides.

In one embodiment, a dsRNA molecule or directional trigger of the instant disclosure has a single target gene. In another embodiment, a dsRNA molecule or directional trigger as disclosed herein has two or more distinct target genes. In one embodiment, two or more sRNA duplexes encoded by a dsRNA molecule or directional trigger of the instant disclosure target a same gene. A directional trigger as disclosed herein which encodes two or more distinct sRNAs targeting a same target gene can have a higher silencing efficiency compared to a non-directional trigger comprising similar target specific sequences with neither a 3' initiator overhang nor a 5' blocker overhang. Two silencing molecules' efficiencies can be compared by any available methods, for example, measuring minimum molecule concentrations needed to observe a set amount (e.g., 20%) of target gene expression reduction, or measuring percent reductions of target gene expression by applying a set amount (e.g., 250 pmol) of silencing molecules. One of ordinary skill in the art understands that both the set amount of target gene expression reduction and the set amount of silencing molecules can be varied when assessing the efficiency of different sets of molecules.

In another embodiment, two or more sRNA duplexes encoded by a dsRNA molecule or directional trigger of the instant disclosure do not target the same gene. In a further embodiment, each of two or more sRNA duplexes encoded by a dsRNA molecule or directional trigger of the instant disclosure targets a distinct gene. In another embodiment, a dsRNA molecule or directional trigger as disclosed herein targets two or more genes from the same gene family. In another embodiment, a dsRNA molecule or directional trigger as disclosed herein targets two or more paralogous genes. In another embodiment, a dsRNA molecule or directional trigger as disclosed herein targets two or more genes which are in a common metabolic pathway, and therefore increases the probability of disrupting the metabolic pathway. In another embodiment, a dsRNA molecule or directional trigger as disclosed herein targets two, three, or more separate herbicide-resistant genes.

In one embodiment, a dsRNA molecule or directional trigger as disclosed herein can comprise one or more target-specific sequences essentially identical or identical to a sequence (which can be coding sequence or non-coding sequence) selected from the group consisting of a plant endogenous gene sequence, a plant phytopathogen gene sequence, a plant viral gene sequence, a plant insect gene sequence, and combinations thereof. In one embodiment, a dsRNA molecule or directional trigger as disclosed herein can induce systemic regulation or suppression of an endogenous gene in a plant.

In one embodiment, a dsRNA molecule or directional trigger as disclosed herein has one or more target genes of interest which encode herbicide-tolerance proteins. Examples of a protein that provides tolerance to an herbicide include e.g., a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase. Examples of nucleic acids encoding proteins conferring tolerance to herbicides include 5-enolpyruvylshikimate-3-phosphate synthases (EPSPS; see, e.g., U.S. Pat. Nos. 5,627,061, 5,633,435 RE39,247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U.S. Patent Application Publication 2004/0177399), glyphosate-N-acetyl transferase (GAT; U.S. Pat. No. 7,714,188)

conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719,046); 32 kDa photosystem II polypeptide (psbA) for conferring tolerance to triazine herbicides (Hirschberg et al., 1983, Science, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtI) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268,549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (PCT International Application Publication WO05107437); a serine hydroxymethyltransferase (U.S. Patent Application Publication 2008/0155716), a glufosinate-tolerant glutamine synthase (U.S. Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase 1× inhibitors (such as pyraflufen and flumiclorac). All foregoing cited patents and patent application publications, including sequences of the nucleic acids encoding herbicide-tolerance proteins and sequences of the herbicide-tolerance proteins disclosed therein, are incorporated herein by reference in their entireties.

In another embodiment, a dsRNA molecule or directional trigger as disclosed herein has one or more target genes of interest which are essential genes. Essential genes are genes necessary for sustaining cellular life or to support reproduction of an organism. Exemplary essential genes include genes involved in DNA or RNA replication, gene transcription, RNA-mediated gene regulation, protein synthesis, energy production, and cell division. One example of a compendium of essential genes is described in Zhang et al. (2004) Nucleic Acids Res., 32:D271-D272 (listing 777 essential genes for *Arabidopsis thaliana*). Further examples of essential genes include translation initiation factor (TIF) and ribulose-1,5-bisphosphate carboxylase oxygenase (RuBisCO). In further aspects, target genes of interest can be genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

In some embodiments, a target-specific sequence comprised in a nucleic acid molecule as disclosed herein has 100% sequence complementarity or at least about 83, 84, 85, 86, 87, 88, 89, 90, 91, 92, 93, 94, 95, 96, 97, 98, or 99% sequence complementarity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a target-specific sequence comprised in a nucleic acid molecule as disclosed herein has 100% sequence complementarity to one allele or one family member of a given target gene (coding or non-coding sequence of a gene). In some embodiments, a target-specific sequence comprised in a nucleic acid molecule as disclosed herein has at least about 83, 84, 85, 86, 87, 88, 89, 90, 91, 92, 93, 94, 95, 96, 97, 98, or 99% sequence complementarity to multiple alleles or family members of a given target gene. In some embodiments, a target-specific sequence comprised in a nucleic acid molecule has 100% sequence complementarity to multiple alleles or family members of a given target gene.

In some embodiments, a target-specific sequence comprised in a nucleic acid molecule as disclosed herein has 100% sequence identity or at least about 83, 84, 85, 86, 87, 88, 89, 90, 91, 92, 93, 94, 95, 96, 97, 98, or 99% sequence identity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a target-specific sequence comprised in a nucleic acid molecule as disclosed herein has 100% sequence identity with one allele or one family member of a given target gene (coding or non-coding sequence of a gene). In some embodiments, a target-specific sequence comprised in a nucleic acid molecule as disclosed herein has at least about 83, 84, 85, 86, 87, 88, 89, 90, 91, 92, 93, 94, 95, 96, 97, 98, or 99% sequence identity with multiple alleles or family members of a given target gene. In some embodiments, a target-specific sequence comprised in a nucleic acid has 100% sequence identity with multiple alleles or family members of a given target gene.

In one aspect, a dsRNA molecule or directional trigger of the instant disclosure can effect regulation of gene expression (e.g., suppression) for a time period of various length. In one aspect, a dsRNA molecule or directional trigger as disclosed herein is effective for a period during the life of a treated plant of at least 1, 2, 3, 4, 5, 6, 7, 8, 9, 10 or more weeks. In another aspect, a dsRNA molecule or directional trigger as disclosed herein can be applied to a seed and subsequently regulate gene expression at any stage after the seed germinates. A seed treated with a dsRNA molecule or directional trigger as disclosed herein can be stored for a period of any length, e.g., 2, 4, or 6 weeks, or 2, 3, 4, 5, 6, 7, 8, 9, 10, 11, 12, 13, 14, 15, 16, 17, 18, 19, 20 months, or 2, 3, 4, 5, 6, 7 or more years, while retaining effects of the dsRNA molecule or directional trigger.

A dsRNA molecule or directional trigger of the instant disclosure can comprise a 3' overhang of variable length. In one aspect, a dsRNA molecule or directional trigger as disclosed herein comprises a 3' overhang of 1, 2, 3, 4, 5, 6, 7, 8, 9, 10 or more nucleotides. In another aspect, a 3' overhang of a dsRNA molecule or directional trigger as disclosed herein comprise a non-target-specific sequence. In another aspect, a 3' overhang of a dsRNA molecule or directional trigger as disclosed herein comprise a synthetic sequence. In one aspect, a 3' overhang of a dsRNA molecule or directional trigger as disclosed herein comprises a sequence of 5'-Uracile-Adenine-3'. In another aspect, a 3' overhang of a dsRNA molecule or directional trigger as disclosed herein comprises a sequence of 5'-Uracile-Uracile-3'. Without being bound to any scientific theory or mechanism, siRNAs with 3' overhanging UU di-nucleotides were observed to be the most effective in triggering silencing. See Elbashir et al., Functional anatomy of siRNA for mediating efficient RNAi in *Drosophila melanogaster* embryo lysate, EMBO J, 20:6877-6888(2001); see also Strapps et al. The siRNA sequence and guide strand overhangs are determinants of in vivo duration of silencing, Nucleic Acids Research, 38(14):4799-97(2010). In another aspect, a 3' overhang of a dsRNA molecule or directional trigger as disclosed herein does not comprise a Guanine residue. Without being bound to any scientific theory or mechanism, RNase may cleave a siRNA at a single-stranded Guanine residue. In another aspect, the first non-overhung nucleotide immediately next to a 3' overhang of a dsRNA molecule or directional trigger as disclosed herein comprise a Cytosine. In a further aspect, a 3' overhang end of any nucleic acid molecule as disclosed herein can be substituted or combined with a frayed end.

In one aspect, a dsRNA molecule or directional trigger of the instant disclosure is diced by a Dicer-like protein preferentially at a distance of about 21 nucleotides from the terminus of a 3' overhang end creating a first sRNA duplex, wherein dicing of the dsRNA molecule or directional trigger continues in the same orientation at an interval length of about 21 nucleotides generating a second sRNA duplexes, and both the first and second sRNA duplexes are about 21 nucleotides long with a double-stranded region of about 19 nucleotides and a 2-nucleotide 3' overhang at both ends.

In one aspect, a dsRNA molecule or directional trigger of the instant disclosure is diced by a Dicer-liker protein preferentially at a distance of about 21 nucleotides from an end with a 3' overhang creating a first sRNA duplex, wherein dicing of the dsRNA molecule or directional trigger continues in the same orientation at an interval length of about 21 nucleotides generating one or more successive sRNA duplexes, and wherein the first and one or more successive sRNA duplexes are about 21 nucleotides long with a double-stranded region of about 19 nucleotides and a 2-nucleotide 3' overhang at both ends. In one aspect, a dsRNA molecule or directional trigger of the instant disclosure can be diced into at least 2, 3, 4, 5, 6, 7, 8, 9, or 10 or more successive sRNA duplexes of about 21 nucleotides with a double-stranded region of about 19 nucleotides and a 2-nucleotide 3' overhang at both ends.

A dsRNA molecule or directional trigger of the instant disclosure can comprise at one end a 5' overhang of variable length which, without being to any theory or mechanism, substantially disfavors or essentially precludes a Dicer-liker protein to start dicing from the that end. In one aspect, a dsRNA molecule or directional trigger as disclosed herein comprise a 5' overhang of 1, 2, 3, 4, 5, 6, 7, 8, 9, 10 or more nucleotides. In another aspect, a 5' overhang of a dsRNA molecule or directional trigger as disclosed herein comprise a non-target-specific sequence. In another aspect, a 5' overhang of a dsRNA molecule or directional trigger as disclosed herein comprise a synthetic sequence. In a further aspect, a 5' overhang of a dsRNA molecule or directional trigger as disclosed herein comprises a sequence of 5'-Guanine-Guanine-Guanine-3'. In a further aspect, a 5' overhang end of any nucleic acid molecule as disclosed herein can be substituted or combined with a frayed end.

In one aspect, a dsRNA molecule or directional trigger as disclosed herein comprises, immediately next to a 5' overhang, a double-stranded region having a non-target-specific sequence of variable length. In one aspect, a 5' overhang-adjacent non-target-specific double-stranded region comprises a length selected from the group consisting of 2, 3, 4, 5, 6, 7, 8, 9, 10, 11, 12, 13, 14, 15 or more nucleotides.

In one aspect, a dsRNA molecule or directional trigger as disclosed herein comprises one or more modified nucleotides. In another aspect, a 5' overhang of a dsRNA molecule or directional trigger as disclosed herein comprises 1, 2, 3, 4, 5, 6, 7, 8, 9, 10 or more deoxyribonucleotides. In another aspect, a 5' overhang of a dsRNA molecule or directional trigger as disclosed herein is solely composed of deoxyribonucleotides.

A dsRNA molecule or directional trigger of the instant disclosure can also comprise a linker sequence of variable length adjoining two adjacent sRNA trigger sequences. In one aspect, a linker sequence as disclosed herein is about 1, 2, 3, 4, 5, 6, 7, 8, 9, 10, 11, 12, 13, 14, 15 or more nucleotides long.

In one aspect, a linker sequence as disclosed herein comprises a non-target-specific sequence. In another aspect, a linker sequence as disclosed herein comprises a synthetic sequence. In another aspect, a linker sequence as disclosed herein is rich in Adenine or Uracil. In one aspect, at least 40%, 50%, 60%, 70%, 80%, 90%, or 100% of the sequence of a linker used here comprises Adenine (A) or Uracil (U). In another aspect, a linker sequence as disclosed herein comprises a sequence of 5'-AAAAG-3' (SEQ ID NO:80).

A dsRNA molecule or directional trigger of the instant disclosure can further be a strand-selective trigger or chimera encoding one or more sRNA duplexes which preferentially have their antisense strands as guide strands. In one aspect, at least a most abundant sRNA duplex produced from a dsRNA molecule or directional trigger of the instant disclosure preferentially have their antisense strands as guide strands. In another aspect, both a most abundant and a second most abundant sRNA duplex produced from a dsRNA molecule or directional trigger of the instant disclosure preferentially have their antisense strands as guide strands. In a further aspect, both a most abundant, a second most abundant, and a third most abundant sRNA duplex produced from a dsRNA molecule or directional trigger of the instant disclosure preferentially have their antisense strands as guide strands. In a further aspect, both a most abundant, a second most abundant, a third most abundant, a fourth most abundant sRNA duplex produced from a dsRNA molecule or directional trigger of the instant disclosure preferentially have their antisense strands as guide strands. A guide strand of a sRNA duplex is the strand which is loaded into a RNA-induced silencing complex (RISC) to guide the recognition of a complementary mRNA molecule and to trigger subsequent silencing.

In one aspect, at least 30%, 35%, 40%, 45%, 50%, 55%, 60%, 65%, 70%, 75%, 80%, 85%, 90%, 95%, 99% or more sRNA duplexes encoded by a strand-selective trigger as disclosed herein have their antisense strands as guide strands. In another aspect, less than 10%, 5%, 4%, 3%, 2%, 1%, 0.9%, 0.8%, 0.7%, 0.6%, 0.5%, 0.4%, 0.3%, 0.2%, or 0.1% of sRNA duplexes encoded by a strand-selective trigger as disclosed herein have their sense strands as guide strands.

In one aspect, a sRNA duplex encoded by a dsRNA molecule or directional trigger as disclosed herein comprises a Uracil or Cytosine at the 5' end of its antisense strand. In another aspect, at least 20%, 25%, 30%, 35%, 40%, 45%, 50%, 55%, 60%, 65%, 70%, 75%, 80%, 85%, 90%, 95%, 98%, 99%, or 99.5% of sRNA duplexes encoded by a dsRNA molecule or directional trigger as disclosed herein comprise a Uracil or Cytosine at the 5' end of their antisense strands.

In another aspect, a sRNA duplex encoded by a dsRNA molecule or directional trigger of the instant disclosure comprises a Guanine at the 5' end of its sense strand. In a further aspect, a sRNA duplex encoded by a dsRNA molecule or directional trigger of the instant disclosure comprises a Uracil or Cytosine at the 5' end of its antisense strand, and a Guanine at the 5' end of its sense strand. In another aspect, a dsRNA molecule or directional trigger as disclosed herein comprises a Uracil or Cytosine at position 21 on a same strand bearing a 2-nucleotide 3' overhang, where position 21 is the 21st nucleotide relative to the terminus of the 2-nucleotide 3' overhang.

A dsRNA molecule or directional trigger of the instant disclosure can be processed into a more homogenous population of sRNAs compared to a non-directional trigger. In one aspect, a dsRNA molecule or directional trigger as disclosed herein produce sRNAs predominately originating from a specific region or strand of the dsRNA molecule or directional trigger. In one aspect, sRNA produced by a dsRNA molecule or directional trigger as disclosed herein originate primarily from the 3' end of the antisense strand of the dsRNA molecule or directional trigger. In another aspect, at least 20%, 25%, 30%, 35%, 40%, 45%, 50%, 55%, 60%, 65%, 70%, 75%, 80%, 85%, 90%, 95%, 98%, 99%, or 99.5% of total sRNAs produced by a dsRNA molecule or directional trigger as disclosed herein originate primarily from the 3' end of the antisense strand of the dsRNA molecule or directional trigger. In a further aspect, at least 20%, 25%, 30%, 35%, 40%, 45%, 50%, 55%, 60%, 65%, 70%, 75%, 80%, 85%, 90%, 95%, 98%, 99%, or 99.5% of total sRNAs of 21-24nt produced by a dsRNA molecule or directional trigger as disclosed herein originate primarily from the 3' end of the antisense strand of the dsRNA molecule or directional trigger.

A dsRNA molecule or directional trigger as disclosed herein can have an increased silencing efficiency compared to a non-directional trigger comprising similar or essentially identical target specific sequences. In one aspect, a dsRNA molecule or directional trigger as disclosed herein can achieve a percent reduction of target gene expression that is similar to, substantially same or same as that achieved by a non-directional trigger when the dsRNA molecule or directional trigger is applied at a concentration of about 10%, 20%, 30%, 40%, 50%, 60%, 70%, 80%, or 90% of that of the non-directional trigger.

A dsRNA molecule or directional trigger of the instant disclosure can be applied to a plant, plant part or seed at any concentration needed to effect a desirable degree of silencing of its target(s). In one aspect, a dsRNA molecule or directional trigger as disclosed herein can result in at least a partial reduction, a substantial reduction, an effective elimination or a suppression of target gene expression when applied to a plant or seed at a concentration selected from the group consisting of less than about 100, 75, 50, 40, 30, 20, 10, 9, 8, 7, 6, 5, 4, 3, 2, 1, 0.5, 0.2, 0.1, 0.05, and 0.01 µM.

In one aspect, a dsRNA molecule or directional trigger as disclosed herein can result in at least a partial reduction, a substantial reduction, an effective elimination or a suppression of target gene expression when applied to a plant or seed at a concentration selected from the group consisting of between 0.1 and 10, between 0.2 and 10, between 0.3 and 10, between 0.4 and 10, between 0.5 and 10, between 0.6 and 10, between 0.7 and 10, between 0.8 and 10, between 0.9 and 10, between 1 and 10, between 2 and 10, between 3 and 10, between 4 and 10, between 5 and 10, between 6 and 10, between 7 and 10, between 8 and 10, and between 9 and 10 µM.

In another aspect, a dsRNA molecule or directional trigger as disclosed herein can result in at least a partial reduction, a substantial reduction, an effective elimination or a suppression of target gene expression when applied to a plant or seed at a concentration selected from the group consisting of between 0.1 and 10, between 0.2 and 9, between 0.3 and 8, between 0.4 and 7, between 0.5 and 6, between 0.6 and 5, between 0.7 and 4, between 0.8 and 3, and between 0.9 and 2 µM.

In a further aspect, a dsRNA molecule or directional trigger as disclosed herein can result in at least a partial reduction, a substantial reduction, an effective elimination or a suppression of target gene expression when applied to a plant or seed at a concentration selected from the group consisting of between 0.1 and 10, between 0.1 and 9, between 0.1 and 8, between 0.1 and 7, between 0.1 and 6, between 0.1 and 5, between 0.1 and 4, between 0.1 and 3, between 0.1 and 2, between 0.1 and 1, between 0.1 and 0.9, between 0.1 and 0.8, between 0.1 and 0.7, between 0.1 and 0.6, between 0.1 and 0.5, between 0.1 and 0.4, between 0.1 and 0.3, and between 0.1 and 0.2 µM.

In one aspect, the instant disclosure provides a dsRNA molecule, wherein the processing of a population of the dsRNA molecules into one or more 21-24 mer sRNAs preferentially starts from an end having a 3' overhang, and wherein at least 50%, 60%, 65%, 70%, 75%, 80%, 85%, 90%, or 95% of detectable 21-24 mer sRNAs processed therefrom comprise a sequence identical to a sequence of a first double-stranded portion of at least 15, 16, 17, 18, 19, 20, 21, 22, or 23 nucleotides immediately adjacent to the 3' overhang. In one aspect, the dsRNA molecule is a directional trigger. In one aspect, the 3' overhang has a length of 1, 2, or 3 nucleotides. In another aspect, the 3' overhang has a length of more than 3 nucleotides. In another aspect, the dsRNA molecule further comprises a 5' overhang. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In a further aspect, the dsRNA molecule has a length between about 45 and about 75 nucleotides. In another aspect, the dsRNA molecule further comprises two or more sRNA trigger sequences that encode the same number of sRNA duplexes, wherein the two or more sRNA trigger sequences are not found in a single naturally occurring dsRNA molecule. In another aspect, the dsRNA molecule further comprises two or more sRNA trigger sequences that encode the same number of sRNA duplexes, wherein the two or more sRNA trigger sequences are not contiguous in a single naturally occurring molecule. In another aspect, the dsRNA molecule further comprises two or more sRNA trigger sequences that encode the same number of sRNA duplexes, wherein the two or more sRNA trigger sequences are adjoined by one or more synthetic linker sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotides relative to terminus of the 3' overhang. In another aspect, wherein the dsRNA molecule further comprises a Uracil at position 20 on the same strand bearing the 3' overhang, the position 20 is the 20th nucleotides relative to terminus of the 3' overhang. In a further aspect, the 5' terminal nucleotide of the 3' overhang end of the dsRNA molecule is Guanine.

In one aspect, the instant disclosure provides a dsRNA molecule, wherein the first cleavage of the dsRNA molecule by a Dicer-like protein is at a position of about 21 to 24 nucleotides from the 3' terminus of a 3' overhang, and wherein at least 50%, 60%, 65%, 70%, 75%, 80%, 85%, 90%, or 95% of detectable 21-24 mer sRNAs processed from the population of the dsRNA molecules comprise a sequence identical to a sequence of a first double-stranded portion of at least 15, 16, 17, 18, 19, 20, 21, 22, or 23 nucleotides immediately adjacent to the 3' overhang. In one aspect, the dsRNA molecule is a directional trigger. In one aspect, the 3' overhang has a length of 1, 2, or 3 nucleotides. In another aspect, the 3' overhang has a length of more than 3 nucleotides. In another aspect, the dsRNA molecule further comprises a 5' overhang. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In a further aspect, the dsRNA molecule has a length between about 45 and about 75 nucleotides. In another aspect, the dsRNA molecule further comprises two or more sRNA trigger sequences that encode the same number of sRNA duplexes, wherein the two or more sRNA trigger sequences are not found in a single naturally occurring dsRNA molecule. In another aspect, the dsRNA molecule further comprises two or more sRNA trigger sequences that encode the same number of sRNA duplexes, wherein the two or more sRNA trigger sequences are not contiguous in a single naturally occurring molecule. In another aspect, the dsRNA molecule further comprises two or more sRNA trigger sequences that encode the same number of sRNA duplexes, wherein the two or more sRNA trigger sequences are adjoined by one or more synthetic linker sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, the instant disclosure provides a dsRNA molecule comprising a 5' overhang, wherein the first cleavage of the dsRNA molecule by a Dicer-like protein is at a position of about 21 to 24 nucleotides from the 3' terminus of the dsRNA molecule, and wherein at least 50%, 60%, 65%, 70%, 75%, 80%, 85%, 90%, or 95% of detectable 21-24 mer sRNAs processed from the population of the dsRNA molecules comprise a sequence identical to a sequence of a first double-stranded portion of at least 15, 16, 17, 18, 19, 20, 21, 22, or 23 nucleotides. In one aspect, the dsRNA molecule is a directional trigger. In one aspect, the 3'terminus comprises a 3' overhang having a length of 1, 2, or 3 nucleotides. In another aspect, the 3' overhang has a length of more than 3 nucleotides. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In a further aspect, the dsRNA molecule has a length between about 45 and about 75 nucleotides. In another aspect, the dsRNA molecule further comprises two or more sRNA trigger sequences that encode the same number of sRNA duplexes, wherein the two or more sRNA trigger sequences are not found in a single naturally occurring dsRNA molecule. In another aspect, the dsRNA molecule further comprises two or more sRNA trigger sequences that encode the same number of sRNA duplexes, wherein the two or more sRNA trigger sequences are not contiguous in a single naturally occurring molecule. In another aspect, the dsRNA molecule further comprises two or more sRNA trigger sequences that encode the same number of sRNA duplexes, wherein the two or more sRNA trigger sequences are adjoined by one or more synthetic linker sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 5' overhang, the position 21 is the 21st nucleotide relative to 3' terminus of the dsRNA molecule. In another aspect, wherein the dsRNA molecule further comprises a Uracil at position 20 on the same strand bearing the 5' overhang, the position 20 is the 20th nucleotide relative to terminus of the 3' terminus. In a further aspect, the 5' terminal nucleotide of the 3' overhang end of the dsRNA molecule is Guanine.

In one aspect, the instant disclosure provides a dsRNA molecule, wherein the processing of a population of the dsRNA molecule into one or more 21-24 mer sRNAs preferentially starts from one end of the dsRNA molecule, and wherein the most abundant detectable 21-24 mer sRNAs processed from the population of the dsRNA molecules comprise a sequence identical to a sequence of a first double-stranded portion of at least 15, 16, 17, 18, 19, 20, 21, 22, or 23 nucleotides immediately adjacent to the 3' overhang. In another aspect, the second most abundant detectable 21-24 mer sRNAs processed from a population of dsRNA molecules as disclosed herein comprise a sequence identical to a sequence immediately adjacent to the first double-stranded portion. In one aspect, the dsRNA molecule is a directional trigger. In one aspect, the 3' overhang has a length of 1, 2, or 3 nucleotides. In another aspect, the 3' overhang has a length of more than 3 nucleotides. In another aspect, the dsRNA molecule further comprises a 5' overhang. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In a further aspect, the dsRNA molecule has a length between about 45 and about 75 nucleotides. In another aspect, the dsRNA molecule further comprises two or more sRNA trigger sequences that encode the same number of sRNA duplexes, wherein the two or more sRNA trigger sequences are not found in a single naturally occurring dsRNA molecule. In another aspect, the dsRNA molecule further comprises two or more sRNA trigger sequences that encode the same number of sRNA duplexes, wherein the two or more sRNA trigger sequences are not contiguous in a single naturally occurring molecule. In another aspect, the dsRNA molecule further comprises two or more sRNA trigger sequences that encode the same number of sRNA duplexes, wherein the two or more sRNA trigger sequences are adjoined by one or more synthetic linker sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, the instant disclosure provides a dsRNA molecule comprising a 5' overhang at a first end of the dsRNA molecule, wherein the processing of the dsRNA molecule into one or more sRNAs preferentially starts from a second end of the dsRNA molecule, and wherein the first and second ends are opposite ends of the dsRNA molecule. In one aspect, the dsRNA molecule is a directional trigger. In one aspect, the second end comprises a 3' overhang. In one aspect, the 3' overhang has a length of 1, 2, or 3 nucleotides. In another aspect, the 3' overhang has a length of more than 3 nucleotides. In another aspect, the dsRNA molecule further comprises a 5' overhang. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In a further aspect, the dsRNA molecule has a length between about 45 and about 75 nucleotides. In another aspect, the dsRNA molecule further comprises two or more sRNA trigger sequences that encode the same number of sRNA duplexes, wherein the two or more sRNA trigger sequences are not found in a single naturally occurring dsRNA molecule. In another aspect, the dsRNA molecule further comprises two or more sRNA trigger sequences that encode the same number of sRNA duplexes, wherein the two or more sRNA trigger sequences are not contiguous in a single naturally occurring molecule. In another aspect, the dsRNA molecule further comprises two or more sRNA trigger sequences that encode the same number of sRNA duplexes, wherein the two or more sRNA trigger sequences are adjoined by one or more synthetic linker sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, the instant disclosure provides a dsRNA molecule comprising two or more sRNA trigger sequences that encode the same number of sRNAs, and one or more Adenine- or Uracil-rich linker sequences adjoining the two or more sRNA trigger sequences, wherein the two or more sRNA trigger sequences are not found in a single naturally occurring molecule. In another aspect, the dsRNA molecule has a length between about 45 and about 75 nucleotides. In one aspect, the linker sequences are about 5 nucleotides long. In one aspect, the linker sequences are synthetic sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides.

In one aspect, the instant disclosure provides a dsRNA molecule comprising two or more sRNA trigger sequences that encode the same number of sRNAs, and one or more Adenine- or Uracil-rich linker sequences adjoining the two or more sRNA trigger sequences, wherein the two or more sRNA trigger sequences are not contiguous in a single naturally occurring molecule. In another aspect, the dsRNA molecule has a length between about 45 and about 75 nucleotides. In one aspect, the linker sequences are synthetic sequences. In one aspect, the linker sequences are about 5 nucleotides long. In another aspect, the linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides.

In one aspect, the instant disclosure provides a dsRNA molecule comprising a 3' overhang and a 5' overhang, and further comprising two or more sRNA trigger sequences that encode the same number of sRNAs, wherein the two or more sRNA trigger sequences are not found in a single naturally occurring molecule. In another aspect, the dsRNA molecule has a length between about 45 and about 75 nucleotides. In one aspect, the dsRNA molecule is a directional trigger. In another aspect, the dsRNA molecule is a directional chimeric trigger. In a further aspect, the dsRNA molecule is a strand-selective chimeric trigger. In one aspect, the 3' overhang has a length of 1, 2, or 3 nucleotides. In another aspect, the 3' overhang has a length of more than 3 nucleotides. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In another aspect, the dsRNA molecule further comprises one or more synthetic linker sequences adjoining the two or more sRNA trigger sequences. In one aspect, the synthetic linker sequences are about 5 nucleotides long. In another aspect, the synthetic linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, the instant disclosure provides a dsRNA molecule comprising a 3' overhang and a 5' overhang, and further comprising two or more sRNA trigger sequences that encode the same number of sRNAs, wherein the two or more sRNA trigger sequences are not contiguous in a single naturally occurring molecule. In another aspect, the dsRNA molecule has a length between about 45 and about 75 nucleotides. In one aspect, the dsRNA molecule is a directional trigger. In another aspect, the dsRNA molecule is a directional chimeric trigger. In a further aspect, the dsRNA molecule is a strand-selective chimeric trigger. In one aspect, the 3' overhang has a length of 1, 2, or 3 nucleotides. In another aspect, the 3' overhang has a length of more than 3 nucleotides. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In another aspect, the dsRNA molecule further comprises one or more synthetic linker sequences adjoining the two or more sRNA trigger sequences. In one aspect, the synthetic linker sequences are about 5 nucleotides long. In another aspect, the synthetic linker sequences are Adenine- or Uracil-rich sequences. In one aspect, the two or more sRNA duplexes target a same gene. In another aspect, the two or more sRNA duplexes do not target a same gene. In a further aspect, each of the two or more sRNA duplexes targets a distinct gene. In one aspect, the guide strand of each of the two or more sRNA duplexes is from the same strand of the dsRNA molecule. In another aspect, the guide strand of each of the two or more populations of sRNAs is from the antisense strand of the dsRNA molecule. In a further aspect, the guide strand of each of the two or more sRNA duplexes is from opposite strands of the dsRNA molecule. In a further aspect, each of the two or more sRNA trigger sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, a dsRNA molecule or directional trigger of the instant disclosure comprises one, two, three, four, five or more features selected from the group consisting of (a) two or more sRNA trigger sequences each of which encodes a sRNA, where the two or more sRNA trigger sequences are not found in a single naturally occurring molecule or not contiguous in a single naturally occurring molecule, (b) having a length between about 45 and about 75 nucleotides, (c) comprising one or more Adenine- or Uracil-rich linker sequences adjoining the two or more sRNA trigger sequences, (d) comprising a 3' overhang in the antisense strand, (e) comprising a Uracil at positions 20 and 21 in the antisense strand relative to terminus of the 3' overhang, (f) a 5' overhang of 3 to 5 nucleotides, and (g) combinations thereof.

In one aspect, a dsRNA molecule or directional trigger of the instant disclosure comprises a first end portion comprising a 3' overhang, a second end portion comprising a 5' overhang, and two or more target-specific sequences that are adjoined by one or more linker sequences. In another aspect, the dsRNA molecule has a length between about 45 and about 75 nucleotides. In one aspect, the 3' overhang has a length of 1, 2, or 3 nucleotides. In another aspect, the 3' overhang has a length of more than 3 nucleotides. In another aspect, the 5' overhang is on the same strand having the 3' overhang. In a further aspect, the 5' overhang is 3 to 5 nucleotides long. In another aspect, the 5' overhang comprises deoxyribonucleotides. In another aspect, the 5' overhang comprises one, two, or three Guanine at the terminus. In another aspect, the one or more linker sequences are synthetic sequences. In one aspect, the synthetic linker sequences are about 5 nucleotides long. In another aspect, the synthetic linker sequences are Adenine- or Uracil-rich sequences. In one aspect, the two or more target-specific sequences can be found in a naturally occurring molecule but not contiguous in that molecule. In another aspect, the two or more target-specific sequences are from different genes. In another aspect, the two or more target-specific sequences are from two different naturally occurring molecules. In one aspect, at least one of the two or more target-specific sequences has a length between about 20 and about 30 nucleotides. In a further aspect, each of the two or more target-specific sequences has a length between about 20 and about 30 nucleotides. In one aspect, the dsRNA molecule comprises a Uracil at position 21 on the same strand bearing the 3' overhang, the position 21 is the 21st nucleotide relative to terminus of the 3' overhang. In another aspect, wherein the dsRNA molecule further comprises a Uracil at position 20 on the same strand bearing the 3' overhang, the position 20 is the 20th nucleotide relative to terminus of the 3' overhang. In a further aspect, the 5' terminal nucleotide of the 3' overhang end of the dsRNA molecule is Guanine.

In one aspect, sRNAs produced by a dsRNA molecule or directional trigger as disclosed herein can regulate the expression of a target gene via any RNA silencing mechanism. Exemplary mechanisms include RNA cleavage, translation or transcription attenuation, DNA or chromatin modification.

Nucleic acid molecules of the instant disclosure can be synthesized by any synthesis method known in the art such as enzymatic synthesis or solid phase synthesis. In one aspect, a dsRNA molecule or directional trigger as disclosed herein is chemically synthesized. In another aspect, a dsRNA molecule or directional trigger as disclosed herein is enzymatically produced. In a further aspect, a dsRNA molecule or directional trigger as disclosed herein is enzymatically produced in vitro. The actual synthesis of the polynucleotides is well within the capabilities of one skilled in the art and can be accomplished via established methodologies as detailed in, for example, "Molecular Cloning: A Laboratory Manual," Sambrook et al., (1989); "Current Protocols in Molecular Biology," Volumes I-III Ausubel, R. M., ed. (1994); Ausubel et al., "Current Protocols in Molecular Biology," John Wiley and Sons, Baltimore, Md. (1989); Perbal, "A Practical Guide to Molecular Cloning," John Wiley & Sons, New York (1988) and "Oligonucleotide Synthesis," Gait, M. J., ed. (1984) utilizing solid phase chemistry, e.g., cyanoethyl phosphoramidite followed by deprotection, desalting and purification by for example, an automated trityl-on method or HPLC. Equipment and reagents for executing solid-phase synthesis are commercially available from, for example, Applied Biosystems. Any other means for such synthesis may also be employed, for example, kits from Ambion have DNA ligated on the 5' end that encodes a bacterial T7 polymerase promoter that makes RNA strands that can be assembled into a dsRNA. Alternatively, dsRNA molecules can be produced from expression cassettes in bacterial cells that have regulated or deficient RNase III enzyme activity. In one aspect, design parameters such as Reynolds score and Tuschl rules are known in the art and are used in selecting polynucleotide sequences effective in gene silencing. In another aspect, random design or empirical selection of polynucleotide sequences is used in selecting polynucleotide sequences effective in gene silencing. In a further aspect, the sequence of a polynucleotide is screened against the genomic DNA of the intended plant to minimize unintentional silencing of other genes.

Following synthesis, nucleic acid molecules of the present disclosure may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing and/or stabilization of the duplex strands.

The instant disclosure provides a recombinant construct comprising a plant expressible promoter operably linked to a nucleotide sequence encoding a directional trigger as described herein. In one embodiment, a promoter used herein is selected from the group consisting of a constitutive promoter, a tissue-specific promoter, and an inducible promoter. In one embodiment, a constitutive promoter is the CaMV 35S promoter. In another embodiment, a promoter is an abiotic stress inducible promoter.

The instant disclosure also provides a transgenic plant expressing a directional trigger from the recombinant construct described above. In one embodiment, the directional trigger is stably expressed in the transgenic plant. In another embodiment, the directional trigger is transiently expressed in the transgenic plant.

A dsRNA molecule or directional trigger of the instant disclosure can comprise various chemical modifications including, but not limited to, modified bases, modified sugar backbone, and modified internucleoside linkages. In one aspect, a dsRNA molecule or directional trigger as disclosed herein is chemically modified which modification is capable of enhancing the delivery of the dsRNA molecule or directional trigger into a plant cell, improving its stability in a plant cell, or both. In a further aspect, a dsRNA molecule or directional trigger comprises a cholesterol moiety. In one aspect, a dsRNA molecule or directional trigger as disclosed herein is a combination of ribonucleotides and deoxyribonucleotides, e.g., synthetic polynucleotides consisting mainly of ribonucleotides but with one or more terminal deoxyribonucleotides.

In one aspect, a dsRNA molecule or directional trigger as disclosed herein comprises one or more modified nucleotides of any kind in any part of the directional trigger, preferentially, in a 5' or 3' overhang. Exemplary modified RNA nucleotides can be found in Limbach et al. Summary: the modified nucleosides of RNA. Nucleic Acids Res. 1994, 22(12):2183-96; and Abeydeera et al. 2008, Modified Nucleosides in RNA. Wiley Encyclopedia of Chemical Biology. 1-14, both of which are incorporated by reference in their entireties. Further exemplary modified nucleotides can comprise a modified base including, but not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. In another aspect, a dsRNA molecule or directional trigger as disclosed herein includes a non-canonical nucleotide such as inosine, thiouridine, or pseudouridine.

In another aspect, a dsRNA molecule or directional trigger as disclosed herein comprises a modified polynucleotide backbone including, but not limited to, phosphorothioates, chiral phosphorothioates, phosphorodithioates, phosphotriesters, aminoalkyl phosphotriesters, methyl and other alkyl phosphonates, phosphinates, phosphoramidates, thionophosphoramidates, thionoalkylphosphonates, thionoalkylphosphotriesters, and boranophosphates.

In another aspect, a dsRNA molecule or directional trigger as disclosed herein is one active ingredient of a herbicidal, insecticidal, or pesticidal composition. A dsRNA molecule or directional trigger of the instant disclosure can be part of a composition further comprising various molecules or agents. In one aspect, a dsRNA molecule or directional trigger as disclosed herein is formulated with counter-ions or other molecules that are known to associate with nucleic acid molecules, e.g., tetraalkyl ammonium ions, trialkyl ammonium ions, sulfonium ions, lithium ions, and polyamines such as spermine, spermidine, or putrescine. In another aspect, a dsRNA molecule or directional trigger as disclosed herein is formulated with a non-polynucleotide herbicide (e.g., glyphosate, 2,4-dichloropropionic acid, bromoxynil, sulfonylurea, imidazolinone, triazolopyrimidine, pyrimidyloxybenzoates, phthalide, bialaphos, phosphinothricin, glufosinate, atrazine, dicamba, cyclohexanedione (sethoxydim), and aryloxyphenoxypropionate (haloxyfop)). In a further aspect, a dsRNA molecule or directional trigger as disclosed herein constitutes an active ingredient of a liquid herbicidal composition.

In a further aspect, a dsRNA molecule or directional trigger as disclosed herein is formulated with a transferring agent or permeability-enhancing agent which conditions the surface of a plant tissue, e.g., seed, leaves, stems, roots, flowers, or fruits, for permeation by the dsRNA molecule or directional trigger into plant cells. The transfer of a dsRNA molecule or directional trigger as disclosed herein into plant cells can be facilitated by the prior or contemporaneous application of a transferring agent to the plant tissue. The transferring agent enables a pathway for a dsRNA through cuticle wax barriers, stomata and/or cell wall or membrane barriers and into plant cells.

Suitable agents to facilitate transfer of a dsRNA molecule or directional trigger into a plant cell include agents that increase permeability of the exterior of the plant or that increase permeability of plant cells to oligonucleotides or polynucleotides. Such agents include, but are not limited to, a chemical agent, a physical agent, or combinations thereof. Chemical agents for conditioning includes, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. A transferring agent contemplated herein can further comprise a humectant or a chelating agent.

Exemplary agents or treatments for conditioning a plant for permeation include, but are not limited to, emulsions, reverse emulsions, liposomes, and other micellar-like compositions. Further exemplary agents or treatments include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils, paraffinic oils, polyol-fatty acid esters, and oils with short-chain molecules modified with amides or polyamines such as polyethyleneimine or N-pyrrolidine. A composition comprising a dsRNA molecule or directional trigger as disclosed herein can further comprise an organic or inorganic salt. In one aspect the salt is an ammonium salt, for example, ammonium sulfate.

Exemplary surfactants which facilitate the uptake of a dsRNA into plant cells include sodium or lithium salts of fatty acids (such as tallow or tallowamines or phospholipids) and organosilicone surfactants. Further exemplary surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet L-77 surfactant). When Silwet L-77 surfactant is used to treat plant seed, leaves or other surfaces, concentrations in the range of about 0.015 to about 2% by weight (wt %) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 wt %) are efficacious in preparing a seed, leaf or other plant surface for transfer of a dsRNA molecule or directional trigger into plant cells.

Exemplary physical agents facilitating the uptake of a dsRNA into plant cells include, but are not limited to, (a) abrasives such as carborundum, corundum, sand, calcite, pumice, garnet, and the like, (b) nanoparticles such as carbon nanotubes, or (c) a physical force. Carbon nanotubes are disclosed by Kam et al. (2004) J. Am. Chem. Soc., 126 (22):6850-6851, Liu et al. (2009) Nano Lett., 9(3):1007-1010, and Khodakovskaya et al. (2009) ACS Nano, 3(10):

3221-3227. Physical force agents can include heating, chilling, the application of positive pressure, or ultrasound treatment.

In another aspect, a dsRNA molecule or directional trigger as disclosed herein can be functionally associated with a cell-penetrating peptide which is a peptide that comprises a short (about 12-30 residues) amino acid sequence or functional motif that confers the energy-independent (e.g., non-endocytotic) translocation properties associated with transport of the membrane-permeable complex across the plasma and/or nuclear membranes of a cell. Cell-penetrating peptides used in the membrane-permeable complex of the present disclosure preferably comprise at least one non-functional cysteine residue, which is either free or derivatized to form a disulfide link with a dsRNA that has been modified for such linkage. Representative amino acid motifs conferring such properties are listed in U.S. Pat. No. 6,348,185, the contents of which are expressly incorporated herein by reference. Cell-penetrating peptides of the present disclosure preferably include, but are not limited to, penetratin, transportan, pIsl, TAT(48-60), pVEC, MTS, and MAP.

A dsRNA molecule or directional trigger or a composition comprising a dsRNA molecule or directional trigger of the instant disclosure can be applied to a plant or plant part by any method known in the art, e.g., spraying, drenching, soaking, or coating with a powder, emulsion, suspension, or solution. In one aspect, a dsRNA molecule or directional trigger as disclosed herein is exogenous to a plant cell.

The instant disclosure also provides plants and parts thereof treated with a dsRNA molecule or directional trigger as disclosed herein. The instant disclosure further provides plants and parts thereof comprising a dsRNA molecule or directional trigger as disclosed herein.

In one aspect, plants and parts thereof treated with a dsRNA molecule of the instant disclosure comprise reduced expression of at least 1, 2, or 3 target genes of the dsRNA molecule. In another aspect, plants and parts thereof treated with a dsRNA molecule of the instant disclosure comprise a partial reduction of the expression of at least 1, 2, or 3 target genes of the dsRNA molecule. In a further aspect, plants and parts thereof treated with a dsRNA molecule of the instant disclosure comprise a substantial reduction of the expression of at least 1, 2, or 3 target genes of the dsRNA molecule. In a further aspect, plants and parts thereof treated with a dsRNA molecule of the instant disclosure comprise an effective elimination of the expression of at least 1, 2, or 3 target genes of the dsRNA molecule.

In one aspect, plants and parts thereof comprising a dsRNA molecule of the instant disclosure comprise reduced expression of at least 1, 2, or 3 target genes of the dsRNA molecule. In another aspect, plants and parts thereof comprising a dsRNA molecule of the instant disclosure comprise a partial reduction of the expression of at least 1, 2, or 3 target genes of the dsRNA molecule. In a further aspect, plants and parts thereof comprising a dsRNA molecule of the instant disclosure comprise a substantial reduction of the expression of at least 1, 2, or 3 target genes of the dsRNA molecule. In a further aspect, plants and parts thereof comprising a dsRNA molecule of the instant disclosure comprise an effective elimination of the expression of at least 1, 2, or 3 target genes of the dsRNA molecule.

Any commercially or scientifically valuable plant is envisaged in accordance with some embodiments of the disclosure. Plants that are particularly useful in the methods of the disclosure include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present disclosure.

According to some embodiments of the disclosure, the plant used by the method of the disclosure is a crop plant including, but not limited to, cotton, Brassica vegetables, oilseed rape, sesame, olive tree, palm oil, banana, wheat, corn or maize, barley, alfalfa, peanuts, sunflowers, rice, oats, sugarcane, soybean, turf grasses, barley, rye, sorghum, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, quinoa, spinach, squash, onion, leek, tobacco, potato, sugarbeet, papaya, pineapple, mango, *Arabidopsis thaliana*, and also plants used in horticulture, floriculture or forestry, such as, but not limited to, poplar, fir, eucalyptus, pine, an ornamental plant, a perennial grass and a forage crop, coniferous plants, moss, algae, as well as other plants available on the internet at, for example, nationmaster.com/encyclopedia/Plantae.

According to a specific embodiment, the plant is selected from the group consisting of corn, rice, wheat, tomato, cotton and sorghum. In certain embodiments, the plant is a corn plant. In certain embodiments, the plant is a rice plant. In certain embodiments, the plant is a wheat plant. In certain embodiments, the plant is a cotton plant. In certain embodiments, the plant is a sorghum plant.

Introduction of the compositions of the present disclosure can be performed to any organs/cells of the plant (as opposed to seeds) using conventional delivery methods such as particle bombardment, grafting, soaking and the like.

In one aspect, the instant disclosure also provides a plant seed treated with a composition comprising a dsRNA molecule or directional trigger as disclosed herein. In another aspect, the instant disclosure also provides a plant seed comprising a dsRNA molecule or directional trigger as disclosed herein.

In one aspect, a directional trigger-comprising plant or seed as disclosed herein comprises one or more enhanced traits. As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this disclosure an enhanced trait is selected from group consisting of enhanced water use efficiency, enhanced cold tolerance, increased yield, enhanced nitrogen use efficiency, enhanced seed protein and enhanced seed oil. In an important aspect of the disclosure the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic or non-transgenic plant of the present disclosure can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Nucleic acid molecules as disclosed herein can also be used to provide plants having improved growth and development, and ultimately increased yield, as the result of modified expression of plant growth regulators or modification of cell cycle or photosynthesis pathways. Also of interest is the generation of transgenic or non-transgenic plants that demonstrate enhanced yield with respect to a seed component that may or may not correspond to an increase in overall plant yield; such properties include enhancements in seed oil, seed molecules such as protein and starch, oil components as may be manifest by an alterations in the ratios of seed components.

The instant disclosure further provides a container of plant seeds treated with a dsRNA molecule or directional trigger as disclosed herein. A container of treated seeds of the instant disclosure may contain any number, weight, or volume of seeds. For example, a container can contain at least, or greater than, 100, 200, 300, 400, 500, 600, 700, 800, 900, 1000, 1500, 2000, 2500, 3000, 3500, 4000 or more seeds. Alternatively, the container can contain at least, or greater than, 1 ounce, 5 ounces, 10 ounces, 1 pound, 2 pounds, 3 pounds, 4 pounds, 5 pounds or more seeds. Containers of seeds may be any container available in the art. By way of non-limiting example, a container may be a box, a bag, a packet, a pouch, a tape roll, or a tube.

The instant disclosure provides a method of regulating the expression of two or more genes of interest simultaneously by introducing into a plant cell a dsRNA molecule or directional trigger as disclosed herein. Also provided is a method of disrupting a metabolic pathway by introducing into a plant cell a dsRNA molecule or directional trigger as disclosed herein which targets two or more genes of interest in the metabolic pathway. Further provided is a method of simultaneously regulating the expression of two or more genes of interest selected from the group consisting of a plant endogenous gene sequence, a plant phytopathogen gene sequence, a plant viral gene sequence, a plant insect gene sequence, and combinations thereof, wherein the method comprises introducing into a plant cell a dsRNA molecule or directional trigger as disclosed herein.

The instant disclosure also provides a method of increasing the homogeneity or uniformity of a sRNA population processed from a dsRNA molecule by a Dicer-like protein, wherein the method comprises introducing to a dsRNA molecule one, two, three, four, five or more features selected from the group consisting of (a) having a length between about 45 and about 75 nucleotides, (b) comprising one or more Adenine- or Uracil-rich linker sequences adjoining the two or more sRNA trigger sequences each of which encodes a sRNA duplex, (c) comprising a 3' overhang in the antisense strand, (d) comprising a Uracil at positions 20 and 21 in the antisense strand relative to terminus of the 3' overhang, (e) a 5' overhang of 3 to 5 nucleotides long, and (f) combinations thereof.

The instant disclosure also provides a method of enriching functional sRNAs processed from a trigger molecule, comprising introducing into a trigger molecule one, two, three, four, five or more features selected from the group consisting of (a) two or more sRNA trigger sequences each of which encodes a sRNA, where the two or more sRNA trigger sequences are not found in a single naturally occurring molecule or not contiguous in a single naturally occurring molecule, (b) having a length between about 45 and about 75 nucleotides, (c) comprising one or more Adenine- or Uracil-rich linker sequences adjoining the two or more sRNA trigger sequences, (d) comprising a 3' overhang in the antisense strand, (e) comprising a Uracil at positions 20 and 21 in the antisense strand relative to terminus of the 3' overhang, (f) a 5' overhang of 3 to 5 nucleotides, and (g) combinations thereof.

The instant disclosure also provides a method of producing a trigger molecule with pre-determined processing pattern, comprising introducing into a trigger molecule one, two, three, four, five or more features selected from the group consisting of (a) two or more sRNA trigger sequences each of which encodes a sRNA, where the two or more sRNA trigger sequences are not found in a single naturally occurring molecule or not contiguous in a single naturally occurring molecule, (b) having a length between about 45 and about 75 nucleotides, (c) comprising one or more Adenine- or Uracil-rich linker sequences adjoining the two or more sRNA trigger sequences, (d) comprising a 3' overhang in the antisense strand, (e) comprising a Uracil at positions 20 and 21 in the antisense strand relative to terminus of the 3' overhang, (f) a 5' overhang of 3 to 5 nucleotides, and (g) combinations thereof.

It is appreciated that certain features of the disclosure, which are, for clarity, described in the context of separate aspects, may also be provided in combination in a single aspect. Conversely, various features of the disclosure, which are, for brevity, described in the context of a single aspect, may also be provided separately or in any suitable subcombination or as suitable in any other described aspect of the disclosure. Certain features described in the context of various aspects are not to be considered essential features of those aspects, unless the aspect is inoperative without those elements. Various aspects and aspects of the present disclosure as delineated hereinabove and as claimed in the claims section below find experimental support in the following examples.

The following Examples are presented for the purposes of illustration and should not be construed as limitations.

EXAMPLES

Example 1

Figure 1A:
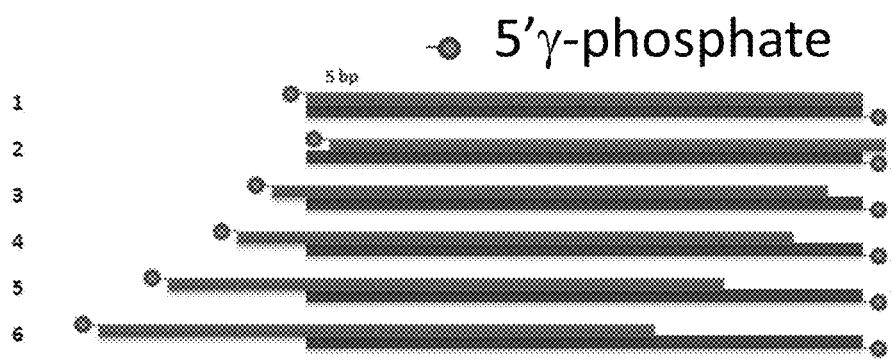

Evaluating the Influence of dsRNA Overhangs Over dsRNA Processing and its Ability to Induce Silencing Six dsRNA trigger molecules (SEQ ID NO:1/SEQ ID NO:57, SEQ ID NO:2/SEQ ID NO:57, SEQ ID NO:3/SEQ ID NO:57, SEQ ID NO:/4SEQ ID NO:57, SEQ ID NO:5/SEQ ID NO:57, and SEQ ID NO:6/SEQ ID NO:57), each of which comprises two strands of ~50 nucleotides with overhangs of various lengths, were incubated in wheat germ extract to test effects of overhang lengths over dsRNA processing. These dsRNA trigger molecules comprise target-specific sequences from a tomato (*Solanum lycopersicum*, Sl) 5-enolpyruvylshikimate-3-phosphate synthase (EPSPS) gene. All trigger molecules are 5'-end-labeled with P32 (FIG. 1A). Trigger 1 (SEQ ID NO:1/SEQ ID NO:57) has blunt ends. Trigger 2 (SEQ ID NO:2/SEQ ID NO:57) has 2-base 3' overhangs on both ends. Triggers 3-6 (SEQ ID NO:3/SEQ ID NO:57, SEQ ID NO:/4SEQ ID NO:57, SEQ ID NO:5/SEQ ID NO:57, and SEQ ID NO:6/SEQ ID NO:57) have on each end 2-base, 5-base, 10-base and 15-base 5'overhangs, respectively.

Figure 1B:
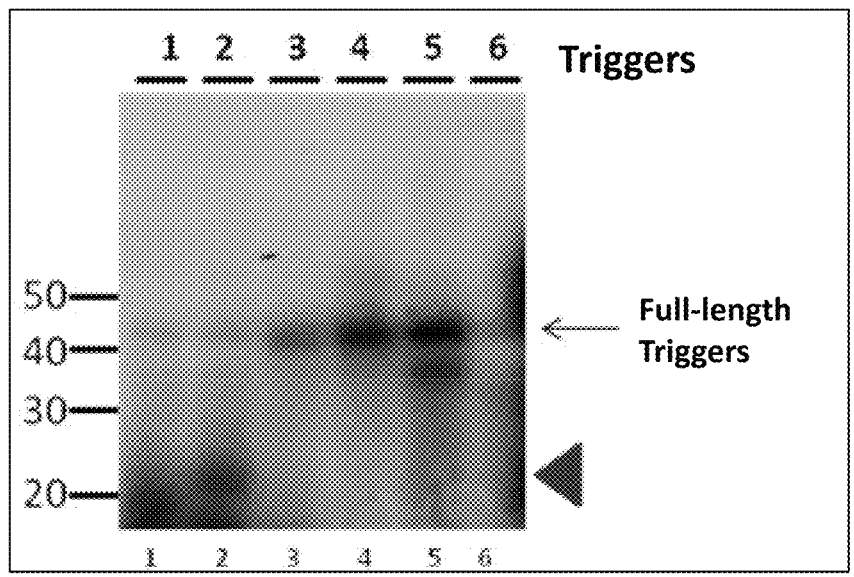
Figure 1B:
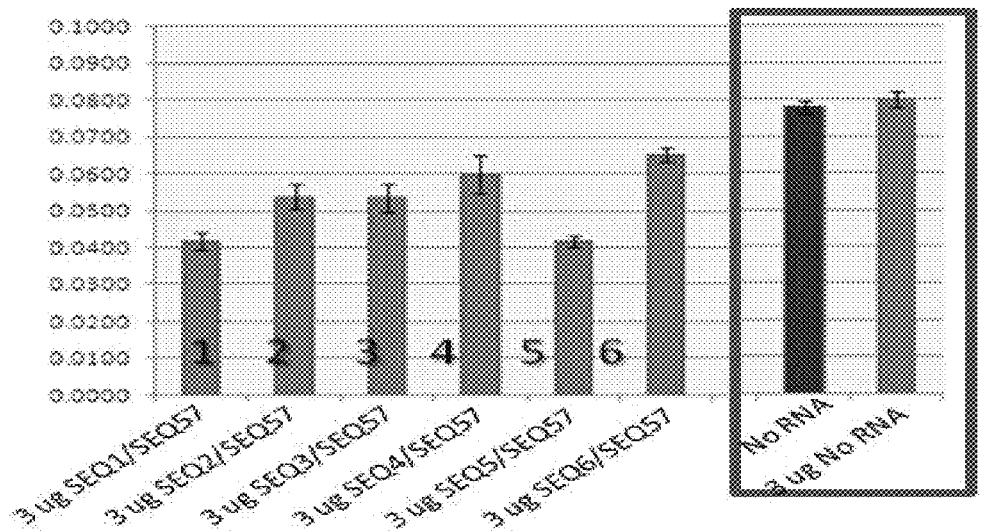

Specifically, 1 µl of 5' P32-end-labeled dsRNA trigger molecule (50,000 cpm) was incubated in a 40-µl reaction containing 30 µl of wheat germ extract (Promega), and 8 µl 5× Dicer reaction buffer (0.5 M NaCl, 100 µM GTP, 500 µM ATP, 10 mM creatine phosphate, 10 µg/ml creatine phosphokinase, 5 mM DTT, and 0.1 U/µl RNasin) (Promega) at 25° C. for 3 h. Reactions were stopped by the addition of 2× proteinase K buffer (200 mM Tris-HCl at pH 7.5, 25 mM EDTA, 300 mM NaCl, 2% (w/v) sodium dodecyl sulfate) followed by deproteinization with 2 mg/ml proteinase K at 65° C. for 15 min. Processed RNA products were precipitated with 3 volumes of cold ethanol and analyzed by electrophoresis in a 15% polyacrylamide sequencing gel. Both Triggers 1 and 2 were processed into small RNAs of 20~21 nucleotides, while almost no processed small RNA was observed from Triggers 3 to 6, supporting that 5' overhangs delay or prevent the processing of a dsRNA molecule (FIG. 1B).

Triggers 1 to 6 were further tested in *Nicotiana benthamiana* protoplasts for its ability to silence an EPSPS gene. Specifically, 3 µg of each of Triggers 1 to 6 were added to *Nicotiana benthamiana* protoplasts. Expression of the target EPSPS gene was quantified using Taqman quantitative PCR. Various extents of EPSPS down-regulation were observed from Triggers 1 to 6 (FIG. 1C). The degree of EPSPS silencing by triggers having 5' overhangs on both ends decreases as the 5' overhang length increases.

Example 2

Rational Design of a Directional Trigger

To improve the silencing efficiency of a dsRNA molecule, various sequence or structural features were incorporated into a dsRNA molecule to form a directional trigger. These sequence or structural features facilitate processing a dsRNA following a more predictable pattern and thereby allow for a more focused production of small RNAs functional in silencing intended target genes (FIG. 2 to FIG. 5). Structural features include, without limitation, directional initiation of processing by a Dicer-like protein from one end with a 3' overhang, and use of a 5' overhang in the opposite end blocking initiation of processing by Dicer-like proteins from that end.

Figure 2A:
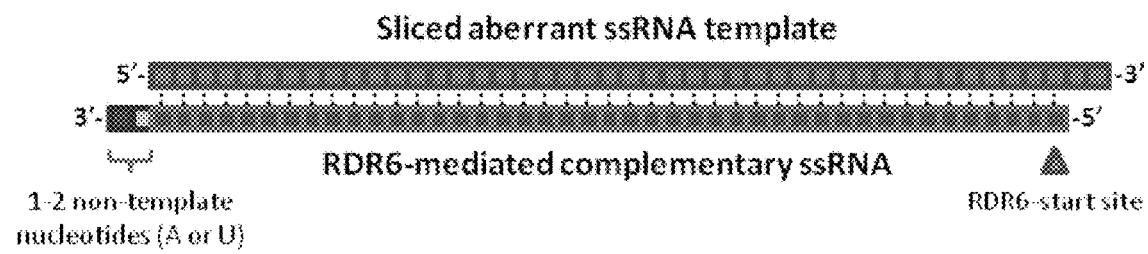
FIGS. 2A-2B: A comparison between a dsRNA molecule synthesized by a RNA dependent RNA polymerase (RDR, RDR6 shown as an example) (FIG. 2A), and one embodiment of a directional trigger as disclosed herein which comprises on their antisense strands a 2-nt 3' overhang ("3' initiator overhang") and a 5' overhang ("5' blocker overhang") (FIG. 2B). In contrast to an RDR-synthesized dsRNA molecule that has 3' overhangs at both ends and lacks directionality when processed by a Dicer protein, a directional trigger is processed predominantly starting for the end with a 3' initiator overhang.
Figure 2B:
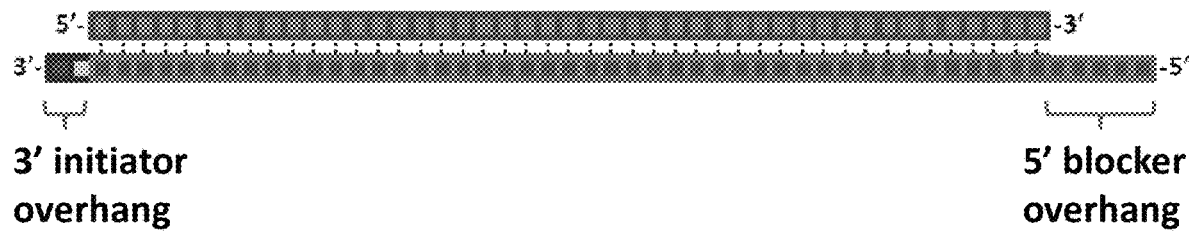

A dsRNA molecule synthesized by a RNA dependent RNA polymerase (RDR) (FIG. 2A, RDR6 shown as an example) comprises 3' overhangs on both ends, and therefore is processed by a Dicer-like protein at similar frequencies starting from either end. In contrast, an exemplary directional trigger comprises on its antisense strand a 2-nt 3' overhang ("3' initiator overhang") and a 5' overhang ("5' blocker overhang") which, without being bound to any scientific theory or mechanism, favors and disfavors the initiation of dicer processing from that end, respectively (FIG. 2B). Accordingly, a rationally designed directional trigger predominantly produces siRNA products that are in a pre-programmed and predictable phase (e.g., a phase interval of ~21 nucleotides starting from the dsRNA end with a 3' overhang).

Figure 3:
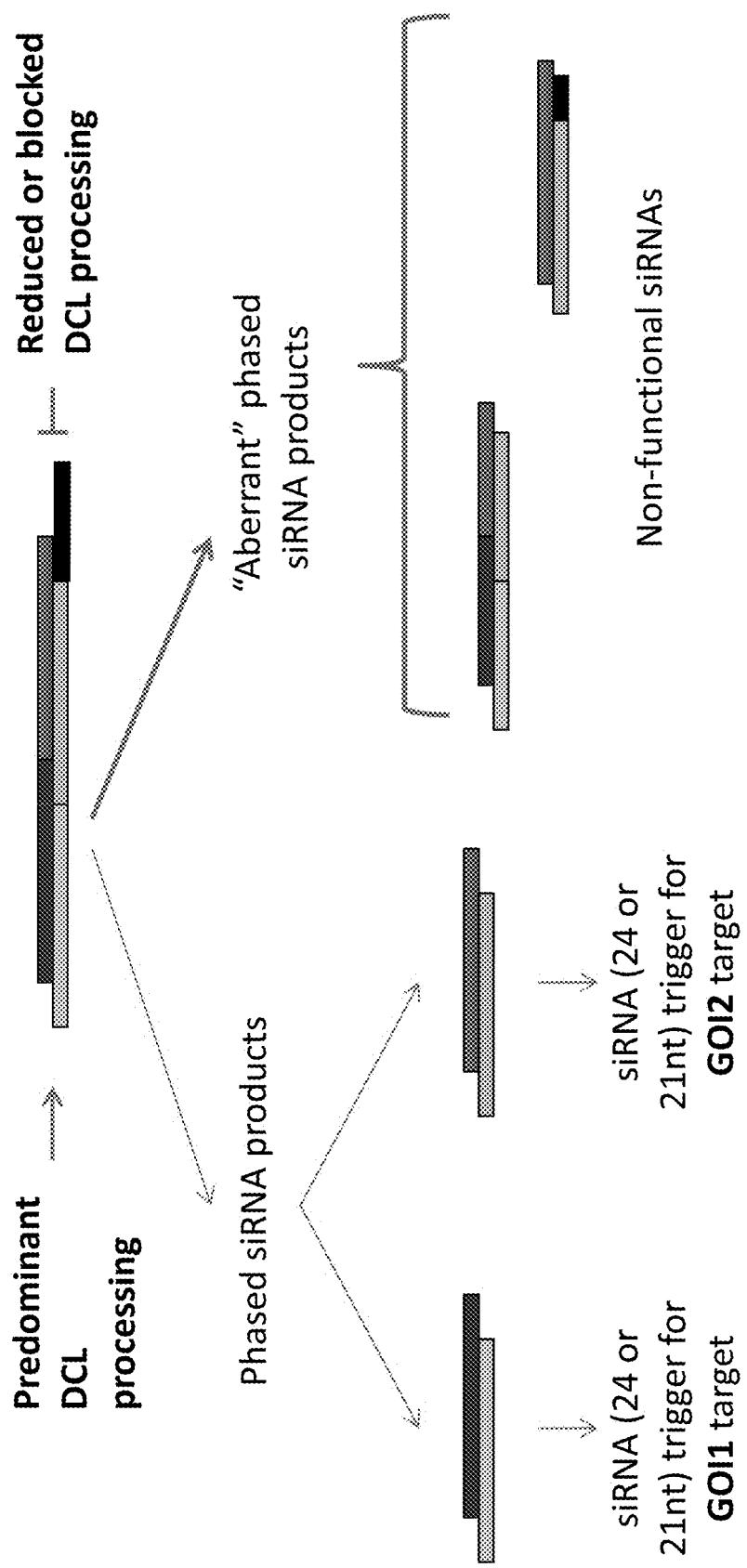
FIG. 3: A schematic representation of the rational design and processing of a directional dsRNA trigger, which is preferentially processed by Dicer-like proteins into two distinct, functional siRNAs in a phased manner. Design concepts include, without limitations, directional initiation of processing by Dicer-like proteins from one end with a 3' overhang, and use of a 5' overhang in the opposite end blocking initiation of processing by Dicer-like proteins from that end. A rationally designed directional chimeric dsRNA trigger molecule predominantly produces siRNA products that are in a proper phase to target two genes of interest (GOI1 and GOI2). Meanwhile, the processing of a directional dsRNA trigger leads to only a minor fraction of its siRNA products with an aberrant phase. "Aberrant" phased siRNA products have at best a partial complementarity with a target sequence which are not capable of triggering silencing of the target.

A pre-programmed and predictable processing pattern also allows a dsRNA molecule to give rise to multiple distinct siRNAs in proper phases so that each of the siRNAs is functional in promoting the silencing of its intended target. For example, an exemplary directional chimeric trigger predominantly produces siRNA products that are in a proper phase to target two genes of interest (GOI1 and GOI2) (FIG. 3). Meanwhile, the processing of a directional dsRNA trigger leads to only a minor fraction of its siRNA products with an aberrant phase (FIG. 3). Aberrantly phased siRNA products have at best a partial complementarity with a target sequence which are therefore not capable of promoting target silencing (e.g., non-functional siRNAs in FIG. 3).

Figure 4:
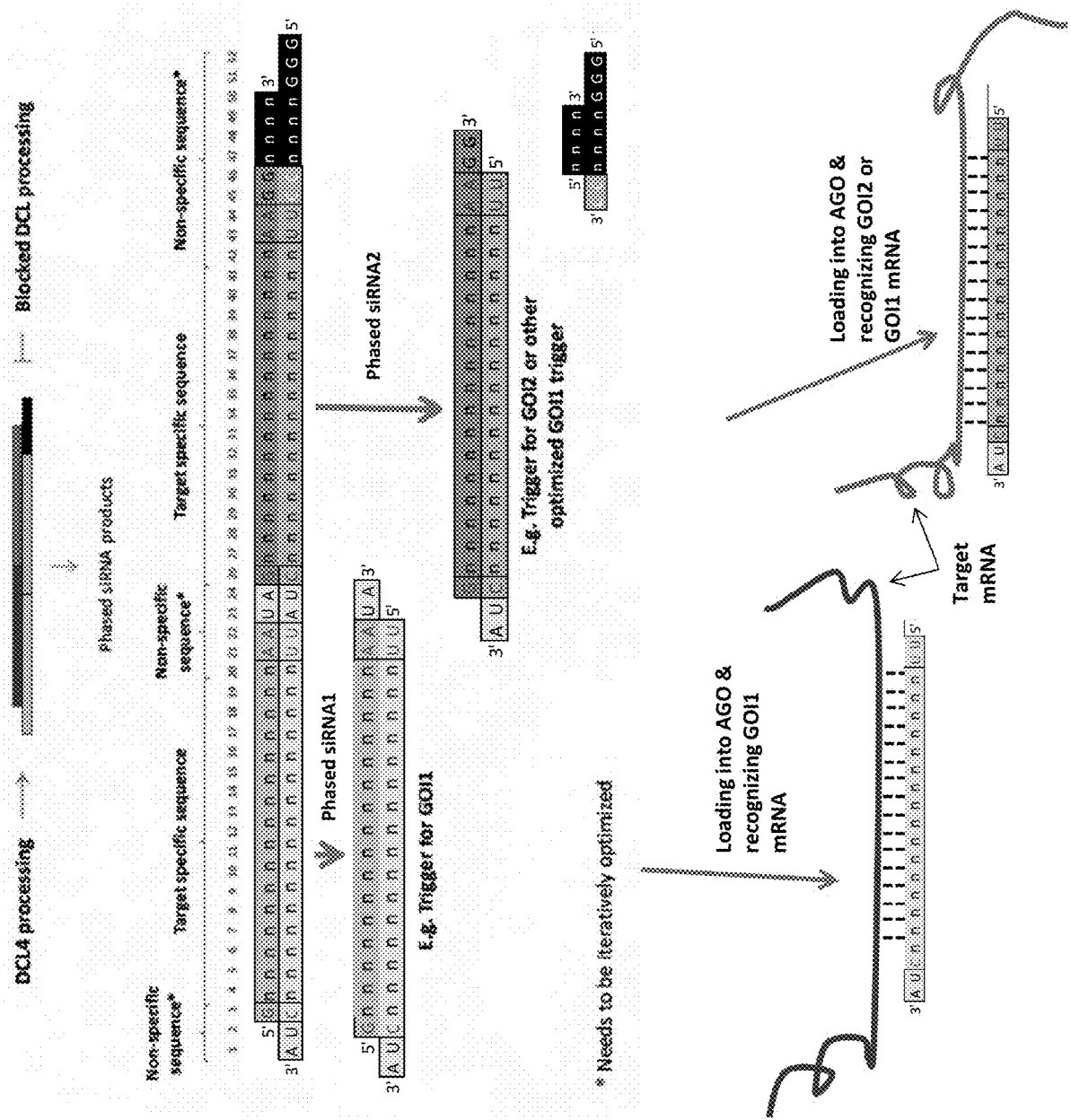
FIG. 4: A schematic representation of a directional dsRNA trigger (SEQ ID NO:83 and SEQ ID NO:84, shown for illustration purposes) which is preferentially processed by a Dicer-like protein to at least two distinct siRNAs in a phased manner. As shown, the two distinct siRNAs recognize sequences in the same or different target genes (GOI1 only as shown in SEQ ID NO:85, or GOI1 and GOI2, as shown in SEQ ID NO:87). Both siRNA1 and siRNA2 comprise a UU di-nucleotide at the 5' end of the antisense strand and a G at the 5' end of the sense strand (SEQ ID NO:86). The antisense strands of siRNA1 and siRNA2 starting with a UU di-nucleotide are preferentially loaded into Argonaute proteins (AGO) and recognize target gene mRNA molecules leading to target gene silencing.

Additional features were also incorporated into a directional trigger, for example, a AU-rich linker between two target-specific sequences (FIG. 4 and FIG. 5). An exemplary directional trigger (FIG. 4) can be processed into two distinct siRNAs recognizing sequences in the same or different target genes (GOI1 only, or GOI1 and GOI2). Both siRNA1 and siRNA2 comprise a UU di-nucleotide at the 5' end of the antisense strand and a G at the 5' end of the sense strand. Antisense strands of siRNA1 and siRNA2 starting with a UU di-nucleotide are preferentially loaded into Argonaute proteins (AGO) and recognize target gene mRNA molecules leading to target gene silencing. Target-specific sequences are sequences that are essentially identical, identical, or essentially complementary, or complementary, to a sequence of a target gene. Non-specific sequences are sequences that are not related to a target gene and can vary in both length and composition from those shown in FIG. 4.

A further schematic comparison between an exemplary directional dsRNA trigger and a non-directional dsRNA trigger is shown in FIG. 5. An exemplary directional dsRNA trigger comprises target-specific sequences from genes of interest (GOIs) on its sense strand. The antisense strand of the exemplified directional dsRNA trigger comprises both a 3' overhang (2-nt exemplified) and a 5' overhang (3-5 nucleotides or longer). A Dicer-like protein cleaves a first 21-24 mer (siRNA1) from a directional dsRNA trigger preferentially starting from the end with a 3' overhang, and continues to produce a second 21-24 mer (siRNA2) which is immediately next to the first 21-24 mer (e.g., in phase with the first 21-24 mer). Accordingly, the exemplified directional dsRNA trigger produces a collection of 21-24 mers (two 21-24 mers are shown in the figure) in a phased manner with siRNA1 and siRNA2 being the predominant species. Further, both siRNA1 and siRNA2 comprise a UU di-nucleotide at the 5' end of their antisense strands and a G at the 5' end of their sense strands. Antisense strands of siRNA1 and siRNA2 starting with a UU di-nucleotide are preferentially loaded into Argonaute proteins (AGO), and are also called guide strands which guide the recognition of target gene mRNA sequences and lead to target gene silencing.

Figure 5B:
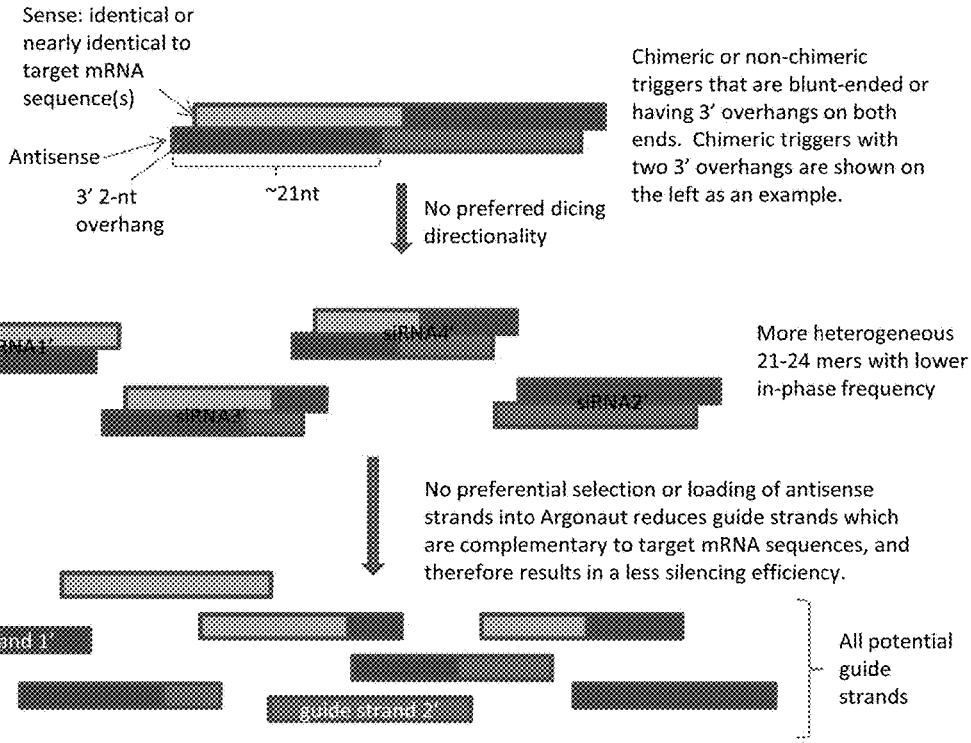

A non-directional dsRNA trigger, however, has no directionality bias towards either end of the trigger when processed by a dicer-like protein. Accordingly, 21-24 mers produced from a non-directional dsRNA trigger are more heterogeneous. In-phase 21-24 mers (e.g., siRNA1' and siRNA2') represent only a fraction of the total pool of 21-24 mers which also comprise substantial out-of-phase 21-24 mers (e.g., siRNA3' and siRNA4'). Accordingly, a non-directional dsRNA trigger produces more diluted in-phase 21-24 mers compared to a directional trigger. A non-directional dsRNA trigger can be chimeric or non-chimeric, blunt-ended, having 3' overhangs on both ends, or a combination of these features. A chimeric trigger having two 3' overhangs is shown in FIG. 5B.

Further, 21-24 mers produced from a non-directional dsRNA trigger lack a UU di-nucleotide at the 5' end of their antisense strand and a G at the 5' end of their sense strand. Accordingly, neither the antisense strand, nor the sense strand is preferentially loaded into a AGO protein. Instead, each strand of every 21-24 mer can potentially be loaded into an AGO protein as a guide strand. However, only guide strands 1' and 2' are complementary to target sequences and capable of recognizing target molecules to cause silencing. Therefore, a non-directional dsRNA trigger produces more diluted guide strands that are effective in causing silencing compared to guide strands produced from a directional dsRNA trigger.

Example 3

Evaluating Silencing Efficiencies of Directional dsRNA Trigger Using a Luciferase Reporter System in Wheat Germ Extract Exemplary directional dsRNA triggers were tested in wheat germ extract for their abilities to silence a luciferase reporter. Three directional dsRNA triggers were used (SEQ ID NO:7/SEQ ID NO:58, SEQ ID NO:8/SEQ ID NO:59, SEQ ID NO:9/SEQ ID NO:60, FIG. 6A). Each directional dsRNA trigger comprises two target-specific sequences. SEQ ID NO:7/SEQ ID NO:58 comprises one target-specific sequence from AtEPSPS and the other from AtCUT1. Both target-specific sequences in SEQ ID NO:8/SEQ ID NO:59 are from AtEPSPS, whereas both target-specific sequences in SEQ ID NO:9/SEQ ID NO:60 are from AtCUT1. A non-directional dsRNA trigger specifically targeting AtEPSPS (SEQ ID NO:10/SEQ ID NO:61) was also included as a control.

To evaluate silencing activities in wheat germ extract, a 50 µl reaction system was used which contained 25 µl wheat germ extract, 4 µl amino acid mix, a trigger (60 pmoles), and a fusion mRNA comprising a target of the trigger and firefly luciferase (3 pmoles). Reactions were incubated at 25° C. for 2 hours after which luciferase activities were read using the dual luciferase system (Promega) according to the manufacturer instructions.

Relative luciferase activities showed successful silencing of a fusion target mRNA AtEPSPS1:Fluc by SEQ ID NO:7/SEQ ID NO:58 and SEQ ID NO:8/SEQ ID NO:59 in wheat germ extract (FIG. 6B). AtEPSPS1:Fluc is an mRNA fusion between a full-length luciferase coding sequence and an AtEPSPS1 coding sequence which is targeted by directional triggers SEQ ID NO:7/SEQ ID NO:58, SEQ ID NO:8/SEQ ID NO:59, and non-directional trigger SEQ ID NO:10/SEQ ID NO:61. Relative luciferase activities also showed silencing of a fusion target mRNA AtCUT1:Fluc by SEQ ID NO:7/SEQ ID NO:58 and SEQ ID NO:9/SEQ ID NO:60, but not SEQ ID NO:8/SEQ ID NO:59 in wheat germ extract (FIG. 6C). AtCUT1:Fluc is an mRNA fusion between a full-length luciferase coding sequence and an AtCUT1 coding sequence that is targeted by triggers SEQ ID NO:7/SEQ ID NO:58 and SEQ ID NO:9/SEQ ID NO:60, but not SEQ ID NO:8/SEQ ID NO:59.

Example 4

Silencing of an Endogenous AtEPSPS1 Gene in *Arabidopsis* Protoplasts by Directional dsRNA Triggers Exemplary directional dsRNA triggers (SEQ ID NO:7/SEQ ID NO:58, SEQ ID NO:8/SEQ ID NO:59, SEQ ID NO:9/SEQ ID NO:60, FIG. 6A) were also tested in *Arabidopsis* protoplasts for their abilities to silence an endogenous AtEPSPS1 gene. A non-directional dsRNA trigger (SEQ ID NO:10/SEQ ID NO:61) was also included as a control. Preparation and transformation of *Arabidopsis* protoplasts and subsequent RNA extraction are described below in Example 5. SEQ ID NO:7/SEQ ID NO:58, SEQ ID NO:9/SEQ ID NO:60 and SEQ ID NO:10/SEQ ID NO:61 were all tested at a dosage of 200 pmol, while SEQ ID NO:8/SEQ ID NO:59, which contains two distinct siRNAs both targeting AtEPSPS1, was evaluated at a 50 pmol dosage. AtEPSPS1 expression was quantified by q-PCR.

Directional dsRNA triggers containing at least one target-specific sequence from AtEPSPS1 (SEQ ID NO:7/SEQ ID NO:58 and SEQ ID NO:8/SEQ ID NO:59) were capable of specifically down regulating AtEPSPS1 expression, while the directional dsRNA trigger only comprising target-specific sequences from AtCUT1 (SEQ ID NO:9/SEQ ID NO:60) could not (FIG. 6D). The lower dosage used for SEQ ID NO:8/SEQ ID NO:59 (50 pmol) which achieved a level of target down-regulation comparable to that by a higher dosage of trigger SEQ ID NO:7/SEQ ID NO:58 (200 pmol) shows that by having two target sequences from AtEPSPS1, trigger SEQ ID NO:8/SEQ ID NO:59 is more efficient in promoting silencing compared to trigger SEQ ID NO:7/SEQ ID NO:58 (having only one target sequence from AtEPSPS1). Both AtCUT1 (At1g68530) and AtEPSPS1 (At1g48860) genes are expressed in *Arabidopsis* leaves, which are sources for protoplast preparation.

Example 5

Isolation and PEG-Mediated Transformation of *Arabidopsis* Protoplasts and Subsequent RNA Extraction Isolation and PEG-mediated transformation of *Arabidopsis* protoplasts were conducted following standard protocols. In short, dark green, healthy *Arabidopsis* leaves were collected from about 3 week old plants prior to bolting. Leaves were then sliced on a piece of parafilm into approximately ~1 mm strips starting from the tip of a leaf and ending at ~2 to 3 mm from the petiole end of a leaf. Sliced leaves were then placed into a digestion solution in a Petri dishes (~50 leaves per Petri dish) with the adaxial leaf surface facing up. Leaf stripes were infiltrated with the digestion solution by the application of vacuum followed by an overnight incubation at room temperature in dark. Protoplasts were then released from leaves into the digestion solution after a gentle shaking of the Petri dish for 2-3 minutes at 40 RPM. Subsequently, the digestion mixture was filtered through two layers of 60-micron nylon mesh into a 50 ml conical tube. The Petri dish and leaf strips were rinsed by a 10 ml W5 solution which was subsequently filtered with collected. After a gentle and thorough mixing of protoplasts with the W5 rinsing solution, protoplasts were spun down in a Harrier benchtop centrifuge with a swinging bucket rotor at 100×g for 2 minutes. A protoplast pellet was resuspended in 10 ml W5 solution. Protoplasts collected from multiple Petri dishes were then pooled with protoplast concentration estimated using a hemacytometer (40 leaves generally give about 4-6×$10^6$ protoplasts). Prepared protoplasts were left in W5 solution on ice for at least 1 hour before transformation.

For analyzing the silencing of a reporter gene by a dsRNA molecule, 0.8 to 1×$10^5$ *Arabidopsis* protoplasts were used per transformation. For each transformation, 10 µg of each reporter construct together with 1.3 µg FLuc (pMON8796) and 0.3 µg hRLuc (pMON63934) as internal controls was used. For each construct, triplicate samples were used with a randomized transformation order. DNA constructs were firstly mixed with 150 µl protoplasts by gentle pipetting up and down. Subsequently, a 150 µl PEG solution was added into the protoplasts followed by mixing of the protoplast and PEG solutions by inverting the tube for about 1 minute. After a 4-minute incubation at room temperature, the PEG-protoplast transformation mixture was mixed with a 300 µl W5 solution followed by an incubation for 5-10 minutes. Protoplasts were then spun down by a centrifugation at 90×g for 1 minute, and subsequently resuspended in 1 ml WI solution. Transformed protoplasts were incubated in dark at room temperature for 4-6 hours prior to RNA extraction and Taqman or Transcriptional profiling analysis.

For RNA extraction, approximately 1×$10^6$ *Arabidopsis* protoplasts were spun down at 300×g for 2 minutes. The protoplast pellet was resuspended and lysed in 250 µl Buffer RLT (Qiagen RNeasy Mini Kit or Qiagen #79216) containing 1% β-Mercaptoethanol (BME). Protoplasts lysed by Buffer RLT were either stored in a −80° C. freezer or processed immediately for RNA isolation according to the standard plant/fungi extraction protocol found in Qiagen's RNeasy Mini Kit.

Example 6

Silencing of Tomato or Tobacco Target Genes by Directional dsRNA Triggers

Exemplary directional dsRNA triggers having tomato target genes were tested in wheat germ extract for their abilities to silence a luciferase reporter. Two directional dsRNA triggers were tested (SEQ ID NO:11/SEQ ID NO:62, SEQ ID NO:12/SEQ ID NO:63, FIG. 7A). SEQ ID NO:11/SEQ ID NO:62 and SEQ ID NO:12/SEQ ID NO:63 each comprise two target sequences, one from (*Solanum lycopersicum*, Sl) phytoene desaturase (SlPDS) and the other from SlEPSPS. Arrangements of the two target sequences are reversed between SEQ ID NO:11/SEQ ID NO:62 and SEQ ID NO:12/SEQ ID NO:63. SEQ ID NO:9/SEQ ID NO:60 was also included as a control, which comprises two target-specific sequences from AtCUT1. Processing of dsRNA molecules in wheat germ extract and monitoring of the luciferase reporter activity were performed essentially as described in Example 3.

Relative luciferase activities showed successful silencing of a fusion target mRNA SlPDS:Fluc by SEQ ID NO:11/SEQ ID NO:62 and SEQ ID NO:12/SEQ ID NO:63 in wheat germ extract (FIG. 7B). SlPDS:Fluc is an mRNA fusion between a full-length luciferase coding sequence and a SlPDS coding sequence which is targeted by SEQ ID NO:11/SEQ ID NO:62 and SEQ ID NO:12/SEQ ID NO:63, but not SEQ ID NO:9/SEQ ID NO:60. Relative luciferase activities also showed silencing of a fusion target mRNA SlEPSPS:Fluc by SEQ ID NO:11/SEQ ID NO:62 and SEQ ID NO:12/SEQ ID NO:63, but not SEQ ID NO:9/SEQ ID NO:60, in wheat germ extract (FIG. 7C). SlEPSPS:Fluc is an mRNA fusion between a full-length luciferase coding sequence and a SlEPSPS coding sequence which is targeted by triggers SEQ ID NO:11/SEQ ID NO:62 and SEQ ID NO:12/SEQ ID NO:63, but not SEQ ID NO:9/SEQ ID NO:60.

Directional dsRNA triggers SEQ ID NO:11/SEQ ID NO:62 and SEQ ID NO:12/SEQ ID NO:63 were further tested in *Nicotiana benthamiana* (Nb) protoplasts for their abilities to silence an endogenous NbEPSPS1 gene. NbEPSPS1 expression was evaluated by Northern blots following treating *Nicotiana benthamiana* protoplasts with SEQ ID NO:11/SEQ ID NO:62 and SEQ ID NO:12/SEQ ID NO:63 (FIG. 7D). Quantification of NbEPSPS1 expression via either a 5' probe or a 3' probe indicates that both SEQ ID NO:11/SEQ ID NO:62 and SEQ ID NO:12/SEQ ID NO:63 are capable of silencing NbEPSPS1 in *Nicotiana benthamiana* protoplasts (FIG. 7E).

Example 7

A Comparison Between a Directional dsRNA Trigger and a Non-Directional Trigger A directional dsRNA trigger (SEQ ID NO:8/SEQ ID NO:59 targeting AtEPSPS1, see FIG. 6A) and a non-directional trigger (SEQ ID NO:10/SEQ ID NO:61 targeting AtEPSPS1) were both tested in *Arabidopsis* protoplasts to compare their efficiencies in promoting the silencing of an endogenous AtEPSPS1 gene. *Arabidopsis* protoplast preparation and transformation were carried out essentially as described in Examples 4 and 5. Eight different dsRNA dosages (250, 125, 62.5, 31.3, 15.6, 7.8, 3.9, and 2.0 pmol) were tested. Directional triggers SEQ ID NO:14/SEQ ID NO:64 and SEQ ID NO:14/SEQ ID NO:81 which do not target AtEPSPS1 were also included as negative controls.

AtEPSPS1 expression was quantified using q-PCR with statistic significance evaluated by Student's t-test. AtEPSPS1 expression data showed that directional dsRNA trigger SEQ ID NO:8/SEQ ID NO:59 had a higher silencing efficiency compared to non-directional trigger SEQ ID NO:10/SEQ ID NO:61 (FIG. 8 and Table 1). SEQ ID NO:8/SEQ ID NO:59 reduced AtEPSPS1 expression by 34% and 39% when used at 125 and 250 pmol, respectively. SEQ ID NO:10/SEQ ID NO:61, however, was able to reduce AtEPSPS1 expression by 24% at the highest dose (250 pmol), and showed no silencing activity when used at a concentration of 125 pmol or lower. When used at the same concentration (e.g., 250 pmol), directional dsRNA trigger SEQ ID NO:8/SEQ ID NO:59 is more effective in reducing AtEPSPS1 expression compared to non-directional trigger SEQ ID NO:10/SEQ ID NO:61 (39% versus 24%). No AtEPSPS1 silencing was observed with the use of negative control triggers SEQ ID NO:14/SEQ ID NO:64 and SEQ ID NO:14/SEQ ID NO:81, demonstrating that the observed AtEPSPS1 silencing is sequence specific and dependent on the presence of a trigger molecule against AtEPSPS1.

TABLE 1

Quantification results of AtEPSPS1 expression in *Arabidopsis* protoplasts by q-PCR following treatments with dsRNA triggers at various dosages.

| Treatment | Mean SRC | Relative Expression changes |
|---|---|---|
| 01_250_SEQ ID NO: 10/SEQ ID NO: 61 | 75.552 | −24% |
| 02_125_SEQ ID NO: 10/SEQ ID NO: 61 | 97.548 | −2% |
| 03_62.5_SEQ ID NO: 10/SEQ ID NO: 61 | 150.617 | 51% |
| 04_31.3_SEQ ID NO: 10/SEQ ID NO: 61 | 113.633 | 14% |
| 05_15.6_SEQ ID NO: 10/SEQ ID NO: 61 | 145.935 | 46% |
| 06_7.8_SEQ ID NO: 10/SEQ ID NO: 61 | 121.434 | 21% |
| 07_3.90_SEQ ID NO: 10/SEQ ID NO: 61 | 121.01 | 21% |
| 08_2.0_SEQ ID NO: 10/SEQ ID NO: 61 | 147.592 | 48% |
| 09_250_SEQ ID NO: 8/SEQ ID NO: 59 | 60.51 | −39% |
| 10_125_SEQ ID NO: 8/SEQ ID NO: 59 | 65.922 | −34% |
| 11_62.5_SEQ ID NO: 8/SEQ ID NO: 59 | 93.578 | −6% |
| 12_31.3_SEQ ID NO: 8/SEQ ID NO: 59 | 105.186 | 5% |
| 13_15.6_SEQ ID NO: 8/SEQ ID NO: 59 | 98.586 | −1% |
| 14_7.8_SEQ ID NO: 8/SEQ ID NO: 59 | 114.773 | 15% |
| 15_3.90_SEQ ID NO: 8/SEQ ID NO: 59 | 124.326 | 24% |
| 16_2.0_SEQ ID NO: 8/SEQ ID NO: 59 | 128.81 | 29% |
| 17_250_SEQ ID NO: 14/SEQ ID NO: 64 | 145.988 | 46% |
| 18_125_SEQ ID NO: 14/SEQ ID NO: 64 | 119.543 | 20% |
| 19_62.5_SEQ ID NO: 14/SEQ ID NO: 64 | 144.543 | 45% |
| 20_31.3_SEQ ID NO: 14/SEQ ID NO: 64 | 139.518 | 40% |
| 21_15.6_SEQ ID NO: 14/SEQ ID NO: 64 | 136.958 | 37% |
| 22_7.8_SEQ ID NO: 14/SEQ ID NO: 64 | 139.309 | 39% |
| 23_3.90_SEQ ID NO: 14/SEQ ID NO: 64 | 118.386 | 18% |
| 24_2.0_SEQ ID NO: 14/SEQ ID NO: 64 | 135.544 | 36% |
| 25_250_SEQ ID NO: 14/SEQ ID NO: 81 | 140.861 | 41% |
| 26_125_SEQ ID NO: 14/SEQ ID NO: 81 | 111.536 | 12% |
| 27_62.5_SEQ ID NO: 14/SEQ ID NO: 81 | 131.118 | 31% |
| 28_31.3_SEQ ID NO: 14/SEQ ID NO: 81 | 129.451 | 29% |
| 29_15.6_SEQ ID NO: 14/SEQ ID NO: 81 | 133.988 | 34% |
| 30_7.8_SEQ ID NO: 14/SEQ ID NO: 81 | 147.589 | 48% |
| 31_3.90_SEQ ID NO: 14/SEQ ID NO: 81 | 126.356 | 26% |
| 32_2.0_SEQ ID NO: 14/SEQ ID NO: 81 | 154.903 | 55% |
| no trigger | 100 | baseline |

Table 1 shows the same dataset used in FIG. 8. Each experiment is shown in the Treatment column as "treatment number"_"trigger dosage"_"trigger name." For example, "01_250_SEQ ID NO:10/SEQ ID NO:61" refers to treatment number 01 which uses 250 pmol of trigger SEQ ID NO:10/SEQ ID NO:61. Mean SRC refers to an average readout of AtEPSPS1 expression level normalized to a no-trigger control which is set at 100. The rightmost column refers to the percentage of AtEPSPS1 expression change normalized to a no-trigger control (shown as "baseline" in the bottom row).

Example 8

Analyzing Small RNAs Processed from a Directional dsRNA Trigger by Deep Sequencing To confirm that the rational design of a directional dsRNA trigger indeed promotes dsRNA processing in a more predictable manner and enriches for small RNAs functional for silencing an intended target, small RNA deep sequencing was carried out to analyze the processing products of directional dsRNA triggers SEQ ID NO:7/SEQ ID NO:58, SEQ ID NO:8/SEQ ID NO:59, and SEQ ID NO:9/SEQ ID NO:60 (see FIG. 6A). Directional dsRNA triggers were first processed in wheat germ extract with processed RNA products collected and subject to deep sequencing thereafter. Deep sequencing results are summarized in Table 2. The sequencing results demonstrate that the processing of SEQ ID NO:7/SEQ ID NO:58, SEQ ID NO:8/SEQ ID NO:59, and SEQ ID NO:9/SEQ ID NO:60 into small RNAs of 21-24 nucleotides (21-24 mers) is directionally biased towards the 3' end of their antisense strands (AS strand). Specifically, 49%, 51%, and 69% of 21-24 mers are mapped to the 3' end of the antisense strand of SEQ ID NO:7/SEQ ID NO:58, SEQ ID NO:8/SEQ ID NO:59, and SEQ ID NO:9/SEQ ID NO:60, respectively.

these 10 duplexes, only 3 preferentially match to the 3' side of the trigger (the dsRNA end with a 5' overhang). Four top-ranked duplexes (two 21-nt and two 24-nt siRNAs) showed opposite strand biases. The two top-ranked 21-nt siRNAs are biased towards the antisense strand, while the two top-ranked 24-nt siRNAs have a bias to the sense strand.

Example 9

In Planta Processing of Directional Chimeric Triggers

A total of 20 µl of 4 µg/µl stock of dsRNA trigger (GFP targeting trigger alone-SEQ ID NO:65/SEQ ID NO:82 or

TABLE 2

The processing of directional dsRNA triggers SEQ ID NO: 7/SEQ ID NO: 58, SEQ ID NO: 8/SEQ ID NO:59, and SEQ ID NO: 9/SEQ ID NO: 60 (see FIG. 6A) into 21-24 mers is directionally biased towards the 3' end of the antisense strand (AS strand). "S strand" refers to the sense strand of a dsRNA trigger molecule.

| Trigger | T number | Targets | Total reads (all sizes) | Total reads (21-24 mer) | 21-24 from 3' of AS strand | 21-24 from 5' of S strand | % of 21-24 from 3' AS strand | % of 21-24 from 3' S strand |
|---|---|---|---|---|---|---|---|---|
| 1 | SEQ ID NO: 7/ SEQ ID NO: 58 | AtEPSPS/ AtCUT1 | 1654000 | 232000 | 112000 | 1200 | 49 | 0.5 |
| 2 | SEQ ID NO: 8/ SEQ ID NO: 59 | AtEPSPS1 | 176000 | 81630 | 42232 | 19.793 | 51 | 24 |
| 3 | SEQ ID NO: 9/ SEQ ID NO: 60 | AtCUT1 | 2456774 | 473000 | 430000 | 2000 | 69 | 0.4 |

A closer analysis of the deep sequencing results from directional dsRNA trigger SEQ ID NO:9/SEQ ID NO:60 further illustrates the directionality of SEQ ID NO:9/SEQ ID NO:60 processing and an enrichment of 21-24 mers that are functional in silencing SEQ ID NO:9/SEQ ID NO:60's intended target AtCUT1 (FIG. 9 and FIG. 10). FIG. 9B shows the size distribution and relevant abundance of RNA products from SEQ ID NO:9/SEQ ID NO:60 after processing in wheat germ extract. In total, 2,456,774 sequencing reads are mapped to trigger SEQ ID NO:9/SEQ ID NO:60, of which 2,107,001 reads (~85%) are from the antisense strand of trigger SEQ ID NO:9/SEQ ID NO:60 while 349,774 sequencing reads (~15%) are from the sense strand of trigger SEQ ID NO:9/SEQ ID NO:60. FIG. 9C shows that the size range of 21-24 nucleotides (21-24 mer) contains 473,000 sequencing reads (~19% of total sequencing reads), of which ~90% are mapped to the 3' end of the antisense strand of trigger SEQ ID NO:9/SEQ ID NO:60 with only ~0.4% from the 5' end of the sense strand. An bias towards the 3' end of the antisense strand compared to the antisense 5' end (~17% versus ~0.4%) supports a preferential, directional processing of SEQ ID NO:9/SEQ ID NO:60 starting from the end comprising a 2-nt 3' overhang.

Additional deep sequencing experiments were also conducted to analyze the pattern of directional trigger processing into siRNAs. A 48-nt directional trigger (SEQ ID NO:15, top row in FIG. 11) was also processed in wheat germ extract with small RNA products collected and subject to deep sequencing. Deep sequencing results for 21-24 mers were analyzed and assembled in silico to identify putative primary siRNA duplexes (e.g., perfect-match double-stranded 21-24 mers). These putative siRNA duplexes are ranked based on their relative abundance estimated by the sum of their absolute frequencies. Top ranked putative duplexes (only perfect-match 21-24 mers) were aligned against the BOL5.2 48-nt trigger sequence (FIG. 11). The top 10 putative siRNA duplexes amount to ~75% of all perfect match reads. Among chimeric GFP/MgChl-SEQ ID NO:66/SEQ ID NO:67) was applied to the adaxial side of leaves of Nicotiana benthamiana 16C transgenic plants (2-3 weeks old seedlings) and introduced into the plant cells. The final solution consisted of the dsRNA trigger and water. The solution was left to dry on the surface of the leaf for approximately one hour after which sandpaper was rolled on the leaf to deliver the dsRNA into plant cells.

Plant tissue was assessed for visual phenotype at four days post transfection. At the same time, tissue was harvested for Western Blot analysis. For each treatment two 5 mm leaf discs were placed in a frozen 1.5 mL microtube. The tissue was ground with a frozen plastic micropestle until a fine powder was formed. Approximately 20 µl of a buffer solution was added to each sample, followed by vortexing for thirty seconds. The buffer solution consisted of 50 mM Tris-HCl, pH 7.4; 2.5 mM MgCl2, 100 mM KCl; 0.1% Nonidet P-40 and one tablet of Complete proteinase inhibitor tablet (Roche). The extract was then centrifuged at maximum speed for 10 minutes at 4° C. in a microcentrifuge. The supernatant was transferred to a clean tube and centrifuged for an additional 5 minutes at 4° C. Total protein was quantified using the BCA assay (Pierce). For immunoblot analysis, 6 µg of total protein were analyzed using standard Western blotting procedures. GFP and MgChl were visualized using a 1:5000 dilution of polyclonal anti-GFP (Santa Cruz Biotechnologies) or polyclonal anti-MgChl (produced in house) rabbit antibodies, respectively, as illustrated in FIG. 12. This treatment was followed by the use of an HRP conjugate (goat anti-rabbit IgG-HRP; Santa Cruz Biotechnologies). Detection of the GFP or MgChl specific bands was performed by using the SuperSignalWest Pico chemiluminescent substrate (Pierce).

Visual examination of the plants at 4 days after treatment revealed suppression of GFP in both treatments, those treated with GFP-only trigger or those treated with the chimeric trigger to GFP and MgChl. However, only the leaves treated with the chimeric trigger targeting both GFP and MgChl displayed the MgChl suppression phenotype characterized by the presence of yellow/chlorotic foci, visible in plain light. Image J software was used to quantify the percentage reduction for both targets by measuring the band intensity after Western blot. The results are presented in Table 3. Target protein was reduced by at least 60%. The percent knockdown established for MgChl was likely underestimated since the tissue used for protein extraction consisted of both green and yellow sectors.

TABLE 3

Percent reduction of corresponding protein targets.
Values were calculated based on comparison of band intensity between untreated and trigger-treated samples.

|  | GFP % reduction | MgChl % reduction |
|---|---|---|
| Untreated | 0 | 0 |
| GFP-only trigger (T41817) | 100 | 0 |
| Chimeric trigger (T52255) | 95 | 60 |

Example 10

Mutations in the Central Portion of the Directional Trigger Sequence and Blunt Ends (at the Ends of the Trigger) Resulted in Loss of Efficacious Processing An evaluation of the efficacy of processing was undertaken by introducing mutations (SEQ ID NO:70/SEQ ID NO:71; see FIG. 13, panel A) within the complementary portion of the dsRNA trigger SEQ ID NO:68/SEQ ID NO:69, thus presumably inhibiting effective processing or dicing of the polynucleotide when introduced in *Arabidopsis* protoplasts. Additionally, a blunt ended dsRNA trigger (SEQ ID NO:72/SEQ ID NO:73; see FIG. 13, panel A) was also tested.

*Arabidopsis* protoplasts were transfected using standard procedures as described in Example 5, with 100 pmol each of dsRNA triggers, including a nonspecific trigger (SEQ ID NO:74/SEQ ID NO:75) as negative control, a directional trigger targeting only *Arabidopsis* Phytoene Desaturase (PDS) (SEQ ID NO:76/SEQ ID NO:77), a directional trigger targeting only *Arabidopsis* Phosphoribosylanthranilate transferase 1 (PAT1) (SEQ ID NO:78/SEQ ID NO:79), the directional trigger targeting both PDS and PAT1 (SEQ ID NO:68/SEQ ID NO:69), the mutated directional trigger (SEQ ID NO:70/SEQ ID NO:71), and the blunt ended trigger (SEQ ID NO:72/SEQ ID NO:73). RNA was extracted approximately 16-20 hrs after transfection and analyzed by Taqman. The result of this analysis are presented in FIG. 13, panel B.

In the analysis conducted on PDS transcript (FIG. 13, panel B, left side), a clear reduction of message levels is visible in the cells treated with the dsRNA targeting PDS only (SEQ ID NO: 76/SEQ ID NO:77) or in the cells treated with the chimeric PDS/PAT1 dsRNA trigger (SEQ ID NO:68/SEQ ID NO:69), but not in the cells treated with the mutated trigger (SEQ ID NO:70/SEQ ID NO:71) or the trigger with blunt ends (SEQ ID NO:72/SEQ ID NO:73). Likewise, when Taqman analysis was conducted assaying PAT1 mRNA levels (FIG. 13, panel B, right side), a reduction in message was only observed in the cells treated with dsRNA polynucleotides targeting PAT1 (SEQ ID NO:78/SEQ ID NO:79) or the chimeric PDS/PAT1 dsRNA (SEQ ID NO:68/SEQ ID NO:69) but not in the cells treated with the mutated trigger (SEQ ID NO:70/SEQ ID NO:71) or the trigger with blunt ends (SEQ ID NO:72/SEQ ID NO:73). The results further validate the activity of the directional triggers, indicating the importance of percentage complementarity in the target-specific sequences and the importance of the overhang length and orientation in proper processing of the siRNAs.

The invention claimed is:

1. A double stranded RNA (dsRNA) molecule comprising:
   a. a first strand comprising in the 5' to 3' direction
      i. a first sequence that is essentially identical to at least 18 consecutive nucleotides of a first target nucleotide sequence; and
      ii. a second sequence that is essentially identical to at least 18 consecutive nucleotides of a second target nucleotide sequence; and
   b. a second strand comprising in the 5' to 3' direction, a 5'-overhang, a nucleotide sequence that is essentially complementary to the first strand, and a 2 nucleotide 3'-overhang, wherein the 5'-overhang is 5 nucleotides in length and has a high GC content,
   wherein the first strand and the second strand are not linked by phosphodiester bonds,
   wherein the dsRNA molecule is processed to produce 21, 22, 23, and/or 24 nucleotide siRNAs, and
   wherein the production of the 21-24 nucleotide siRNAs is directionally biased towards the 3' end of the second strand of the dsRNA molecule.

2. The dsRNA molecule of claim 1, comprising sequences selected from:
   a. the 5 nucleotide 5'-overhang of the second strand having the sequence GCGCG;
   b. the 2 nucleotide 3'-overhang of the second strand having the sequence UA;
   c. the first strand further comprising the nucleotides GCCAC located 3' to the nucleotide sequence that is essentially identical to at least 18 consecutive nucleotides of the target nucleotide sequence;
   d. the 3' end of the first strand having a high GC content;
   e. the 3' end of the first strand that is not identical to the target nucleotide sequence; and
   f. any combination thereof.

3. The dsRNA molecule of claim 1, wherein the target nucleotide sequence is a coding region of a mRNA, a 5' untranslated region, a 3' untranslated region, an intron, a promoter, an enhancer, a terminator, an rRNA, a tRNA, a small nuclear RNA (snRNA), a small nucleolar RNA (snoRNA), a non-coding RNA involved in RNA interference, and any combination thereof.

4. The dsRNA molecule of claim 1, wherein the 2 nucleotide 3'-overhang comprises at least one modification that improves stability of the dsRNA molecule.

5. The dsRNA molecule of claim 1, wherein the first target nucleotide sequence and second target nucleotide sequence are from different genes.

6. The dsRNA molecule of claim 1, wherein the first target nucleotide sequence and second target nucleotide sequence are non-contiguous sequences of the same gene.

7. The dsRNA molecule of claim 1, wherein the first strand comprises one or more As between the first and second sequences.

8. The dsRNA molecule of claim 1, wherein the second sequence comprises
   a. a 5' G;
   b. a 5' GUA;
   c. a 5' GAA;
   d. a 3' AA; or
   e. any combination thereof.

9. The dsRNA molecule of claim 1, wherein the first and the second sequences are 21 nucleotides in length.

10. The dsRNA molecule of claim 1, wherein the first strand comprises in the 5' to 3' direction,
    a. a first nucleotide sequence that is identical to at least 18 consecutive nucleotides of a first target-nucleotide sequence;
    b. a second nucleotide sequence comprising 2 or more As; and
    c. a third nucleotide sequence that is identical to at least 18 consecutive nucleotides of a second targeted nucleotide sequence or at least 18 consecutive nucleotides of the first target nucleotide sequence,
    and wherein the second strand comprises in the 5' to 3' direction, a 5 nucleotide 5'-overhang, a nucleotide sequence that is complementary to the first strand, and a 2 nucleotide 3'-overhang.

11. A composition comprising the dsRNA molecule of claim 1.

12. A method of regulating expression of at least one target gene, comprising applying onto the surface of a plant or plant part the composition of claim 11, wherein the dsRNA molecule comprises a first strand comprising a nucleotide sequence that is essentially identical to at least 18 consecutive nucleotides of the target gene.

13. The method of claim 12, wherein the first strand of the dsRNA molecule comprises at least two, at least three, or at least four nucleotide sequences that are essentially identical to at least 18 consecutive nucleotides of at least two, at least three, or at least four target genes.

14. The method of claim 12, wherein the dsRNA molecule transfers from the surface of the plant or plant part into a cell of the plant or plant part.

15. The method of claim 14, wherein the dsRNA molecule suppresses the expression of at least one, at least two, at three, or at least four target genes.

16. A plant, plant part, or seed comprising the dsRNA molecule of claim 1, wherein the dsRNA molecule is exogenous to the plant, plant part, or seed.

17. The plant, plant part, or seed of claim 16, wherein the dsRNA molecule suppresses the expression of at least one, at least two, at least three, or at least four target genes in the plant, plant part, or seed.

* * * * *